United States Patent
Bogorad et al.

(10) Patent No.: US 12,186,406 B2
(45) Date of Patent: Jan. 7, 2025

(54) MATERIALS AND METHODS FOR TREATMENT OF HEREDITARY HAEMOCHROMATOSIS

(71) Applicant: CRISPR THERAPEUTICS AG, Zug (CH)

(72) Inventors: Roman Lvovitch Bogorad, Cambridge, MA (US); Chad Albert Cowan, Cambridge, MA (US); Ante Sven Lundberg, Cambridge, MA (US)

(73) Assignee: CRISPR THERAPEUTICS AG, Zug (CH)

( * ) Notice: Subject to any disclaimer, the term of this patent is extended or adjusted under 35 U.S.C. 154(b) by 406 days.

(21) Appl. No.: 17/371,386

(22) Filed: Jul. 9, 2021

(65) Prior Publication Data

US 2022/0008558 A1    Jan. 13, 2022

Related U.S. Application Data

(63) Continuation of application No. 16/084,531, filed as application No. PCT/IB2017/000317 on Mar. 16, 2017, now Pat. No. 11,083,799.

(60) Provisional application No. 62/323,890, filed on Apr. 18, 2016, provisional application No. 62/309,136, filed on Mar. 16, 2016.

(51) Int. Cl.
A61K 48/00    (2006.01)
A61K 9/00    (2006.01)
C12N 5/071    (2010.01)
C12N 5/0775    (2010.01)
C12N 15/10    (2006.01)
C12N 15/113    (2010.01)
C12N 15/90    (2006.01)

(52) U.S. Cl.
CPC ........ *A61K 48/0058* (2013.01); *A61K 9/0019* (2013.01); *A61K 48/005* (2013.01); *A61K 48/0066* (2013.01); *A61K 48/0075* (2013.01); *C12N 5/0663* (2013.01); *C12N 5/067* (2013.01); *C12N 15/102* (2013.01); *C12N 15/1138* (2013.01); *C12N 15/907* (2013.01); *C12N 2310/20* (2017.05)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,034,506 A | 1/1991 | Summerton et al. |
| 5,023,243 A | 6/1991 | Tullis |
| 5,082,830 A | 1/1992 | Brakel et al. |
| 5,130,302 A | 1/1992 | Spielvogel et al. |
| 5,134,066 A | 1/1992 | Rogers et al. |
| 5,109,124 A | 4/1992 | Ramachandran et al. |
| 5,112,963 A | 5/1992 | Pieles et al. |
| 5,118,802 A | 6/1992 | Smith et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Hobbs, Jr. |
| 5,264,423 A | 11/1993 | Cohen et al. |

(Continued)

FOREIGN PATENT DOCUMENTS

WO    WO1993/007883    4/1993
WO    WO1995/013365    5/1995

(Continued)

OTHER PUBLICATIONS

Yin et al., Nat. Biotechnol., 2014, 32: 551-553.*
Levy et al., Blood, 1999, 94: 9-11.*
Spasic et al., Cell Metabolism, 2008, 7: 173-178.*
Hendel et al., Nature Biotechnol., 2015, 33: 985-989.*
Zuris et al., Nature Biotechnol., 2015, 33: 73-80.*
Hanson et al., Am. J. Epidemiol., 2001, 154: 193-206.*
Angart et al., "Design of siRNA therapeutics from the molecular scale," Pharmaceuticals (Basel) 2013, 6(4), 440-468.
Arredondo et al., "HFE inhibits apical iron uptake by intestinal epithelial (Caco-2) Cells," The FASEB Journal 2001, 15(7), 1276-1278.
Barrett et al., "Reliable generation of induced pluripotent stem cells from human lymphoblastoid cell lines," Stem Cells Trans. Med. 2014, 3, 1429-1434.

(Continued)

*Primary Examiner* — Ileana Popa
(74) *Attorney, Agent, or Firm* — Dickinson Wright PLLC

(57) ABSTRACT

Materials and methods for treating a patient with hereditary hemochromatosis (HHC), both ex vivo and in vivo, and materials and methods for modulating the expression, function, or activity of a haemochromatosis (HFE) gene in a cell by genome editing.

20 Claims, 8 Drawing Sheets

Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,432,272 A | 1/1995 | Benner |
| 5,434,257 A | 1/1995 | Matteucci et al. |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,536,821 A | 1/1996 | Agrawal et al. |
| 5,539,082 A | 1/1996 | Nielsen et al. |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van et al. |
| 5,519,126 A | 5/1996 | Hecht |
| 5,525,465 A | 6/1996 | Haralambidis et al. |
| 5,525,711 A | 6/1996 | Hawkins et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,786,211 A | 1/1998 | Johnson |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 5,871,982 A | 2/1999 | Wilson et al. |
| 6,005,096 A | 12/1999 | Matteucci et al. |
| 6,258,595 B1 | 7/2001 | Gao et al. |
| 6,287,860 B1 | 9/2001 | Monia et al. |
| 2003/0158403 A1 | 8/2003 | Manoharan et al. |
| 2014/0068797 A1 | 3/2014 | Doudna et al. |
| 2016/0067228 A1 | 3/2016 | Kishimoto |

FOREIGN PATENT DOCUMENTS

| | | |
|---|---|---|
| WO | WO1995/013392 | 5/1995 |
| WO | WO1996/017947 | 6/1996 |
| WO | WO1997/006243 | 2/1997 |
| WO | WO1997/008298 | 3/1997 |
| WO | WO1997/009441 | 3/1997 |
| WO | WO1997/021825 | 6/1997 |
| WO | WO1999/011764 | 3/1999 |
| WO | WO2001/083692 | 11/2001 |
| WO | WO2013/176772 | 11/2013 |
| WO | WO2014/071219 | 5/2014 |
| WO | WO2015/048577 | 4/2015 |
| WO | WO2015/089419 | 6/2015 |

OTHER PUBLICATIONS

Bartel, "MicroRNAs: target recognition and regulatory functions," Cell 2009, 136, 215-233.

Behlke, "Chemical modification of siRNAs for in vivo use," Oligonucleotides 2008, 18(4), 305-319.

Belfort et al., "Homing endonucleases: from genetic anomalies to programmable genomic clippers," Methods in Molecular Biology 2014, 1123, in 26 pages.

Boch, "Breaking the code of DNA binding specificity of TAL-type III effectors," Science 2009, 326(5959), 1509-1512.

Boissel et al., "Assembly and characterization of megaTALs for hyper specific genome engineering applications," Methods Mol. Biol. 2015, 1239, 171-196.

Boissel et al., "MegaTALs: a rare-cleaving nuclease architecture for therapeutic genome engineering," Nucleic Acids Res. 2014, 42, 2591-2601.

Braasch et al., "Novel antisense and peptide nucleic acid strategies for controlling gene expression," Biochemistry 2002, 41(14), 4503-4510.

Bramsen et al., "Development of therapeutic-grade small interfering RNAs by chemical engineering," Front Genet. 2012, 3, 154.

Brinkman et al., "Easy quantitative assessment of genome editing by sequence trace decomposition," Nucleic Acids Research 2014, 42(22), in 8 pages.

Budniatzky et al., "Concise review: reprogramming strategies for cardiovascular regenerative medicine: from induced pluripotent stem cells to direct reprogramming," Stem Cells Transl. Med. 2014, 3(4), 448-457.

Burnett et al., "Current progress of siRNA/shRNA therapeutics in clinical trials," Biotechnol J. 2011, 6(9), 1130-1146.

Canver et al., "BCL11A enhancer dissection by Cas9-mediated in situ saturating mutagenesis," Nature 2015, 527(7577), 192-197.

Carter, "Adeno-associated virus vectors," Curr. Opin. Biotechnol. 1992, 3(5), 1533-539.

Cekaite et al., "Gene expression analysis in blood cells in response to unmodified and 2'-modified siRNAs reveals TLR-dependent and independent effects," Journal of Molecular Biology 2007, 365, 90-108.

(56) References Cited

OTHER PUBLICATIONS

Cermak et al., Efficient design and assembly of custom TALEN and other TAL effector-based constructs for DNA targeting, Nucleic Acids Res. 2011, 39(12), in 11 pages.
Cermak et al., "Efficient design and assembly of custom TALENs using the Golden Gate platform," Methods Mol. Biol. 2015, 1239, 133-159.
Chen et al., "Global microRNA depletion suppresses tumor angiogenesis," Genes Dev. 2014, 28, 1054-1067.
Chernolovskaya et al., "Chemical modification of siRNA," Curr. Opin. Mol. Ther. 2010, 12(2), 158-167.
Chu et al., "Increasing the efficiency of homology-directed repair for CRISPR-Cas9-induced precise gene editing in mammalian cells," Nat. Bio. 2015, 33(5), 543-548.
Clark et al., "A stable cell line carrying adenovirus-inducible rep and cap genes allows for infectivity titration of adeno-associated virus vectors," Gene Ther. 1996, 3, 1124-1132.
Communication pursuant to Article 94(3) EPC dated Mar. 31, 2021 in European Patent Application No. 17716986.9.
Communication pursuant to Article 94(3) EPC dated May 11, 2020 in European Patent Application No. 17716986.9.
Communication pursuant to Article 94(3) EPC dated Oct. 21, 2021 in European Patent Application No. 17716986.9.
Communication under Rule 71(3) EPC dated Jul. 21, 2022 in European Patent Application No. 17716986.9.
Crooke et al., "Pharmacokinetic properties of several novel oligonucleotide analogs in mice," J. Pharmacol. Exp. Ther. 1996, 277, 923-937.
Database Embl [Online], "H. sapiens HFE gene, exon 2 & 3," European Nucleotide Archive 1997, in 2 page.
Database Embl [Online], "Human hereditary haemochromatosis protein (HLA-H) gene, partial cds," European Nucleotide Archive 1999, in 2 page.
De Mesmaeker et al., "Antisense oligonucleotides," Accounts of Chemical Research 1995, 28(9), 366-374.
De Mesmaeker et al., "Antisense Oligonucleotides," Ace. Chem. Res. 1995, 28, 366-374.
Decision to grant a European patent pursuant to Article 97(1) EPC dated Dec. 8, 2022 in European Patent Application No. 17716986.9.
Deleavey et al., "Chemical modification of siRNA," Current Protocols in Nucleic Acid Chemistry 2009, 39(1), in 22 pages.
Deltcheva et al., "CRISPR RNA maturation by trans-encoded small RNA and host factor RNase III," Nature 2011, 471(7340), 602-607.
Dreier et al., "Development of zinc finger domains for recognition of the 5'-CNN-3' family DNA sequences and their use in the construction of artificial transcription factors," Journal of Biological Chemistry 2005, 280(42), 35588-35597.
Dreier et al., "Development of zinc finger domains for recognition of the 5'-ANN-3' family of DNA sequences and their use in the construction of artificial transcription factors," Journal of Biological Chemistry 2001, 276(31), 29466-29478.
Duan et al., "Differentiation and characterization of metabolically functioning hepatocytes from human embryonic stem cells," Stem Cells 2010, 28(4), 674-686.
Englisch & Gauss, "Chemically modified oligonucleotides as probes and inhibitors," Angewandte Chemie International Edition in English 1991, 30(6), 613-629.
Ezquer et al., "Hereditary hemochromatosis: An opportunity for gene therapy," Biol Res. 2006, 39(1), 113-124.
Flotte et al., "Gene expression from adeno-associated virus vectors in airway epithelial cells," Am. J. Respir. Cell Mol. Biol. 1992, 7, 349-356.
Focosi et al., "Induced pluripotent stem cells in hematology: current and future applications," Blood Cancer Journal 2014, 4(5), in 8 pages.
Fonfara et al., "Phylogeny of Cas9 determines functional exchangeability of dual-RNA and Cas9 among orthologous type II CRISPR-Cas systems," Nucleic Acids Research 2014, 42(4), 2577-2590.
Fucini et al., "Adenosine modification may be preferred for reducing siRNA immune stimulation," Nucleic Acid Therapeutics 2012, 22(3), 205-210.
Gaglione & Messere, "Recent progress in chemically modified siRNAs," Mini Reviews in Medicinal Chemistry 2010, 10(7), 578-595.
Gebeyehu et al., "Novel biotinylated nucleotide-analogs for labeling and colorimetric detection of DNA," Nucleic Acids Research 1987, 15(11), 4513-4534.
Goeddel, Gene Expression Technology: Methods in Enzymology 1990, 185, in 681 pages.
Graham et al., Resources for the design of CRISPR gene editing experiments, Genome Biology 2015, 16(1), in 21 pages.
Guilinger et al., "Fusion of catalytically inactive Cas9 to FokI nuclease improves the specificity of genome modification," Nature Biotechnology 2014, 32(6), 577-582.
Hafez & Hausner, "Homing endonucleases: DNA scissors on a mission," Genome 2012, 55(8), 553- 569.
Heasman, "Morpholino oligos: making sense of antisense?," Developmental Biology 2002, 243(2), 209-214.
Hermonat & Muzyczka, "Use of adeno-associated virus as a mammalian DNA cloning vector: transduction of neomycin resistance into mammalian tissue culture cells," Proceedings of the National Academy of Sciences 1984, 81(20), 6466-6470.
Herranz & Cohen, "MicroRNAs and gene regulatory networks: managing the impact of noise in biological systems," Genes & Development 2010, 24(13), 1339-1344.
Herrera et al., "Isolation and characterization of a stem cell population from adult human liver," Stem Cells 2006, 24(12), 2840-2850.
Hu et al., "Physiological roles of asialoglycoprotein receptors (ASGPRs) variants and recent advances in hepatic-targeted delivery of therapeutic molecules via ASGPRs," Protein and Peptide Letters 2014, 21(10), 1025-1030.
Huangfu et al., "Induction of pluripotent stem cells by defined factors is greatly improved by small-molecule compounds," Nature Biotechnology 2008, 26(7), 795-797.
International Preliminary Report on Patentability dated Sep. 27, 2018 in International Application No. PCT/IB2017/000317.
International Search Report and Written Opinion dated Jun. 30, 2017 in International Application No. PCT/IB2017/000317.
Jinek et al., "A programmable dual-RNA-guided DNA endonuclease in adaptive bacterial immunity," Science 2012, 337(6096), 816-821.
Judge & MacLachlan, "Overcoming the innate immune response to small interfering RNA," Human Gene Therapy 2008, 19(2), 111-124.
Judge et al., "Design of noninflammatory synthetic siRNA mediating potent gene silencing in vivo," Molecular Therapy 2006, 13(3), 494-505.
Kabanov et al., "A new class of antivirals: antisense oligonucleotides combined with a hydrophobic substituent effectively inhibit influenza virus reproduction and synthesis of virus-specific proteins in MDCK cells," FEBS letters 1990, 259(2), 327-330.
Kanasty et al., "Action and reaction: the biological response to siRNA and its delivery vehicles," Molecular Therapy 2012, 20(3), 513-524.
Karikó et al., "Suppression of RNA recognition by Toll-like receptors: the impact of nucleoside modification and the evolutionary origin of RNA," Immunity 2005, 23(2), 165-175.
Kleinstiver et al., "The I-TevI nuclease and linker domains contribute to the specificity of monomeric TALENs," G3: Genes, Genomes, Genetics 2014, 4(6) 1155-1165.
Kole et al., "RNA therapeutics: beyond RNA interference and antisense oligonucleotides," Nature Reviews Drug Discovery 2012, 11(2), 125-140.
Kormann et al., "Expression of therapeutic proteins after delivery of chemically modified mRNA in mice," Nature biotechnology 2011, 29(2), 154-157.
Kornberg, "Dna Replication," W. H. Freeman & Co., San Francisco 1980, 75-77.
Lacerra et al., "Restoration of hemoglobin A synthesis in erythroid cells from peripheral blood of thalassemic patients," Proceedings of the National Academy of Sciences 2000, 97(17), 9591-9596.

(56) References Cited

OTHER PUBLICATIONS

Laughlin et al., "Cloning of infectious adeno-associated virus genomes in bacterial plasmids," Gene 1983, 23(1), 65-73.
Lebkowski et al., "Adena-Associated Virus: a Vector System for Efficient Introduction and Integration of DNA into a Variety of Mammalian Cell Types," Mol. Cell. Biol. 1988, 8, 3988-3996.
Anonymous, "Headlines: Genome Editing Technology Promises New Ways to Treat Diseases," 21st Century Tech 2013, in 3 pages. http://www.21stcentech.com/headlines-genome-editing-technology-promises-ways-treat-diseases/.
Letsinger et al., "Cholesteryl-conjugated oligonucleotides: synthesis, properties, and activity as inhibitors of replication of human immunodeficiency virus in cell culture," Proceedings of the National Academy of Sciences 1989, 86(17), 6553-6556.
Li et al., "Modularly assembled designer TAL effector nucleases for targeted gene knockout and gene replacement in eukaryotes," Nucleic Acids Research 2011, 39(14), 6315-6325.
Liu et al., "Validated zinc finger protein designs for all 16 GNN DNA triplet targets," Journal of Biological Chemistry 2002, 277(6), 3850-3856.
Ma et al., "Highly efficient differentiation of functional hepatocytes from human induced pluripotent stem cells," Stem Cells Translational Medicine 2013, 2(6), 409-419.
Ma et al., "Pol III promoters to express small RNAs: delineation of transcription initiation," Molecular Therapy-Nucleic Acids 2014, 3, in 11 pages.
Maherali & Hochedlinger, "Guidelines and techniques for the generation of induced pluripotent stem cells," Cell Stem Cell 2008, 3(6), 595-605.
Mak et al., "The crystal structure of TAL effector PthXo1 bound to its DNA target," Science 2012, 335(6069), 716-719.
Manoharan et al., "Chemical modifications to improve uptake and bioavailability of antisense oligonucleotides," Annals of the New York Academy of Sciences 1992, 660(1), 306-309.
Manoharan et al., "Cholic acid-oligonucleotide conjugates for antisense applications," Bioorganic & Medicinal Chemistry Letters 1994, 4(8), 1053-1060.
Manoharan et al., "Introduction of a lipophilic thioether tether in the minor groove of nucleic acids for antisense applications," Bioorganic & Medicinal Chemistry Letters 1993, 3(12), 2765-2770.
Manoharan et al., "Lipidic nucleic acids," Tetrahedron Letters 1995, 36(21), 3651-3654.
Manoharan et al., "Oligonucleotide conjugates: alteration of the pharmacokinetic properties of antisense agents," Nucleosides, Nucleotides & Nucleic Acids 1995, 14(3-5), 969-973.
Maresca et al., "Obligate ligation-gated recombination (ObLiGaRe): custom-designed nuclease-mediated targeted integration through nonhomologous end joining," Genome Research 2013, 23(3), 539-546.
Marson et al., "Wnt signaling promotes reprogramming of somatic cells to pluripotency," Cell Stem Cell 2008, 3(2), 132-135.
Martin, "Ein Neuer Zugang Zu 2'-O-Alkylribonucleosiden Und Eigenschaften Deren Oligonucleotide," Helvetica Chimica Acta 1995, 78(2), 486-504.
Mclaughlin et al., "Adeno-associated virus general transduction vectors: analysis of proviral structures," Journal of Virology 1988, 62(6), 1963-1973.
Mishra et al., "Improved leishmanicidal effect of phosphorotioate antisense oligonucleotides by LDL-mediated delivery," Biochimica et Biophysica Acta (BBA)-Gene Structure and Expression 1995, 1264(2), 229-237.
Montosi et al., "Wild-type HFE protein normalizes transferrin iron accumulation in macrophages from subjects with hereditary hemochromatosis," Blood 2000, 96(3), 1125-1129.
Moscou & Bogdanove, "A simple cipher governs DNA recognition by TAL effectors," Science 2009, 326(5959), 1501-1501.
Muzyczka, "Use of adeno-associated virus as a general transduction vector for mammalian cells," Viral Expression Vectors 1992, 97-129.
Nasevicius & Ekker, "Effective targeted gene 'knockdown' in zebrafish," Nature Genetics 2000, 26(2), 216-220.

Nielsen et al., "Sequence-selective recognition of DNA by strand displacement with a thymine-substituted polyamide," Science 1991, 254(5037), 1497-1500.
Notice of Allowance dated Apr. 1, 2021 in U.S. Appl. No. 16/084,531.
Oberhauser & Wagner, "Effective incorporation of 2'-O-methyl-oligoribonuclectides into liposomes and enhanced cell association through modification with thiocholesterol," Nucleic Acids Research 1992, 20(3), 533-538.
Paul et al., "Increased viral titer through concentration of viral harvests from retroviral packaging lines," Human Gene Therapy 1993, 4(5), 609-615.
Paulk et al., "In vivo selection of transplanted hepatocytes by pharmacological inhibition of fumarylacetoacetate hydrolase in wild-type mice," Molecular Therapy 2012, 20(10), 1981-1987.
Peer & Lieberman, "Special delivery: targeted therapy with small RNAs," Gene Therapy 2011, 18(12), 1127-1133.
Peng et al., "Potential pitfalls of CRISPR/Cas9-mediated genome editing," The FEBS Journal 2015, 283(7), 1218-1231.
Perrin et al., "An experimental rabies vaccine produced with a new BHK-21 suspension cell culture process: use of serum-free medium and perfusion-reactor system," Vaccine 1995, 13(13), 1244-1250.
Pittenger et al., "Multilineage potential of adult human mesenchymal stem cells," Science 1999, 284(5411), 143-147.
Posadas & Carthew, "MicroRNAs and their roles in developmental canalization," Current Opinion in Genetics & Development 2014, 27, 1-6.
Restriction Requirement dated Nov. 16, 2020 in U.S. Appl. No. 16/084,531.
Saj & Lai, "Control of microRNA biogenesis and transcription by cell signaling pathways," Current Opinion in Genetics & Development 2011, 21(4), 504-510.
Samulski et al., "Cloning of adeno-associated virus into pBR322: rescue of intact virus from the recombinant plasmid in human cells," Proceedings of the National Academy of Sciences 1982, 79(6), 2077-2081.
Samulski et al., "Helper-free stocks of recombinant adeno-associated viruses: normal integration does not require viral gene expression," Journal of Virology 1989, 63(9), 3822-3828.
Sanghvi, "Heterocyclic base modifications in nucleic acids and their applications in antisense oligonucleotides," In: Crooke ST, Lebleu B (eds) Antisense research and applications. CRC Press, Boca Raton 1993, 289-302.
Sanghvi, "Heterocyclic base modifications in nucleic acids and their applications in antisense oligonucleotides," In: Crooke ST, Lebleu B (eds) Antisense research and applications. CRC Press, Boca Raton 1993, 276-278.
Sapranauskas et al., "The Streptococcus thermophilus CRISPR/Cas system provides immunity in *Escherichia coli*," Nucleic Acids Research 2011, 39(21), 9275-9282.
Sawitza et al., "Bile acids induce hepatic differentiation of mesenchymal stem cells," Scientific Reports 2015, 5(1), in 15 pages.
Segal et al., "Toward controlling gene expression at will: selection and design of zinc finger domains recognizing each of the 5'-GNN-3' Dna target sequences," Proceedings of the National Academy of Sciences 1999, 96(6), 2758-2763.
Senapathy & Carter, "Molecular cloning of adeno-associated virus variant genomes and generation of infectious virus by recombination in mammalian cells," Journal of Biological Chemistry 1984, 259(7), 4661-4666.
Shea et al., "Synthesis, hybridization properties and antiviral activity of lipid-oligodeoxynucleotide conjugates," Nucleic Acids Research 1990, 18(13), 3777-3783.
Shi et al., "A combined chemical and genetic approach for the generation of induced pluripotent stem cells," Cell Stem Cell 2008, 2(6), 525-528.
Soutschek et al., "Therapeutic silencing of an endogenous gene by systemic administration of modified siRNAs," Nature 2004, 432(7014), 173-178.
Steentoft et al., "Precision genome editing: a small revolution for glycobiology," Glycobiology 2014, 24(8), 663-680.
Stern-Ginossar et al., "Host immune system gene targeting by a viral miRNA," Science 2007, 317(5836), 376-381.

(56) References Cited

OTHER PUBLICATIONS

Svinarchuk et al., "Inhibition of HIV proliferation in MT-4 cells by antisense oligonucleotide conjugated to lipophilic groups," Biochimie 1993, 75(1-2), 49-54.
Takahashi & Yamanaka, "Induction of pluripotent stem cells from mouse embryonic and adult fibroblast cultures by defined factors," Cell 2006, 126(4), 663-676.
Takahashi et al., "Induction of pluripotent stem cells from adult human fibroblasts by defined factors," Cell 2007, 131(5), 861-872.
Tratschin et al., "A human parvovirus, adeno-associated virus, as a eucaryotic vector: transient expression and encapsidation of the procaryotic gene for chloramphenicol acetyltransferase," Molecular and Cellular Biology 1984, 4(10), 2072-2081.
Tratschin et al., "Adeno-associated virus vector for high-frequency integration, expression, and rescue of genes in mammalian cells," Molecular and Cellular Biology 1985, 5(11), 3251-3260.
Tsai et al., "Dimeric CRISPR RNA-guided FokI nucleases for highly specific genome editing," Nature Biotechnology 2014, 32(6), 569-576.
Volkov et al., "Selective protection of nuclease-sensitive sites in siRNA prolongs silencing effect," Oligonucleotides 2009, 19(2), 191-202.
Wang et al., "Cyclohexene nucleic acids (CeNA): serum stable oligonucleotides that activate RNase H and increase duplex stability with complementary RNA," Journal of the American Chemical Society 2000, 122(36), 8595-8602.
Wang et al., "Rapid and efficient assembly of transcription activator-like effector genes by USER cloning," Journal of Genetics and Genomics 2014, 41(6), 339-347.
Warren et al., "Highly efficient reprogramming to pluripotency and directed differentiation of human cells with synthetic modified mRNA," Cell Stem Cell 2010, 7(5), 618-630.
Weber et al., "Methylation of human microRNA genes in normal and neoplastic cells," Cell Cycle 2007, 6(9), 1001-1005.
Whitehead et al., "Silencing or stimulation? siRNA delivery and the immune system," Annual Review of Chemical and Biomolecular Engineering 2011, 2, 77-96.
Winkler, "Oligonucleotide conjugates for therapeutic applications," Therapeutic Delivery 2013, 4(7), 791-809.
Wolfs et al., "MegaTevs: single-chain dual nucleases for efficient gene disruption," Nucleic Acids Research 2014, 42(13), 8816-8829.
Zhao et al., "Sequence-specific inhibition of microRNA via CRISPR/CRISPRi system," Scientific Reports 2014, 4(1), in 5 pages.

\* cited by examiner

Fig. 2A

| SEQ ID NO. | Name | Guide sequence | Indel | R2 |
|---|---|---|---|---|
| 3610 | Hfe_T168 | CCCAAGGACCAAATGATCTC | 87.8 | 0.9424 |
| 973 | Hfe_T303 | TCTCTGCACTACCTCTTCAT | 84.2 | 0.9302 |
| 378 | Hfe_T101 | GAGCCTAGGCAATAGCTGTA | 81.8 | 0.9935 |
| 1029 | Hfe_T386 | CTGGAAGTCTGAGGTCTTGT | 81.1 | 0.9646 |
| 3598 | Hfe_T450 | ACAGCCCAGGATGACCTGCA | 80.8 | 0.9891 |
| 3634 | Hfe_T552 | GAAATTCTACTGGAAACCCA | 80.6 | 0.9161 |
| 1142 | Hfe_T418 | ATCCCTGGTTGGAGTTTCAG | 77.4 | 0.9757 |
| 388 | Hfe_T18 | GGAGATTTAACGGGGACGTG | 75.8 | 0.9711 |
| 1121 | Hfe_T342 | AGAGGTGTTTTGGACCAACA | 75.4 | 0.9755 |
| 3678 | Hfe_T131 | CTCATACCATCAGCTGTGTC | 74 | 0.9497 |
| 1137 | Hfe_T210 | GTTGCAGGGCACGGAATCCC | 72 | 0.9835 |
| 3531 | Hfe_T322 | TTCCCTTTGAGCCATATGCA | 72 | 0.987 |
| 3654 | Hfe_T448 | GCTCTGAGGCACCCATGAAG | 71.9 | 0.8865 |
| 1045 | Hfe_T446 | GATCATTTGGTCCTTGGGGA | 71.9 | 0.8994 |
| 1096 | Hfe_T528 | GTGGGAAAGGCACAAGATTC | 71.2 | 0.95 |
| 3558 | Hfe_T120 | ACTCTGCCACTAGAGTATAG | 71.2 | 0.987 |
| 3585 | Hfe_T404 | CTCTCCAATCCAGTGTGTCA | 70.4 | 0.9483 |
| 1102 | Hfe_T318 | GATTCGGGCCAGGCAGAACA | 68.8 | 0.9597 |
| 1028 | Hfe_T429 | GCTGGAAGTCTGAGGTCTTG | 68.2 | 0.926 |
| 3552 | Hfe_T327 | CACCTCTGAAACTCCAACCA | 68.1 | 0.9655 |
| 3604 | Hfe_T232 | GCCTTGTTAACTGCAACCAA | 67.1 | 0.9584 |
| 1067 | Hfe_T48 | GCAAGAAGACAACAGTACCG | 67 | 0.9869 |
| 1071 | Hfe_T89 | ACCGAGGGCTACTGGAAGTA | 66.6 | 0.9729 |
| 3389 | Hfe_T174 | CAAGGTTATCCAGCCCTGGT | 66.6 | 0.929 |
| 1128 | Hfe_T355 | CCTATACTCTAGTGGCAGAG | 66.4 | 0.9802 |
| 1033 | Hfe_T636 | TCTGAGGTCTTGTGGGAGCA | 66.1 | 0.95 |
| 1158 | Hfe_T294 | ATGAGACAGCCACAAGTCAT | 65.3 | 0.9659 |
| 401 | Hfe_T118 | CCTGATGCTTTTGCAGACCG | 63.1 | 0.9016 |
| 1074 | Hfe_T23 | ACTGGAAGTACGGGTATGAT | 63 | 0.9888 |
| 3556 | Hfe_T205 | CCACTCTGCCACTAGAGTAT | 62.4 | 0.9433 |
| 1053 | Hfe_T376 | TCCTTTGGTTGCAGTTAACA | 62.2 | 0.9786 |
| 1125 | Hfe_T98 | CTTCTGCCCCTATACTCTAG | 62.1 | 0.9535 |
| 1164 | Hfe_T361 | GGCTCAAAGGGAAGTGTCTA | 61.2 | 0.9765 |
| 419 | Hfe_T113 | GGCGAACTAGGGGCGCGGCG | 60.5 | 0.9172 |
| 1103 | Hfe_T313 | CAGGCAGAACAGGGCCTACC | 58.7 | 0.97 |
| 1062 | Hfe_T396 | CACACCCTGCAGGTCATCCT | 57.6 | 0.8972 |
| 969 | Hfe_T207 | CCTCCTACTACACATGGTTA | 57 | 0.8523 |
| 3646 | Hfe_T281 | GTAGCCCAAAGCTTCAAACA | 56.9 | 0.9661 |
| 1077 | Hfe_T521 | TGAATTCTGCCCTGACACAC | 55.5 | 0.9609 |
| 3417 | Hfe_T93 | CACCAAAGGAGGCACTTGAC | 55.5 | 0.9631 |
| 1258 | Hfe_T92 | CTGTGTTAGAGTCCAATCTT | 54.6 | 0.9603 |
| 982 | Hfe_T44 | GTTTGAAGCTTTGGGCTACG | 54.4 | 0.9355 |
| 3592 | Hfe_T144 | CCCGTACTTCCAGTAGCCCT | 54 | 0.969 |

Fig. 2B

| | | | | |
|---|---|---|---|---|
| 1297 | Hfe_T133 | TAAAGACGTATTGCCCAATG | 53.6 | 0.921515 |
| 1049 | Hfe_T553 | CCTTGGGGATGGTGGAAATA | 53.3 | 0.867 |
| 3584 | Hfe_T211 | GCTCTCCAATCCAGTGTGTC | 53.1 | 0.9729 |
| 404 | Hfe_T34 | TTGCAGACCGCGGTCCTGCA | 52.5 | 0.9849 |
| 3624 | Hfe_T374 | CTCTCCACGTACCCTTGCTG | 51.2 | 0.931235 |
| 4100 | Hfe_T402 | AAATCTCCGCTTCTTTTGGG | 50 | 0.9745 |
| 988 | Hfe_T106 | GTGTGGAGCCCGAACTCCA | 49.4 | 0.8118 |
| 3671 | Hfe_T352 | TTAACCATGTGTAGTAGGAG | 48.5 | 0.958 |
| 418 | Hfe_T122 | GGGCGAACTAGGGGCGCGGC | 48.3 | 0.9544 |
| 1266 | Hfe_T193 | TCCTTCCTCCAACCTATAGA | 48.3 | 0.9701 |
| 3394 | Hfe_T186 | GTCTTTAGGTTCGAACTCCT | 47.9 | 0.94095 |
| 1091 | Hfe_T375 | CTGGCCCACCAAGCTGGAGT | 47.3 | 0.9541 |
| 1050 | Hfe_T216 | GAAATAGGGACCTATTCCTT | 47.2 | 0.9693 |
| 1305 | Hfe_T85 | ATAACCTTGGCTGTACCCCC | 45.4 | 0.9204 |
| 3573 | Hfe_T405 | CAGGTAGGCCCTGTTCTGCC | 44.8 | 0.98 |
| 3669 | Hfe_T171 | CCTTAACCATGTGTAGTAGG | 44.3 | 0.6955 |
| 3561 | Hfe_T82 | GTGTTTCCACCATACCTTGT | 44.3 | 0.9722 |
| 3557 | Hfe_T111 | CACTCTGCCACTAGAGTATA | 43.9 | 0.9821 |
| 3670 | Hfe_T233 | CTTAACCATGTGTAGTAGGA | 43.7 | 0.7979 |
| 4082 | Hfe_T152 | CAAGCGCCCCTGCAGGACCG | 43.5 | 0.9762 |
| 964 | Hfe_T132 | CTGATGGTATGAGTTGATGC | 43.1 | 0.9767 |
| 1068 | Hfe_T175 | CAAGAAGACAACAGTACCGA | 42.4 | 0.9767 |
| 1302 | Hfe_T125 | AATGGGGATGGGACCTACCA | 42.4 | 0.7329 |
| 1304 | Hfe_T134 | CTACCAGGGCTGGATAACCT | 41.8 | 0.9301 |
| 4112 | Hfe_T240 | TCACCCTACAGCTATTGCCT | 41 | 0.89 |
| 3638 | Hfe_T91 | CTGGAAACCCATGGAGTTCG | 41 | 0.9804 |
| 3621 | Hfe_T411 | AAGCTCTGACAACCTCAGGA | 40.9 | 0.9218 |
| 1072 | Hfe_T50 | CCGAGGGCTACTGGAAGTAC | 40.2 | 0.6684 |
| 377 | Hfe_T252 | TGAGCCTAGGCAATAGCTGT | 40.1 | 0.9425 |
| 3639 | Hfe_T151 | ATGGAGTTCGGGGCTCCACA | 39.8 | 0.88 |
| 1301 | Hfe_T801 | CAATGGGGATGGGACCTACC | 39.4 | 0.6802 |
| 1044 | Hfe_T346 | CTGAGATCATTTGGTCCTTG | 38.9 | 0.9744 |
| 1084 | Hfe_T531 | ATTGGAGAGCAGCAGAACCC | 38.8 | 0.9713 |
| 3382 | Hfe_T829 | TATCTGCTCTTCCCCAGG | 37.7 | 0.7093 |
| 3577 | Hfe_T508 | CTTTCCCACTCCAGCTTGGT | 36.4 | 0.9467 |
| 3381 | Hfe_T731 | ATATCTCTGCTCTTCCCCAG | 36.2 | 0.893 |
| 1123 | Hfe_T299 | TTTGGACCAACAAGGTATGG | 36 | 0.9765 |
| 3572 | Hfe_T493 | AGGGCAGTCCCTCTCCAGGT | 35.7 | 0.9646 |
| 1306 | Hfe_T155 | TAACCTTGGCTGTACCCCCT | 35.7 | 0.9735 |
| 3438 | Hfe_T235 | CACTTCCTTCTATAGGTTGG | 34.5 | 0.9751 |
| 989 | Hfe_T33 | TGTGGAGCCCGAACTCCAT | 34.3 | 0.9707 |
| 1073 | Hfe_T57 | TACTGGAAGTACGGGTATGA | 33.6 | 0.9811 |
| 3391 | Hfe_T366 | TGGTAGGTCCCATCCCCATT | 33.2 | 0.9 |
| 1078 | Hfe_T206 | TCTGCCCTGACACACTGGAT | 32.9 | 0.978 |
| 1015 | Hfe_T687 | CAGCAAGGGTACGTGGAGAG | 32.8 | 0.988247 |
| 387 | Hfe_T88 | AAAGAAGCGGAGATTTAACG | 32.5 | 0.9703 |

Fig. 2C

| 1056 | Hfe_T329 | GGTTGCAGTTAACAAGGCTG | 32.5 | 0.9843 |
|---|---|---|---|---|
| 3651 | Hfe_T667 | AAGACCAAGGTCCTGCTCTG | 31.2 | 0.9779 |
| 1032 | Hfe_T441 | GTCTGAGGTCTTGTGGGAGC | 29.9 | 0.9606 |
| 1043 | Hfe_T290 | CCTGAGATCATTTGGTCCTT | 29.5 | 0.9851 |
| 3395 | Hfe_T198 | TCGAACTCCTTGGCATCCAT | 29.5 | 0.888574 |
| 3667 | Hfe_T59 | AGGCCTTAACCATGTGTAGT | 29.3 | 0.9848 |
| 981 | Hfe_T740 | CTTTCCTTGTTTGAAGCTTT | 28.7 | 0.9881 |
| 972 | Hfe_T547 | CTCTCTGCACTACCTCTTCA | 27.2 | 0.9813 |
| 409 | Hfe_T5 | CGCTTGCTGCGTGAGTCCGA | 27.1 | 0.9692 |
| 4117 | Hfe_T338 | AGATGCCCAGTAAAACTTCC | 27.1 | 0.9784 |
| 977 | Hfe_T458 | CTTCATGGGTGCCTCAGAGC | 26.3 | 0.9734 |
| 1298 | Hfe_T87 | GACGTATTGCCCAATGGGGA | 26 | 0.9275 |
| 1307 | Hfe_T242 | AACCTTGGCTGTACCCCCTG | 25.8 | 0.9403 |
| 386 | Hfe_T238 | AAAAGAAGCGGAGATTTAAC | 25.6 | 0.9817 |
| 1122 | Hfe_T104 | TGTTTTGGACCAACAAGGTA | 25.6 | 0.9848 |
| 3636 | Hfe_T234 | TACTGGAAACCCATGGAGTT | 25.2 | 0.9859 |
| 1161 | Hfe_T204 | TCTCCATGCATATGGCTCAA | 25.1 | 0.9901 |
| 3637 | Hfe_T388 | ACTGGAAACCCATGGAGTTC | 25 | 0.9768 |
| 408 | Hfe_T11 | GCGCTTGCTGCGTGAGTCCG | 24.9 | 0.9789 |
| 1101 | Hfe_T277 | AGATTCGGGCCAGGCAGAAC | 24.8 | 0.9752 |
| 3659 | Hfe_T385 | TAGTGCAGAGAGTGTGAACC | 24.5 | 0.9784 |
| 1000 | Hfe_T694 | CAGCTGAGTCAGAGTCTGAA | 24.4 | 0.9765 |
| 1010 | Hfe_T608 | ACAACCACAGCAAGGGTACG | 23.8 | 0.983922 |
| 3632 | Hfe_T494 | GACTCAGCTGCAGCCACATC | 23 | 0.9874 |
| 986 | Hfe_T4 | TGATGATGAGAGTCGCCGTG | 21.2 | 0.982672 |
| 1303 | Hfe_T324 | GGGATGGGACCTACCAGGGC | 21 | 0.8973 |
| 1014 | Hfe_T721 | ACAGCAAGGGTACGTGGAGA | 20.9 | 0.984502 |
| 1002 | Hfe_T762 | TGAGTCAGAGTCTGAAAGGG | 20.7 | 0.9824 |
| 1069 | Hfe_T84 | ACAACAGTACCGAGGGCTAC | 20.6 | 0.9906 |
| 1003 | Hfe_T579 | GAGTCAGAGTCTGAAAGGGT | 20.3 | 0.9881 |
| 3642 | Hfe_T102 | CATCATAGAACACGAACAGC | 16.6 | 0.986739 |
| 3633 | Hfe_T372 | CATCTGGCTTGAAATTCTAC | 16 | 0.9752 |
| 1296 | Hfe_T36 | CTAAAGACGTATTGCCCAAT | 15.5 | 0.982383 |
| 4099 | Hfe_T285 | TAAATCTCCGCTTCTTTTGG | 13.5 | 0.9745 |
| 379 | Hfe_T158 | AATAGCTGTAGGGTGACTTC | 13.1 | 0.9711 |
| 1054 | Hfe_T188 | TTGGTTGCAGTTAACAAGGC | 12.1 | 0.991 |
| 4106 | Hfe_T377 | TTTTGGGGGGCGGGGAAACG | 11.9 | 0.9857 |
| 417 | Hfe_T68 | CGGGCGAACTAGGGGCGCGG | 11.6 | 0.9755 |
| 3448 | Hfe_T224 | ACCATTTTGTGTCCTAAGAT | 11.2 | 0.9896 |
| 1076 | Hfe_T66 | GAAGTACGGGTATGATGGGC | 10.9 | 0.9931 |
| 4091 | Hfe_T239 | CAGGAGGAGAAGCGCCGGCC | 10.6 | 0.9673 |
| 1299 | Hfe_T45 | ACGTATTGCCCAATGGGGAT | 10 | 0.8588 |
| 1098 | Hfe_T179 | AAAGGCACAAGATTCGGGCC | 9.3 | 0.99 |
| 1138 | Hfe_T112 | CAGGGCACGGAATCCCTGGT | 9.3 | 0.9924 |
| 3431 | Hfe_T83 | GGGATCTGTTTACCCTTGCC | 9.1 | 0.9914 |
| 428 | Hfe_T264 | TGGGAGTTTGCTAACTTTGG | 9 | 0.9745 |

Fig. 2D

| 3390 | Hfe_T167 | CTGGTAGGTCCCATCCCCAT | 8.8 | 0.9509 |
|---|---|---|---|---|
| 4092 | Hfe_T100 | AGAAGCGCCGGCCTGGCTCG | 8.6 | 0.9814 |
| 1041 | Hfe_T658 | ATTTGCTTCCTGAGATCATT | 8.1 | 0.9779 |
| 3385 | Hfe_T331 | TTCCCCAGGGGGTACAGCCA | 8.1 | 0.9394 |
| 4077 | Hfe_T61 | CCTAGTTCGCCCGCAGCCCT | 6.9 | 0.9816 |
| 3387 | Hfe_T140 | CAGCCAAGGTTATCCAGCCC | 6.6 | 0.9707 |
| 4098 | Hfe_T398 | TTAAATCTCCGCTTCTTTTG | 6.4 | 0.993 |
| 403 | Hfe_T27 | TTTGCAGACCGCGGTCCTGC | 6.3 | 0.9882 |
| 1162 | Hfe_T231 | CTCCATGCATATGGCTCAAA | 5.5 | 0.991 |
| 1295 | Hfe_T41 | CCTAAAGACGTATTGCCCAA | 5.2 | 0.973203 |
| 405 | Hfe_T146 | TGCAGACCGCGGTCCTGCAG | 5 | 0.984 |
| 978 | Hfe_T622 | GGTGCCTCAGAGCAGGACCT | 5 | 0.9777 |
| 4093 | Hfe_T99 | GAAGCGCCGGCCTGGCTCGC | 4.9 | 0.9876 |
| 1042 | Hfe_T359 | TCCTGAGATCATTTGGTCCT | 4.9 | 0.976 |
| 399 | Hfe_T117 | AATGGGCCCGCGAGCCAGGC | 4.5 | 0.9907 |
| 3393 | Hfe_T39 | CCATTGGGCAATACGTCTTT | 4.1 | 0.928031 |
| 391 | Hfe_T229 | CGGGGACGTGCGGCCAGAGC | 4 | 0.9881 |
| 1090 | Hfe_T472 | CCTGGCCCACCAAGCTGGAG | 3.8 | 0.9884 |
| 423 | Hfe_T274 | ACTAGCTTTTTCTTTGCGCT | 3.4 | 0.9889 |
| 1278 | Hfe_T371 | TCAAGTGCCTCCTTTGGTGA | 3.3 | 0.9931 |
| 3619 | Hfe_T530 | TGAAAAGCTCTGACAACCTC | 2.7 | 0.984237 |
| 4096 | Hfe_T108 | CGTTAAATCTCCGCTTCTTT | 2.1 | 0.9908 |
| 980 | Hfe_T732 | TCTTTCCTTGTTTGAAGCTT | 2.1 | 0.9923 |
| 1005 | Hfe_T397 | TGTTGACTTCTGGACTATTA | 1.8 | 0.991 |
| 4085 | Hfe_T24 | CCGCGGTCTGCAAAAGCATC | 1.7 | 0.99 |
| 3433 | Hfe_T243 | TTTACCCTTGCCAGGAAGAC | 1 | 0.9928 |
| 1004 | Hfe_T558 | ACATGTTCACTGTTGACTTC | 0.9 | 0.9902 |
| 4102 | Hfe_T278 | CTCCGCTTCTTTTGGGGGGC | 0.7 | 0.992 |
| 398 | Hfe_T60 | GGGAAATGGGCCCGCGAGCC | 0.5 | 0.9912 |
| 1013 | Hfe_T566 | CACAGCAAGGGTACGTGGAG | 0.5 | 0.992518 |
| 3601 | Hfe_T537 | ACCTGCAGGGTGTGGGACTC | 0 | 0.9908 |
| 1088 | Hfe_T542 | CAGGGCCTGGCCCACCAAGC | 0 | 0.9866 |
| 3450 | Hfe_T311 | GACTCTAACACAGTGTCACT | 0 | 0.9904 |

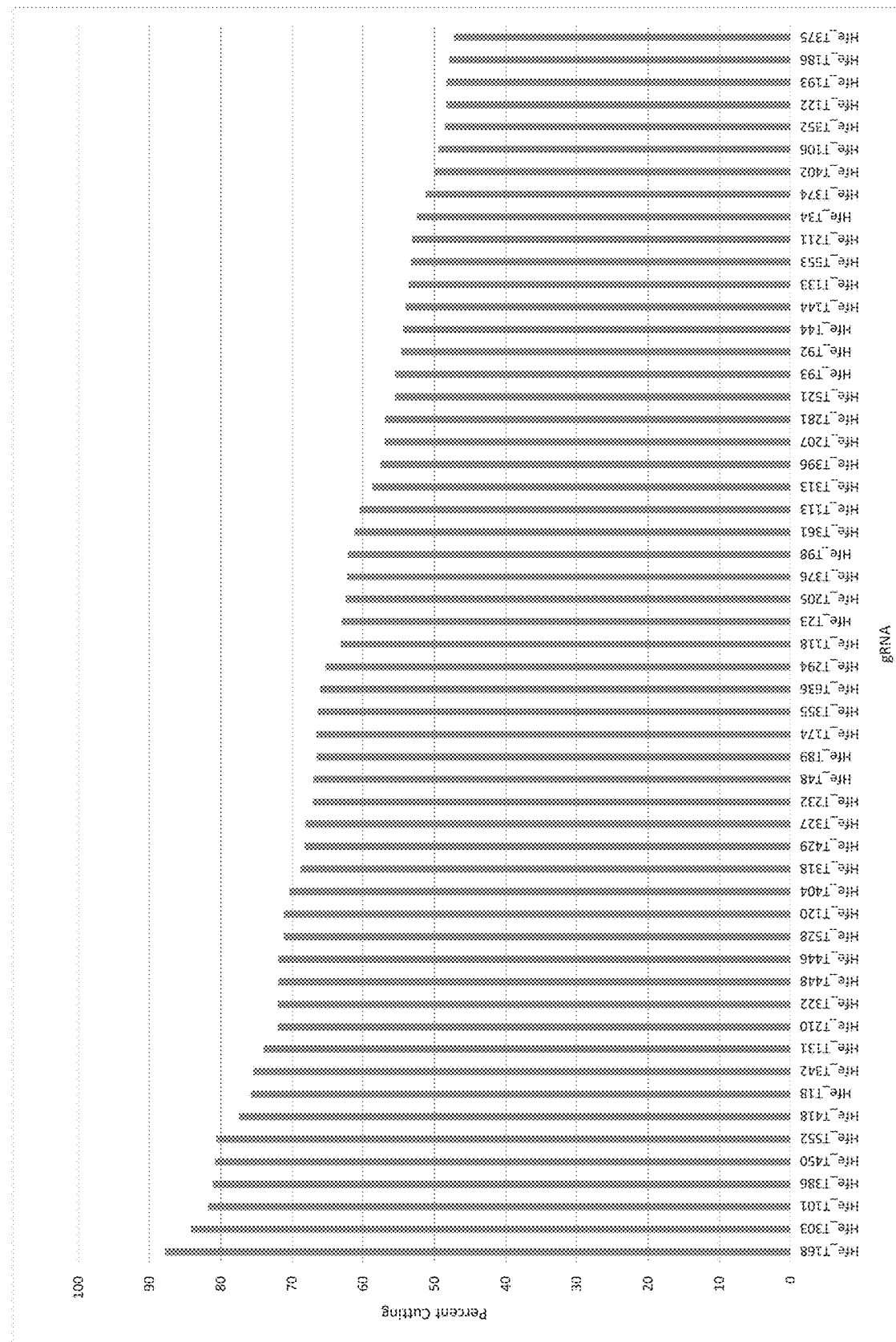

MATERIALS AND METHODS FOR TREATMENT OF HEREDITARY HAEMOCHROMATOSIS

RELATED APPLICATIONS

This application is a continuation of U.S. application Ser. No. 16/084,531 filed Sep. 12, 2018, which is a U.S. National Phase of International Application No. PCT/IB2017/000317 filed Mar. 16, 2017, which claims the benefit of U.S. Provisional Application No. 62/309,136 filed Mar. 16, 2016 and U.S. Provisional Application No. 62/323,890 filed Apr. 18, 2016, both of which are incorporated herein in their entirety by reference.

FIELD

The present application provides materials and methods for treating a patient with hereditary haemochromatosis (HHC), both ex vivo and in vivo. In addition, the present application provides materials and methods for modulating the expression, function, and/or activity of a haemochromatosis (HFE) gene in a cell by genome editing.

INCORPORATION BY REFERENCE OF SEQUENCE LISTING

This application contains a sequence listing in computer readable form Filename: CT12A_Seglisting; Filesize: 13,042,574 bytes; Created: Jul. 8, 2021), which is incorporated herein by reference in it entirety and forms part of the disclosure.

BACKGROUND

HHC is characterized by excessive storage of iron in the liver, skin, pancreas, heart, joints, and testes. It remains the most common, identified, genetic disorder in Caucasians. Although its geographic distribution is worldwide, it is most common in populations of northern European origin, particularly Nordic or Celtic ancestry, in which it occurs with a prevalence of approximately 1 per 220-250 individuals. The pathophysiologic predisposition to increased, inappropriate absorption of dietary iron may lead to the development of life-threatening complications such as cirrhosis, hepatocellular carcinoma (HCC), diabetes, and heart disease.

In 1996, HFE, a gene involved in HHC, was located on Chromosome 6 (6p21.3 region) and found to contain 7 exons spanning 12 kb.

It was discovered that the HFE gene has multiple allelic variants. One known mutation is a G-to-A missense mutation leading to the substitution of tyrosine for cysteine at amino acid position 282 of the protein product (C282Y). C282Y homozygotes account for 80-85% of typical patients with HHC. Allele frequencies of HFE C282Y in ethnically diverse western European white populations are 5-14% and in North American non-Hispanic whites are 6-7%. C282Y exists as a polymorphism only in Western European white and derivative populations, although C282Y may have arisen independently in non-whites outside Europe. There are two other regularly identified mutations of the HFE gene, one in which aspartate is substituted for histidine at amino acid position 63 (H63D), and the other in which cysteine is substituted for serine at amino acid position 65 (S65C). These mutations are generally not associated with iron loading unless seen with C282Y as a compound heterozygote, C282Y/H63D or C282Y/S65C.

Over the last 10 years, mutations of other genes coding for iron regulatory proteins have been implicated in inherited iron overload syndromes (e.g., hepcidin, hemojuvelin, transferrin receptor 2, and ferroportin). These mutations of other genes coding for iron regulatory proteins are thought to account for most of the non-HFE forms of HHC.

The largest predicted primary translation product of the HFE gene is 348 amino acids, which gives rise to a mature protein of approximately 321 amino acids after cleavage of the signal sequence. The HFE protein is similar to HLA Class I molecules at the level of the primary structure and tertiary structure. The mature protein is expressed on the cell surface as a heterodimer with beta-2-microglobulin, and this interaction is necessary for normal presentation on the cell surface. The C282Y pathogenic variant destroys a key cysteine residue that is required for disulfide bonding with beta-2-microglobulin. As a result, the HFE protein does not mature properly and becomes trapped in the endoplasmic reticulum and Golgi apparatus, leading to decreased cell-surface expression.

The diagnosis of HHC in individuals is typically based on finding elevated transferrin-iron saturation 45% or higher and serum ferritin concentration above the upper limit of normal (i.e., >300 ng/mL in men and >200 ng/mL in women) and two pathogenic variants on confirmatory HFE molecular genetic testing. Although serum ferritin concentration may increase progressively over time in untreated individuals with HHC, it is not specific for HHC, and therefore cannot be used alone for identification of individuals with HHC.

For patients diagnosed with HHC, treatment by phlebotomy (removal of blood) is an available option to help maintain serum ferritin concentration at s 50 ng/mL.

An alternative treatment for patients diagnosed with HHC includes genome engineering. Genome engineering refers to the strategies and techniques for the targeted, specific modification of the genetic information (genome) of living organisms. Genome engineering is a very active field of research because of the wide range of possible applications, particularly in the areas of human health; the correction of a gene carrying a harmful mutation, for example, or to explore the function of a gene. Early technologies developed to insert a transgene into a living cell were often limited by the random nature of the insertion of the new sequence into the genome. Random insertions into the genome may result in disrupting normal regulation of neighboring genes leading to severe unwanted effects. Furthermore, random integration technologies offer little reproducibility, as there is no guarantee that the sequence would be inserted at the same place in two different cells. Recent genome engineering strategies, such as ZFNs, TALENs, HEs and MegaTALs, enable a specific area of the DNA to be modified, thereby increasing the precision of the correction or insertion compared to early technologies. These newer platforms offer a much larger degree of reproducibility, but still have their limitations.

Despite efforts from researchers and medical professionals worldwide who have been trying to address HHC, there still remains a critical need for developing safe and effective treatments for HHC.

Currently, phlebotomy treatment is the only available treatment for addressing HHC, and it only aims to manage symptoms, not treat the cause.

SUMMARY

The present disclosure presents an approach to address the genetic basis of HHC. By using genome engineering tools to create permanent changes to the genome that can address the HFE gene and restore HFE protein activity with as few as a single treatment, the resulting therapy may ameliorate the effects of or completely eliminate HHC.

Provided herein are cellular, ex vivo and in vivo methods for creating permanent changes to the genome by deleting, inserting, correcting, or modulating the expression or function of one or more mutations within or near an HFE gene or other DNA sequences that encode regulatory elements of the HFE gene, which can be used to treat HHC. Also provided herein are components, kits, and compositions for performing such methods. Also provided are cells produced by such methods.

Provided herein is a method for editing an HFE gene in a human cell by genome editing, the method comprising: introducing into the human cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene and results in restoration of HFE protein activity. The human cell can be a liver cell, skin cell, pancreatic cell, heart cell, joint cell, or cell from the testes.

Also provided herein is a method for inserting a haemochromatosis (HFE) gene in a human cell by genome editing, the method comprising: introducing into the human cell one or more deoxyribonucleic acid (DNA) endonucleases to effect one or more single-strand breaks (SSBs) or double-strand breaks (DSBs) within or near a safe harbor locus that results in a permanent insertion of the HFE gene, and results in restoration of HFE protein activity.

Also provided herein is an ex vivo method for treating a patient (e.g., a human) with HHC, the method comprising: creating a patient specific induced pluripotent stem cell (iPSC); editing within or near an HFE gene or other DNA sequences that encode regulatory elements of the HFE gene of the iPSC, or editing within or near a safe harbor locus of the iPSC; differentiating the genome-edited iPSC into a hepatocyte; and implanting the hepatocyte into the patient.

The step of creating a patient specific induced pluripotent stem cell (iPSC) can comprise: isolating a somatic cell from the patient; and introducing a set of pluripotency-associated genes into the somatic cell to induce the somatic cell to become a pluripotent stem cell. The somatic cell can be a fibroblast. The set of pluripotency-associated genes can be one or more of the genes selected from the group consisting of OCT4, SOX2, KLF4, Lin28, NANOG and cMYC.

The step of editing within or near an HFE gene or other DNA sequences that encode regulatory elements of the HFE gene of the iPSC or editing within or near a safe harbor locus of the iPSC can comprise: introducing into the iPSC one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene, or within or near a safe harbor locus, that results in restoration of HFE protein activity.

The safe harbor locus can be selected from the group consisting of AAVS1 (PPP1R12C), ALB, Angptl3, ApoC3, ASGR2, CCR5, FIX (F9), G6PC, Gys2, HGD, Lp(a), Pcsk9, Serpina1, TF, and TTR.

The step of differentiating the genome-edited iPSC into a hepatocyte can comprise: contacting the genome-edited iPSC with one or more of activin, B27 supplement, FGF4, HGF, BMP2, BMP4, Oncostatin M, or Dexametason.

The step of implanting the hepatocyte into the patient can comprise: implanting the hepatocyte into the patient by transplantation, local injection, systemic infusion, or combinations thereof.

Also provided herein is an ex vivo method for treating a patient (e.g., a human) with HHC, the method comprising: performing a biopsy of the patient's liver; isolating a liver specific progenitor cell or primary hepatocyte from the patient's liver, editing within or near an HFE gene or other DNA sequences that encode regulatory elements of the HFE gene of the liver specific progenitor cell or primary hepatocyte or editing within or near a safe harbor locus of the liver specific progenitor cell or primary hepatocyte; and implanting the genome-edited liver specific progenitor cell or primary hepatocyte into the patient.

The step of isolating a liver specific progenitor cell or primary hepatocyte from the patient's liver can comprise perfusion of fresh liver tissues with digestion enzymes, cell differential centrifugation, cell culturing, or combinations thereof.

The step of editing within or near an HFE gene or other DNA sequences that encode regulatory elements of the HFE gene of the liver specific progenitor cell or primary hepatocyte or editing within or near a safe harbor locus of the liver specific progenitor cell or primary hepatocyte can comprise: introducing into the liver specific progenitor cell or primary hepatocyte one or more deoxynbonucleic acid (DNA) endonucleases to effect one or more single-strand breaks (SSBs) or double-strand breaks (DSBs) within or near the HFE gene or other DNA sequences that encode regulatory elements of the HFE gene or within or near a safe harbor locus that results in a permanent deletion, insertion, correction, or modulation of expression or function of one or more mutations within or near or affecting the expression or function of the HFE gene, or within or near a safe harbor locus, that results in restoration of HFE protein activity.

The safe harbor locus can be selected from the group consisting of AAVS1 (PPP1R12C), ALB, Angptl3, ApoC3, ASGR2, CCR5, FIX (F9), G6PC, Gys2, HGD, Lp(a), Pcsk9, Serpina1, TF, and TTR.

The step of implanting the genome-edited liver specific progenitor cell or primary hepatocyte into the patient can comprise: implanting the genome-edited liver specific progenitor cell or primary hepatocyte into the patient by transplantation, local injection, systemic infusion, or combinations thereof.

Also provided herein is an ex vivo method for treating a patient (e.g., a human) with HHC, the method comprising: isolating a mesenchymal stem cell from the patient; editing within or near an HFE gene or other DNA sequences that encode regulatory elements of the HFE gene of the mesenchymal stem cell, or editing within or near a safe harbor locus of the mesenchymal stem cell; differentiating the genome-edited mesenchymal stem cell into a hepatocyte; and implanting the hepatocyte into the patient.

The mesenchymal stem cell can be isolated from the patient's bone marrow by performing a biopsy of the patient's bone marrow or the mesenchymal stem cell can be isolated from peripheral blood. The step of isolating a mesenchymal stem cell from the patient can comprise aspiration of bone marrow and isolation of mesenchymal cells using density gradient centrifugation media.

The step of editing within or near the HFE gene or other DNA sequences that encode regulatory elements of the HFE gene of the mesenchymal stem cell can comprise introducing into the mesenchymal stem cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene or within or near a safe harbor locus, that results in restoration of HFE protein activity.

The safe harbor locus can be selected from the group consisting of AAVS1 (PPP1R12C), ALB, Angptl3, ApoC3, ASGR2, CCR5, FIX (F9), G6PC, Gys2, HGD, Lp(a). Pcsk9, Serpina1, TF, and TTR.

The step of differentiating the genome-edited mesenchymal stem cell into a hepatocyte can comprise contacting the genome-edited mesenchymal stem cell with one or more of insulin, transferrin, FGF4, HGF, or bile acids.

The step of implanting the hepatocyte into the patient can comprise implanting the hepatocyte into the patient by transplantation, local injection, systemic infusion, or combinations thereof.

Also provided herein is an in vivo method for treating a patient (e.g., a human) with HHC, the method comprising the step of editing an HFE gene in a cell of the patient or other DNA sequences that encode regulatory elements of the HFE gene, or editing within or near a safe harbor locus in a cell of the patient. The cell can be a liver cell, skin cell, pancreatic cell, heart cell, joint cell, or cell from the testes.

The step of editing an HFE gene in a cell of the patient can comprise introducing into the cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene or within or near a safe harbor locus that results in restoration of HFE protein activity.

The one or more DNA endonucleases can be a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

The method can comprise introducing into the cell one or more polynucleotides encoding the one or more DNA endonucleases. The method can comprise introducing into the cell one or more ribonucleic acids (RNAs) encoding the one or more DNA endonucleases. The one or more polynucleotides or one or more RNAs can be one or more modified polynucleotides or one or more modified RNAs. The DNA endonuclease can be one or more proteins or polypeptides.

The method can further comprise introducing into the cell one or more guide ribonucleic acids (gRNAs). The one or more gRNAs can be single-molecule guide RNA (sgRNAs). The one or more gRNAs or one or more sgRNAs can be one or more modified gRNAs, one or more modified sgRNAs, or combinations thereof. The one or more DNA endonucleases can be pre-complexed with one or more gRNAs, one or more sgRNAs, or combinations thereof.

The method can further comprise introducing into the cell a polynucleotide donor template comprising at least a portion of the wild-type HFE gene, DNA sequences that encode wild-type regulatory elements of the HFE gene, and/or cDNA. The at least a portion of the wild-type HFE gene or cDNA can be exon 1, exon 2, exon 3, exon 4, exon 5, exon 6, exon 7, intronic regions, fragments of combinations thereof, or the entire HFE gene or cDNA. The donor template can be either single or double stranded. The donor template can have homologous arms to the 6p21.3 region.

The method can further comprise introducing into the cell one guide ribonucleic acid (gRNA) and a polynucleotide donor template comprising at least a portion of the wild-type HFE gene. The method can further comprise introducing into the cell one guide ribonucleic acid (gRNA) and a polynucleotide donor template comprising at least a portion of a codon optimized or modified HFE gene. The one or more DNA endonucleases can be one or more Cas9 or Cpf1 endonucleases that effect one single-strand break (SSB) or double-strand break (DSB) at a locus within or near the HFE gene (or codon optimized or modified HFE gene) or other DNA sequences that encode regulatory elements of the HFE gene, or within or near a safe harbor locus that facilitates insertion of a new sequence from the polynucleotide donor template into the chromosomal DNA at the locus or safe harbor locus that results in a permanent insertion or correction of a part of the chromosomal DNA of the HFE gene or other DNA sequences that encode regulatory elements of the HFE gene proximal to the locus, or safe harbor locus. The gRNA can comprise a spacer sequence that is complementary to a segment of the locus. Proximal can mean nucleotides both upstream and downstream of the locus or safe harbor locus.

The method can further comprise introducing into the cell one or more guide ribonucleic acid (gRNAs) and a polynucleotide donor template comprising at least a portion of the wild-type HFE gene. The one or more DNA endonucleases can be one or more Cas9 or Cpf1 endonucleases that effect or create at least two (e.g., a pair) single-strand breaks (SSBs) and/or double-strand breaks (DSBs), the first at a 5' locus and the second at a 3' locus, within or near the HFE gene or other DNA sequences that encode regulatory elements of the HFE gene or within or near a safe harbor locus that facilitates insertion of a new sequence from the polynucleotide donor template into the chromosomal DNA between the 5' locus and the 3' locus that results in a permanent insertion or correction of the chromosomal DNA between the 5' locus and the 3' locus within or near the HFE gene or other DNA sequences that encode regulatory elements of the HFE gene or within or near a safe harbor locus. The first guide RNA can comprise a spacer sequence that is complementary to a segment of the 5' locus and the second guide RNA can comprise a spacer sequence that is complementary to a segment of the 3' locus.

The one or more gRNAs can be one or more single-molecule guide RNA (sgRNAs). The one or more gRNAs or one or more sgRNAs can be one or more modified gRNAs or one or more modified sgRNAs. The one or more DNA endonucleases can be pre-complexed with one or more gRNAs or one or more sgRNAs.

The at least a portion of the wild-type HFE gene or cDNA can be exon 1, exon 2, exon 3, exon 4, exon 5, exon 6, exon 7, intronic regions, fragments, or combinations thereof, or the entire HFE gene or cDNA.

The donor template can be either a single or double stranded polynucleotide. The donor template can have homologous arms to the 6p21.3 region.

The gRNA or sgRNA can be directed to one or more of the pathological variants: C282Y, H63D, or S65C or combinations thereof.

The SSB or DSB can be in the first, second, third, fourth, fifth, sixth, seventh exon, or combinations thereof or introns of the HFE gene.

The insertion or correction can be by homology directed repair (HDR).

The method can further comprise introducing into the cell two guide ribonucleic acids (gRNAs). The one or more DNA endonucleases can be one or more Cas9 or Cpf1 endonucleases that effect or create two or more (e.g., a pair) double-strand breaks (DSBs), the first at a 5' DSB locus and the second at a 3' DSB locus, within or near the HFE gene or other DNA sequences that encode regulatory elements of the HFE gene, or within or near a safe harbor locus that causes a deletion of the chromosomal DNA between the 5' DSB locus and the 3' DSB locus that results in a permanent deletion of the chromosomal DNA between the 5' DSB locus and the 3' DSB locus within or near the HFE gene or other DNA sequences that encode regulatory elements of the HFE gene or safe harbor locus. The first guide RNA can comprise a spacer sequence that is complementary to a segment of the 5' DSB locus and the second guide RNA comprises a spacer sequence that is complementary to a segment of the 3' DSB locus.

The two gRNAs can be two single-molecule guide RNA (sgRNAs). The two gRNAs or two sgRNAs can be two modified gRNAs or two modified sgRNAs. The one or more DNA endonucleases can be pre-complexed with one or two gRNAs or one or two sgRNAs.

The 5' DSB and/or 3' DSB can be in or near the first exon, first intron, second exon, second intron, third exon, third intron, fourth exon, fourth intron, fifth exon, fifth intron, sixth exon, sixth intron, seventh exon, seventh intron, or combinations thereof, of the HFE gene.

The deletion can be a deletion of 1 kb or less.

The Cas9 or Cpf1 mRNA, gRNA, and donor template can be formulated into separate lipid nanoparticles or co-formulated into a lipid nanoparticle.

The Cas9 or Cpf1 mRNA can be formulated into a lipid nanoparticle, and the gRNA and donor template can be delivered to the cell by an adeno-associated virus (AAV) vector.

The Cas9 or Cpf1 mRNA can be formulated into a lipid nanoparticle, and the gRNA can be delivered to the cell by electroporation and donor template can be delivered to the cell by an adeno-associated virus (AAV) vector.

The HFE gene can be located on Chromosome 6: 26087458-26095569 (Genome Reference Consortium—GRCh38/hg38).

The restoration of HFE protein activity can be compared to a control (e.g., wild-type or normal HFE protein activity).

Also provided herein is one or more guide ribonucleic acids (gRNAs) for editing an HFE gene in a cell from a patient with HHC. The one or more gRNAs and/or sgRNAs can comprise a spacer sequence selected from the group consisting of nucleic acid sequences in SEQ ID NOs: 1-64,980 of the Sequence Listing. The one or more gRNAs can be one or more single-molecule guide RNAs (sgRNAs). The one or more gRNAs or one or more sgRNAs can be one or more modified gRNAs or one or more modified sgRNAs. The cell can be a liver cell, skin cell, pancreatic cell, heart cell, joint cell, or cell from the testes.

It is understood that the inventions described in this specification are not limited to the examples summarized in this Summary. Various other aspects are described and exemplified herein.

BRIEF DESCRIPTION OF THE DRAWINGS

Various aspects of materials and methods for treatment of HHC disclosed and described in this specification can be better understood by reference to the accompanying figures, in which:

FIG. 2A describes the cutting efficiencies of gRNAs selected via an in-vitro transcribed (IVT) gRNA screen;
FIG. 2B describes the cutting efficiencies of gRNAs selected via an in-vitro transcribed (IVT) gRNA screen;
FIG. 2C describes the cutting efficiencies of gRNAs selected via an in-vitro transcribed (IVT) gRNA screen;
FIG. 2D describes the cutting efficiencies of gRNAs selected via an in-vitro transcribed (IVT) gRNA screen;
FIG. 3A describes the cutting efficiency of S. pyogenes gRNAs in HEK293T cells targeting the HFE gene.

BRIEF DESCRIPTION OF THE SEQUENCE LISTING

Figure 1A:
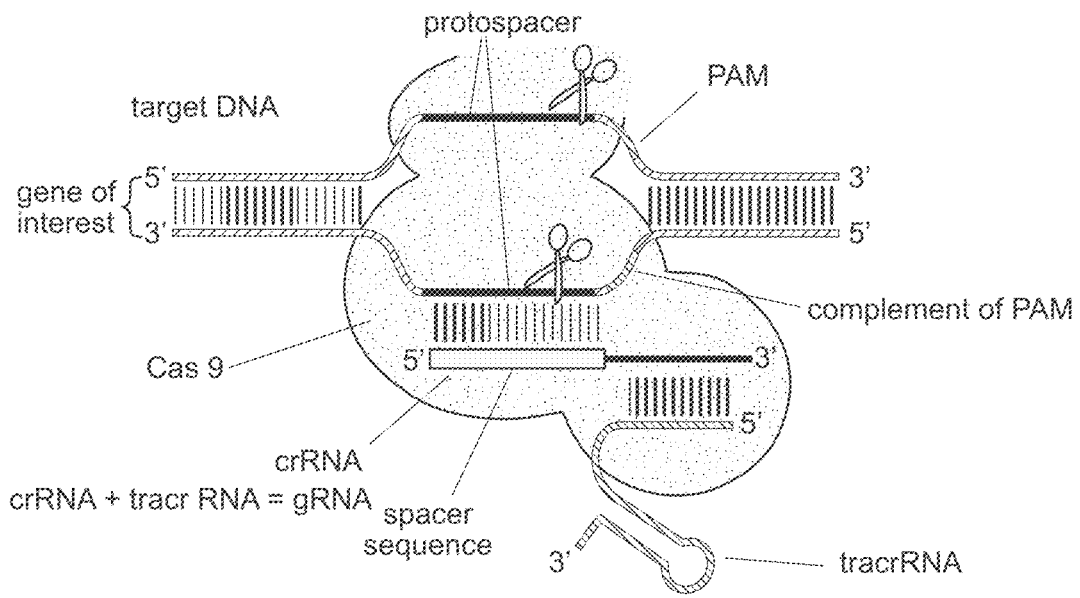
FIG. 1A is a depiction of the type II CRISPR/Cas system.

SEQ ID NOs: 1-4,455 are 20 bp spacer sequences for targeting an HFE gene with an S. pyogenes Cas9 endonuclease.

SEQ ID NOs: 4,456-4,979 are 20 bp spacer sequences for targeting an HFE gene with an S. aureus Cas9 endonuclease.

SEQ ID NOs: 4,980-5,139 are 20 bp spacer sequences for targeting an HFE gene with an S. thermophilus Cas9 endonuclease.

SEQ ID NOs: 5,140-5,192 are 20 bp spacer sequences for targeting an HFE gene with a T. denticola Cas9 endonuclease.

SEQ ID NOs. 5,193-5,617 are 20 bp spacer sequences for targeting an HFE gene with an N. meningitides Cas9 endonuclease.

SEQ ID NOs: 5,618-10,121 are 20-24 bp spacer sequences for targeting an HFE gene with an Acidominococcus, a Lachnospiraceae, and a Franciscella Novicida Cpf1 endonuclease.

SEQ ID NOs: 10,122-12,153 are 20 bp spacer sequences for targeting exons 1-2 of an AAVS1 (PPP1R12C) gene with an S. pyogenes Cas9 endonuclease.

SEQ ID NOs: 12,154-12,324 are 20 bp spacer sequences for targeting exons 1-2 of an AAVS1 (PPP1R12C) gene with an S. aureus Cas9 endonuclease.

SEQ ID NOs: 12,325-12,342 are 20 bp spacer sequences for targeting exons 1-2 of an AAVS1 (PPP1R12C) gene with an S. thermophilus Cas9 endonuclease.

SEQ ID NOs: 12,343-12,351 are 20 bp spacer sequences for targeting exons 1-2 of an AAVS1 (PPP1R12C) gene with a T. denticola Cas9 endonuclease.

SEQ ID NOs: 12,352-12,426 are 20 bp spacer sequences for targeting exons 1-2 of an AAVS1 (PPP1R12C) gene with an N. meningitides Cas9 endonuclease.

SEQ ID NOs: 12,427-13,602 are 22 bp spacer sequences for targeting exons 1-2 of an AAVS1 (PPP1R12C) gene with an Acidominococcus, Lachnospiraceae, and Francisella novicida Cpf1 endonuclease.

SEQ ID NOs: 13,603-13,770 are 20 bp spacer sequences for targeting exons 1-2 of an Alb gene with an *S. pyogenes* Cas9 endonuclease.

SEQ ID NOs: 13,771-13,798 are 20 bp spacer sequences for targeting exons 1-2 of an Alb gene with an *S. aureus* Cas9 endonuclease.

SEQ ID NOs: 13,799-13,816 are 20 bp spacer sequences for targeting exons 1-2 of an Alb gene with an *S. thermophilus* Cas9 endonuclease.

SEQ ID NOs: 13,817-13,821 are 20 bp spacer sequences for targeting exons 1-2 of an Alb gene with a *T. denticola* Cas9 endonuclease.

SEQ ID NOs: 13,822-13,845 are 20 bp spacer sequences for targeting exons 1-2 of an Alb gene with an *N. meningitides* Cas9 endonuclease.

SEQ ID NOs: 13,846-14,224 are 22 bp spacer sequences for targeting exons 1-2 of an Alb gene with an *Acidominococcus*, *Lachnospiraceae*, and *Francisella novicida* Cpf1 endonuclease.

SEQ ID NOs: 14,225-14,569 are 20 bp spacer sequences for targeting exons 1-2 of an Angptl3 gene with an *S. pyogenes* Cas9 endonuclease.

SEQ ID NOs: 14,570-14,605 are 20 bp spacer sequences for targeting exons 1-2 of an Angptl3 gene with an *S. aureus* Cas9 endonuclease.

SEQ ID NOs: 14,606-14,628 are 20 bp spacer sequences for targeting exons 1-2 of an Angptl3 gene with an *S. thermophilus* Cas9 endonuclease.

SEQ ID NOs: 14,629-14,641 are 20 bp spacer sequences for targeting exons 1-2 of an Angptl3 gene with a *T. denticola* Cas9 endonuclease.

SEQ ID NOs: 14,642-14,704 are 20 bp spacer sequences for targeting exons 1-2 of an Angptl3 gene with an *N. meningitides* Cas9 endonuclease.

SEQ ID NOs: 14,705-15,552 are 22 bp spacer sequences for targeting exons 1-2 of an Angptl3 gene with an *Acidominococcus*, *Lachnospiraceae*, and *Francisella novicida* Cpf1 endonuclease.

SEQ ID NOs: 15,553-15,955 are 20 bp spacer sequences for targeting exons 1-2 of an ApoC3 gene with an *S. pyogenes* Cas9 endonuclease.

SEQ ID NOs: 15,956-15,980 are 20 bp spacer sequences for targeting exons 1-2 of an ApoC3 gene with an *S. aureus* Cas9 endonuclease.

SEQ ID NOs: 15,981-15,983 are 20 bp spacer sequences for targeting exons 1-2 of an ApoC3 gene with an *S. thermophilus* Cas9 endonuclease.

SEQ ID NOs: 15,984-15,985 are 20 bp spacer sequences for targeting exons 1-2 of an ApoC3 gene with a *T. denticola* Cas9 endonuclease.

SEQ ID NOs: 15,986-15,997 are 20 bp spacer sequences for targeting exons 1-2 of an ApoC3 gene with an *N. meningitides* Cas9 endonuclease.

SEQ ID NOs: 15,998-16,229 are 22 bp spacer sequences for targeting exons 1-2 of an ApoC3 gene with an *Acidominococcus*, *Lachnospiraceae*, and *Francisella novicida* Cpf1 endonuclease.

SEQ ID NOs: 16,230-17,997 are 20 bp spacer sequences for targeting exons 1-2 of an ASGR2 gene with an *S. pyogenes* Cas9 endonuclease.

SEQ ID NOs: 17,998-18,203 are 20 bp spacer sequences for targeting exons 1-2 of an ASGR2 gene with an *S. aureus* Cas9 endonuclease.

SEQ ID NOs: 18,204-18,227 are 20 bp spacer sequences for targeting exons 1-2 of an ASGR2 gene with an *S. thermophilus* Cas9 endonuclease.

SEQ ID NOs: 18,228-18,239 are 20 bp spacer sequences for targeting exons 1-2 of an ASGR2 gene with a *T. denticola* Cas9 endonuclease.

SEQ ID NOs: 18,240-18,322 are 20 bp spacer sequences for targeting exons 1-2 of an ASGR2 gene with an *N. meningitides* Cas9 endonuclease.

SEQ ID NOs: 18,323-19,762 are 22 bp spacer sequences for targeting exons 1-2 of an ASGR2 gene with an *Acidominococcus*, *Lachnospiraceae*, and *Francisella novicida* Cpf1 endonuclease.

SEQ ID NOs: 19,763-19,965 are 20 bp spacer sequences for targeting exons 1-2 of a CCR5 gene with an *S. pyogenes* Cas9 endonuclease.

SEQ ID NOs: 19,966-19,997 are 20 bp spacer sequences for targeting exons 1-2 of a CCR5 gene with an *S. aureus* Cas9 endonuclease.

SEQ ID NOs: 19,998-20,011 are 20 bp spacer sequences for targeting exons 1-2 of a CCR5 gene with an *S. thermophilus* Cas9 endonuclease.

SEQ ID NOs: 20,012-20,013 are 20 bp spacer sequences for targeting exons 1-2 of a CCR5 gene with a *T. denticola* Cas9 endonuclease.

SEQ ID NOs: 20,014-20,041 are 20 bp spacer sequences for targeting exons 1-2 of a CCR5 gene with an *N. meningitides* Cas9 endonuclease.

SEQ ID NOs: 20,042-20,341 are 22 bp spacer sequences for targeting exons 1-2 of a CCR5 gene with an *Acidominococcus*, *Lachnospiraceae*, and *Francisella novicida* Cpf1 endonuclease.

SEQ ID NOs: 20,342-21,807 are 20 bp spacer sequences for targeting exons 1-2 of an F9 gene with an *S. pyogenes* Cas9 endonuclease.

SEQ ID NOs: 21,808-21,970 are 20 bp spacer sequences for targeting exons 1-2 of an F9 gene with an *S. aureus* Cas9 endonuclease.

SEQ ID NOs: 21,971-22,031 are 20 bp spacer sequences for targeting exons 1-2 of an F9 gene with an *S. thermophilus* Cas9 endonuclease.

SEQ ID NOs: 22,032-22,056 are 20 bp spacer sequences for targeting exons 1-2 of an F9 gene with a *T. denticola* Cas9 endonuclease.

SEQ ID NOs: 22,057-22,209 are 20 bp spacer sequences for targeting exons 1-2 of an F9 gene with an *N. meningitides* Cas9 endonuclease.

SEQ ID NOs: 22,210-24,350 are 22 bp spacer sequences for targeting exons 1-2 of an F9 gene with an *Acidominococcus*, *Lachnospiraceae*, and *Francisella novicida* Cpf1 endonuclease.

SEQ ID NOs: 24,351-25,366 are gRNA 20 bp spacer sequences for targeting exons 1-2 of the G6PC gene with an *S. pyogenes* Cas9 endonuclease.

SEQ ID NOs: 25,367-25,483 are gRNA 20 bp spacer sequences for targeting exons 1-2 of the G6PC gene with an *S. aureus* Cas9 endonuclease.

SEQ ID NOs: 25,484-25,507 are gRNA 20 bp spacer sequences for targeting exons 1-2 of the G6PC gene with an *S. thermophilus* Cas9 endonuclease.

SEQ ID NOs: 25,508-25,516 are gRNA 20 bp spacer sequences for targeting exons 1-2 of the G6PC gene with a *T. denticola* Cas9 endonuclease.

SEQ ID NOs: 25,517-25,606 are gRNA 20 bp spacer sequences for targeting exons 1-2 of the G6PC gene with an *N. meningitides* Cas9 endonuclease.

SEQ ID NOs: 25,607-26,701 are gRNA 22 bp spacer sequences for targeting exons 1-2 of the G6PC gene with an *Acidominococcus*, *Lachnospiraceae*. and *Francisella novicida* Cpf1 endonuclease.

SEQ ID NOs: 26,702-32,194 are 20 bp spacer sequences for targeting exons 1-2 of an Gys2 gene with an *S. pyogenes* Cas9 endonuclease.

SEQ ID NOs: 32,195-32,870 are gRNA 20 bp spacer sequences for targeting exons 1-2 of an Gys2 gene with an *S. aureus* Cas9 endonuclease.

SEQ ID NOs: 32,871-33,148 are gRNA 20 bp spacer sequences for targeting exons 1-2 of an Gys2 gene with an *S. thermophilus* Cas9 endonuclease.

SEQ ID NOs: 33,149-33,262 are gRNA 20 bp spacer sequences for targeting exons 1-2 of an Gys2 gene with a *T. denticola* Cas9 endonuclease.

SEQ ID NOs: 33,263-33,942 are gRNA 20 bp spacer sequences for targeting exons 1-2 of an Gys2 gene with an *N. meningitides* Cas9 endonuclease.

SEQ ID NOs: 33,943-42,374 are gRNA 22 bp spacer sequences for targeting exons 1-2 of an Gys2 gene with an Acidominococcus, Lachnospiraceae, and *Francisella novicida* Cpf1 endonuclease.

SEQ ID NOs: 42,375-44,067 are gRNA 20 bp spacer sequences for targeting exons 1-2 of an HGD gene with an *S. pyogenes* Cas9 endonuclease.

SEQ ID NOs: 44,068-44,281 are gRNA 20 bp spacer sequences for targeting exons 1-2 of an HGD gene with an *S. aureus* Cas9 endonuclease.

SEQ ID NOs: 44,282-44,364 are gRNA 20 bp spacer sequences for targeting exons 1-2 of an HGD gene with an *S. thermophilus* Cas9 endonuclease.

SEQ ID NOs: 44,365-44,383 are gRNA 20 bp spacer sequences for targeting exons 1-2 of an HGD gene with a *T. denticola* Cas9 endonuclease.

SEQ ID NOs: 44,384-44,584 are gRNA 20 bp spacer sequences for targeting exons 1-2 of an HGD gene with an *N. meningitides* Cas9 endonuclease.

SEQ ID NOs: 44,585-46,909 are gRNA 22 bp spacer sequences for targeting exons 1-2 of an HGD gene with an Acidominococcus, Lachnospiraceae, and *Francisella novicida* Cpf1 endonuclease.

SEQ ID NOs: 46,910-50,704 are gRNA 20 bp spacer sequences for targeting exons 1-2 of an Lp(a) gene with an *S. pyogenes* Cas9 endonuclease.

SEQ ID NOs: 50,705-51,114 are gRNA 20 bp spacer sequences for exons 1-2 of targeting the Lp(a) gene with an *S. aureus* Cas9 endonuclease.

SEQ ID NOs: 51,115-51,250 are gRNA 20 bp spacer sequences for targeting the exons 1-2 of Lp(a) gene with an *S. thermophilus* Cas9 endonuclease.

SEQ ID NOs: 51,251-51,285 are gRNA 20 bp spacer sequences for targeting exons 1-2 of an Lp(a) gene with a *T. denticola* Cas9 endonuclease.

SEQ ID NOs: 51,286-51,653 are gRNA 20 bp spacer sequences for targeting exons 1-2 of an Lp(a) gene with an *N. meningitides* Cas9 endonuclease.

SEQ ID NOs: 51,654-56,274 are gRNA 22 bp spacer sequences for targeting exons 1-2 of an Lp(a) gene with an Acidominococcus, Lachnospiraceae, and *Francisella novicida* Cpf1 endonuclease.

SEQ ID NOs: 56,275-58,294 are gRNA 20 bp spacer sequences for targeting exons 1-2 of a PCSK9 gene with an *S. pyogenes* Cas9 endonuclease.

SEQ ID NOs: 58,295-58,481 are gRNA 20 bp spacer sequences for targeting exons 1-2 of a PCSK9 gene with an *S. aureus* Cas9 endonuclease.

SEQ ID NOs: 58,482-58,517 are gRNA 20 bp spacer sequences, for targeting exons 1-2 of a PCSK9 gene with an *S. thermophilus* Cas9 endonuclease.

SEQ ID NOs: 58,518-58,531 are gRNA 20 bp spacer sequences for targeting exons 1-2 of a PCSK9 gene with a *T. denticola* Cas9 endonuclease.

SEQ ID NOs: 58,532-58,671 are gRNA 20 bp spacer sequences for targeting exons 1-2 of a PCSK9 gene with an *N. meningitides* Cas9 endonuclease.

SEQ ID NOs: 58,672-60,465 are gRNA 22 bp spacer sequences for targeting exons 1-2 of a PCSK9 gene with an Acidominococcus, Lachnospiraceae, and *Francisella novicida* Cpf1 endonuclease.

SEQ ID NOs: 60,466-61,603 are gRNA 20 bp spacer sequences for targeting exons 1-2 of a Serpina1 gene with an *S. pyogenes* Cas9 endonuclease.

SEQ ID NOs: 61,604-61,696 are gRNA 20 bp spacer sequences for targeting exons 1-2 of a Serpina1 gene with an *S. aureus* Cas9 endonuclease.

SEQ ID NOs: 61,697-61,708 are gRNA 20 bp spacer sequences for targeting exons 1-2 of a Serpina1 gene with an *S. thermophilus* Cas9 endonuclease.

SEQ ID NOs: 61,709-61,711 are gRNA 20 bp spacer sequences for targeting exons 1-2 of a Serpina1 gene with a *T. denticola* Cas9 endonuclease.

SEQ ID NOs: 61,712-61,762 are gRNA 20 bp spacer sequences for targeting exons 1-2 of a Serpina1 gene with an *N. meningitides* Cas9 endonuclease.

SEQ ID NOs: 61,763-62,566 are gRNA 22 bp spacer sequences for targeting exons 1-2 of a Serpina1 gene with an Acidominococcus, Lachnospiraceae, and *Francisella novicida* Cpf1 endonuclease.

SEQ ID NOs: 62,567-63,398 are gRNA 20 bp spacer sequences for targeting exons 1-2 of a TF gene with an *S. pyogenes* Cas9 endonuclease.

SEQ ID NOs: 63,399-63,484 are gRNA 20 bp spacer sequences for targeting exons 1-2 of a TF gene with an *S. aureus* Cas9 endonuclease.

SEQ ID NOs: 63,485-63,496 are gRNA 20 bp spacer sequences for targeting exons 1-2 of a TF gene with an *S. thermophilus* Cas9 endonuclease.

SEQ ID NOs: 63,497-63,503 are gRNA 20 bp spacer sequences for targeting exons 1-2 of a TF gene with a *T. denticola* Cas9 endonuclease.

SEQ ID NOs: 63,504-63,547 are gRNA 20 bp spacer sequences for targeting exons 1-2 of a TF gene with an *N. meningitides* Cas9 endonuclease.

SEQ ID NOs: 63,548-64,183 are gRNA 22 bp spacer sequences targeting exons 1-2 of a TF gene with an Acidominococcus, Lachnospiraceae, and *Francisella novicida* Cpf1 endonuclease.

SEQ ID NOs: 64,184-64,483 are gRNA 20 bp spacer sequences for targeting exons 1-2 of an TTR gene with an *S. pyogenes* Cas9 endonuclease.

SEQ ID NOs: 64,484-64,524 are gRNA 20 bp spacer sequences for targeting exons 1-2 of a TTR gene with an *S. aureus* Cas9 endonuclease.

SEQ ID NOs: 64,525-64,541 are gRNA 20 bp spacer sequences for targeting exons 1-2 of a TTR gene with an *S. thermophilus* Cas9 endonuclease.

SEQ ID NOs: 64,542-64,543 are gRNA 20 bp spacer sequences for targeting exons 1-2 of a TTR gene with a *T. denticola* Cas9 endonuclease.

SEQ ID NOs: 64,544-64,578 are gRNA 20 bp spacer sequences for targeting exons 1-2 of a TTR gene with an *N. meningitides* Cas9 endonuclease.

SEQ ID NOs: 64,579-64,980 are gRNA 22 bp spacer sequences for targeting exons 1-2 of a TTR gene with an Acidominococcus, Lachnospiraceae, and *Francisella novicida* Cpf1 endonuclease.

DETAILED DESCRIPTION

Hereditary Haemochromatosis (HHC)

HFE, a gene involved in HHC, is located on Chromosome 6 (6p21.3 region) and contains 7 exons spanning 12 kb.

It was discovered that the HFE gene has multiple allelic variants. One known mutation is a G-to-A missense mutation leading to the substitution of tyrosine for cysteine at amino acid position 282 of the protein product (C282Y). C282Y homozygotes account for 80%-85% of typical patients with HHC. Allele frequencies of HFE C282Y in ethnically diverse western European white populations are 5-14% and in North American non-Hispanic whites are 6-7%. C282Y exists as a polymorphism only in Western European white and derivative populations, although C282Y may have arisen independently in non-whites outside Europe. There are two other regularly identified mutations of the HFE gene, one in which aspartate is substituted for histidine at amino acid position 63 (H63D), and the other in which cysteine is substituted for serine at amino acid position 65 (S65C). These mutations are generally not associated with iron loading unless seen with C282Y as a compound heterozygote, C282Y/H63D or C282Y/S65C.

Mutations of other genes coding for iron regulatory proteins have been implicated in inherited iron overload syndromes (e.g., hepcidin, hemojuvelin, transferrin receptor 2, and ferroportin). These other mutated genes are thought to account for most of the non-HFE forms of HHC.

Therapeutic Approach

As the known forms of HHC are monogenic disorders with recessive inheritance, it is likely that correcting one of the mutant alleles per cell will be sufficient for correction and restoration or partial restoration of HFE function. The correction of one allele can coincide with one copy that remains with the original mutation, or a copy that was cleaved and repaired by non-homologous end joining (NHEJ) and therefore was not properly corrected. Bi-allelic correction can also occur. Various editing strategies that can be employed for specific mutations are discussed below.

Correction of one or possibly both of the mutant alleles provides an important improvement over existing or potential therapies, such as introduction of HFE expression cassettes through lentivirus delivery and integration. Gene editing has the advantage of precise genome modification and lower adverse effects, or example, the mutation can be corrected by the insertions or deletions that arise due to the NHEJ repair pathway. If the patient's HFE gene has an inserted or deleted base, a targeted cleavage can result in a NHEJ-mediated insertion or deletion that restores the frame. Missense mutations can also be corrected through NHEJ-mediated correction using one or more guide RNA. The ability or likelihood of the cut(s) to correct the mutation can be designed or evaluated based on the local sequence and micro-homologies. NHEJ can also be used to delete segments of the gene, either directly or by altering splice donor or acceptor sites through cleavage by one gRNA targeting several locations, or several gRNAs. This may be useful if an amino acid, domain or exon contains the mutations and can be removed or inverted, or if the deletion otherwise restored function to the protein. Pairs of guide strands have been used for deletions and corrections of inversions.

Alternatively, the donor for correction by HDR contains the corrected sequence with small or large flanking homology arms to allow for annealing. HDR is essentially an error-free mechanism that uses a supplied homologous DNA sequence as a template during DSB repair. The rate of HDR is a function of the distance between the mutation and the cut site so choosing overlapping or nearby target sites is important. Templates can include extra sequences flanked by the homologous regions or can contain a sequence that differs from the genomic sequence, thus allowing sequence editing.

In addition to correcting mutations by NHEJ or HDR, a range of other options are possible. If there are small or large deletions or multiple mutations, a cDNA can be knocked in that contains the exons affected. A full length cDNA can be knocked into any "safe harbor"—i.e., non-deleterious insertion point that is not the HFE gene itself-, with or without suitable regulatory sequences. If this construct is knocked-in near the HFE regulatory elements, it should have physiological control, similar to the normal gene. Two or more (e.g., a pair) nucleases can be used to delete mutated gene regions, though a donor would usually have to be provided to restore function. In this case two gRNA and one donor sequence would be supplied.

Provided herein are cellular, ex vivo and in vivo methods for using genome engineering tools to create permanent changes to the genome by: 1) correcting, by insertions or deletions that arise due to the NHEJ pathway, one or more mutations within or near the HFE gene or other DNA sequences that encode regulatory elements of the HFE gene, 2) correcting, by HDR, one or more mutations within or near the HFE gene or other DNA sequences that encode regulatory elements of the HFE gene, or 3) deletion of the mutant region and/or knocking-in HFE cDNA or minigene into the gene locus or a safe harbour locus, such as, e.g., targeting exons 1-2 (exon 1, intron 1, and exon 2) of an AAVS1 (PPP1R12C) gene, an ALB gene, an Angptl3 gene, an ApoC3 gene, an ASGR2 gene, a CCR5 gene, a FIX (F9) gene, a G6PC gene, a Gys2 gene, an HGD gene, an Lp(a) gene, a Pcsk9 gene, a Serpina1 gene, a TF gene, and/or a TTR gene, or 4) deletion of the mutant region and knocking-in HFE cDNA or a minigene (comprised of one or more exons and introns or natural or synthetic introns) into the first exon of HGD, leading to disruption of HGD expression. HGD−/− hepatocytes have proliferation advantage when FAH activity is absent or reduced. Inhibition of FAH can be achieved by treatment with shRNA (AAV) targeting FAH, or siRNA (LNP formulated, or conjugate with GalNAc, or with cholesterol) or treatment with CEHPOBA (see e.g., Paulk et al. "In vivo selection of transplanted hepatocytes by pharmacological inhibition of fumarylacetoacetate hydrolase in wild-type mice." Mol Ther 2012, 20(10):1981-1987). Assessment of efficiency of HDR mediated knock-in of cDNA into the first exon can utilize cDNA knock-in into "safe harbor" sites such as: single-stranded or double-stranded DNA having homologous arms to one of the following regions, for example: ApoC3 (chr11:116829908-116833071), Angptl3 (chr1:62,597,487-62,606,305), Serpina1 (chr14:94376747-94390692), Lp(a) (chr6:160531483-160664259), Pcsk9 (chr1:55,039,475-55,064,852), FIX (chrX:139,530,736-139,563,458), ALB (chr4:73,404,254-73,421,411), TTR (chr18:31,591,766-31,599,023), TF (chr3:133,661,997-133,779,005), Gys2 (chr12:21,536,188-21,604,857), AAVS1(PPP1R12C) (chr19:55,090,912-55,117,599), HGD (chr3:120,628, 167-120,682,570), CCR5 (chr3:46,370,854-46,376,206), ASGR2 (chr17:7,101, 322-7,114,310), G6PC (chr17: 42,900,796-42,914,432), 5'UTR correspondent to ASS1 or alternative 5' UTR, complete CDS of HFE and 3' UTR of HFE or modified 3' UTR and at least 80 nt of the first intron, alternatively same DNA template sequence will be delivered by AAV. Both the HDR and knock-in strategies utilize a donor DNA template in Homology-Directed Repair (HDR). HDR in either strategy may be accomplished by making one or more single-stranded breaks (SSBs) or one or more double-stranded breaks (DSBs) at specific sites in the genome by using one or more endonucleases.

Such methods use endonucleases, such as CRISPR-associated (Cas9, Cpf1 and the like) nucleases, to permanently delete, insert, edit or correct one or more mutations within or near the genomic locus of the HFE gene or other DNA sequences that encode regulatory elements of the HFE gene. In this way, examples set forth in the present disclosure can help to restore the reading frame or the wild-type sequence of, or otherwise correct, the gene with as few as a single treatment (rather than deliver potential therapies for the lifetime of the patient).

Provided herein are methods for treating a patient with HHC. An aspect of such method is an ex vivo cell-based therapy. For example, a patient specific induced pluripotent stem cell (iPSC) can be created. Then, the chromosomal DNA of these iPS cells can be edited using the materials and methods described herein. Next, the genome-edited iPSCs can be differentiated into hepatocytes. Finally, the hepatocytes can be implanted into the patient.

Another aspect of such method is an ex vivo cell-based therapy. For example, a biopsy of the patient's liver is performed. Then, a liver specific progenitor cell or primary hepatocyte is isolated from the biopsied material. Next, the chromosomal DNA of these liver specific progenitor cells or primary hepatocytes can be edited using the materials and methods described herein. Finally, the genome-edited liver specific progenitor cell or primary hepatocyte can be implanted into the patient.

Yet another aspect of such method is an ex vivo cell-based therapy. For example, a mesenchymal stem cell can be isolated from the patient, which can be isolated from the patient's bone marrow by performing a biopsy of the patient's bone marrow or isolated from peripheral blood. Next, the chromosomal DNA of these mesenchymal stem cells can be edited using the materials and methods described herein. Next, the genome-edited mesenchymal stem cells can be differentiated into hepatocytes. Finally, these hepatocytes can be implanted into the patient.

One advantage of an ex vivo cell therapy approach is the ability to conduct a comprehensive analysis of the therapeutic prior to administration. Nuclease-based therapeutics can have some level of off-target effects. Performing gene correction ex vivo allows one to characterize the corrected cell population prior to implantation. The present disclosure includes sequencing the entire genome of the corrected cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability. In contrast, other potential cell types, such as primary hepatocytes, are viable for only a few passages and difficult to clonally expand. Thus, manipulation of iPSCs for the treatment of HHC can be much easier, and can shorten the amount of time needed to make the desired genetic correction.

Methods can also include an in vivo based therapy. Chromosomal DNA of the cells in the patient is edited using the materials and methods described herein.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Also provided herein is a cellular method for editing the HFE gene in a cell by genome editing. For example, a cell can be isolated from a patient or animal. Then, the chromosomal DNA of the cell can be edited using the materials and methods described herein.

The methods provided herein, regardless of whether a cellular or ex vivo or in vivo method, can involve one or a combination of the following: 1) correcting, by insertions or deletions that arise due to the imprecise NHEJ pathway, one or more mutations within or near the HFE gene or other DNA sequences that encode regulatory elements of the HFE gene, 2) correcting, by HDR, one or more mutations within or near the HFE gene or other DNA sequences that encode regulatory elements of the HFE gene, or 3) deletion of the mutant region and/or knocking-in HFE cDNA into the gene locus or at a heterologous location in the genome (such as a safe harbor locus, such as, e.g., targeting exons 1-2 (exon 1, intron 1, and exon 2) of an AAVS1 (PPP1R12C) gene, an ALB gene, an Angptl3 gene, an ApoC3 gene, an ASGR2 gene, a CCR5 gene, a FIX (F9) gene, a G6PC gene, a Gys2 gene, an HGD gene, an Lp(a) gene, a Pcsk9 gene, a Serpina1 gene, a TF gene, and/or a TTR gene). Both the HDR and knock-in strategies utilize a donor DNA template in HDR. HDR in either strategy may be accomplished by making one or more single-stranded breaks (SSBs) or double-stranded breaks (DSBs) at specific sites in the genome by using one or more endonucleases.

For example, the NHEJ correction strategy can involve correcting a specific mutation in the HFE gene by inducing one single stranded break or double stranded break in the gene of interest with one or more CRISPR endonucleases and a gRNA (e.g., crRNA+tracrRNA, or sgRNA), or two or more single stranded breaks or double stranded breaks in the gene of interest with two or more CRISPR endonucleases and two or more sgRNAs. This approach can require development and optimization of sgRNAs and donor DNA molecules for the major variant of the HFE gene.

For example, the HDR correction strategy can involve correcting a specific mutation in the HFE gene by inducing one single stranded break or double stranded break in the gene of interest with one or more CRISPR endonucleases and a gRNA (e.g., crRNA+tracrRNA, or sgRNA), or two or more single stranded breaks or double stranded breaks in the gene of interest with one or more CRISPR endonucleases and two or more gRNAs, in the presence of a donor DNA template introduced exogenously to direct the cellular DSB response to Homology-Directed Repair (the donor DNA template can be a short single stranded oligonucleotide, a short double stranded oligonucleotide, a long single or double stranded DNA molecule). This approach can require development and optimization of gRNAs and donor DNA molecules for the major variant of the HFE gene.

For example, the knock-in strategy involves knocking-in HFE cDNA into the locus of the gene using a gRNA (e.g., crRNA+tracrRNA, or sgRNA) or a pair of gRNAs targeting upstream of or in the first or other exon and/or intron of the HFE gene, or in a safe harbor site (such as, e.g., exon 1-2 of, AAVS1 (PPP1R12C), ALB, Angptl3, ApoC3, ASGR2, CCR5, FIX (F9), G6PC, Gys2, HGD, Lp(a), Pcsk9, Serpinal, TF, and/or TTR). The donor DNA can be single or double stranded DNA having homologous arms to the human 6p21.3 region.

The advantages for the above strategies (correction and knock-in) are similar, including in principle both short and long term beneficial clinical and laboratory effects. The knock-in approach does provide one advantage over the correction approach—the ability to treat all patients versus only a subset of patients.

In addition to the above genome editing strategies, another strategy involves modulating expression, function, or activity of HFE by editing in the regulatory sequence.

In addition to the editing options listed above, Cas9 or similar proteins can be used to target effector domains to the same target sites that can be identified for editing, or additional target sites within range of the effector domain. A range of chromatin modifying enzymes, methylases or demethylases can be used to alter expression of the target gene. One possibility is increasing the expression of the HFE protein if the mutation leads to lower activity. These types of epigenetic regulation have some advantages, particularly as they are limited in possible off-target effects.

A number of types of genomic target sites can be present in addition to mutations in the coding and splicing sequences.

The regulation of transcription and translation implicates a number of different classes of sites that interact with cellular proteins or nucleotides. Often the DNA binding sites of transcription factors or other proteins can be targeted for mutation or deletion to study the role of the site, though they can also be targeted to change gene expression. Sites can be added through non-homologous end joining NHEJ or direct genome editing by HDR. Increased use of genome sequencing, RNA expression and genome-wide studies of transcription factor binding have increased our ability to identify how the sites lead to developmental or temporal gene regulation. These control systems can be direct or can involve extensive cooperative regulation that can require the integration of activities from multiple enhancers. Transcription factors typically bind 6-12 bp-long degenerate DNA sequences. The low level of specificity provided by individual sites suggests that complex interactions and rules are involved in binding and the functional outcome. Binding sites with less degeneracy can provide simpler means of regulation. Artificial transcription factors can be designed to specify longer sequences that have less similar sequences in the genome and have lower potential for off-target cleavage. Any of these types of binding sites can be mutated, deleted or even created to enable changes in gene regulation or expression (Canver, M. C. et al., *Nature* (2015)).

Another class of gene regulatory regions having these features is microRNA (miRNA) binding sites. miRNAs are non-coding RNAs that play key roles in post-transcriptional gene regulation. miRNA can regulate the expression of 30% of all mammalian protein-encoding genes. Specific and potent gene silencing by double stranded RNA (RNAi) was discovered, plus additional small noncoding RNA (Canver, M. C. et al., *Nature* (2015)). The largest class of noncoding RNAs important for gene silencing are miRNAs. In mammals, miRNAs are first transcribed as a long RNA transcripts, which can be separate transcriptional units, part of protein introns, or other transcripts. The long transcripts are called primary miRNA (pri-miRNA) that include imperfectly base-paired hairpin structures. These pri-miRNA can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported, into the mature 19-25 nucleotide miRNA:miRNA* duplexes. The miRNA strand with lower base pairing stability (the guide strand) can be loaded onto the RNA-induced silencing complex (RISC). The passenger guide strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. *Cell* 136, 215-233 (2009); Saj, A. & Lai, E. C. *Curr Opin Genet Dev* 21, 504-510 (2011)).

miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual transcript can be targeted by many different miRNAs. More than 28645 microRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. *Genes Dev* 24, 1339-1344 (2010); Posadas, D. M. & Carthew, R. W. *Curr Opin Genet Dev* 27, 1-6 (2014)).

miRNA can also be important in a large number of human diseases that are associated with abnormal miRNA expression. This association underscores the importance of the miRNA regulatory pathway. Recent miRNA deletion studies have linked miRNA with regulation of the immune responses (Stem-Ginossar, N. et al., *Science* 317, 376-381 (2007)).

miRNA also have a strong link to cancer and can play a role in different types of cancer. miRNAs have been found to be downregulated in a number of tumors. miRNA can be important in the regulation of key cancer-related pathways, such as cell cycle control and the DNA damage response, and can therefore be used in diagnosis and can be targeted clinically. MicroRNAs can delicately regulate the balance of angiogenesis, such that experiments depleting all microRNAs suppresses tumor angiogenesis (Chen, S. et al., *Genes Dev* 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. *Cell Cycle* 6, 1001-1005 (2007)). The majority of studies have used treatment with chromatin remodeling drugs to reveal epigenetically silenced miRNAs.

In addition to their role in RNA silencing, miRNA can also activate translation (Posadas, D. M. & Carthew, R. W. *Curr Opin Genet Dev* 27, 1-6 (2014)). Knocking out these sites may lead to decreased expression of the targeted gene, while introducing these sites may increase expression.

Individual miRNA can be knocked out most effectively by mutating the seed sequence (bases 2-8 of the microRNA), which can be important for binding specificity. Cleavage in this region, followed by mis-repair by NHEJ can effectively abolish miRNA function by blocking binding to target sites. miRNA could also be inhibited by specific targeting of the special loop region adjacent to the palindromic sequence. Catalytically inactive Cas9 can also be used to inhibit shRNA expression (Zhao, Y. et al., *Sci Rep* 4, 3943 (2014)). In addition to targeting the miRNA, the binding sites can also be targeted and mutated to prevent the silencing by miRNA.

Human Cells

For ameliorating HHC, as described and illustrated herein, the principal targets for gene editing are human cells. For example, in the ex vivo methods, the human cells can be somatic cells, which after being modified using the techniques as described, can give rise to hepatocytes or progenitor cells. For example, in the in vivo methods, the human cells can be hepatocytes, or cells from other affected organs.

By performing gene editing in autologous cells that are derived from and therefore already completely matched with the patient in need, it is possible to generate cells that can be safely re-introduced into the patient, and effectively give rise to a population of cells that can be effective in ameliorating one or more clinical conditions associated with the patient's disease.

Progenitor cells (also referred to as stem cells herein) are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell that, itself, is derived from a multipotent cell, and so on. While each of these multipotent cells may be considered stem cells, the range of cell types that each can give rise to may vary considerably. Some differentiated cells also have the capacity to give rise to cells of greater developmental potential. Such capacity may be natural or may be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and may or may not retain the capacity to proliferate further.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompasse complete reversion of the differentiation state of a differentiated cell (e.g., a somatic cell) to a pluripotent state or a multipotent state. Reprogramming can encompasse complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or PS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-4 (also known as Oct-3/4 or Pouf51), SoxI, Sox2, Sox3, Sox 15, Sox 18, NANOG, Klf1, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008): Huangfu et al, Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vonnostat) and other hydroxamic acids), BML-210, Depudecin (e.g., (−)-Depudecin), HC Toxin, Nullscript (4-(1,3-Dioxo-IH,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin. Sodium Butyrate, pivaloyloxymethyl butyrate (Pivanex, AN-9), Trapoxin B, Chlamydocin, Depsipeptide (also known as FR901228 or FK228), benzamides (e.g., Cl-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-CI-UCHA (e.g., 6-(3-chlorophenylureido) caproic hydroxamic acid), AOE (2-amino-8-oxo-9, 10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecatl, Esgl, Eras, Gdf3, Fgf4, Cripto, Daxl, Zpf296, Slc2a3, Rexl, Utfl, and Natl. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Hepatocytes

The genetically engineered human cells described herein can be hepatocytes. A hepatocyte is a cell of the main parenchymal tissue of the liver. Hepatocytes make up 70-85% of the liver's mass. These cells are involved in: protein synthesis; protein storage; transformation of carbohydrates; synthesis of cholesterol, bile salts and phospholipids; detoxification, modification, and excretion of exogenous and endogenous substances; and initiation of formation and secretion of bile.

Although the HFE gene is expressed in various tissues, iron is primarily deposed in hepatocytes and thus correction of the HFE gene should be primarily targeted to hepatocytes and the liver.

Creating Patient Specific iPSCs

One step of the ex vivo methods of the present disclosure can involve creating a patient specific PS cell, patient specific iPS cells, or a patient specific PS cell line. There are many established methods in the art for creating patient specific PS cells, as described in Takahashi and Yamanaka 2006; Takahashi, Tanabe et al 2007. For example, the creating step can comprise: isolating a somatic cell, such as a skin cell or fibroblast, from the patient; and introducing a set of pluripotency-associated genes into the somatic cell in order to induce the cell to become a pluripotent stem cell. The set of pluripotency-associated genes can be one or more of the genes selected from the group consisting of OCT4, SOX2, KLF4, Lin28, NANOG, and cMYC Performing a Biopsy or Aspirate of the Patient's Bone Marrow A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a liver biopsy, a needle is injected into the liver through the skin or the belly, capturing the liver tissue. For example, in a bone marrow aspirate, a large needle is used to enter the pelvis bone to collect bone marrow.

Isolating a Liver Specific Progenitor Cell or Primary Hepatocyte

Liver specific progenitor cells and primary hepatocytes may be isolated according to any method known in the art. For example, human hepatocytes are isolated from fresh surgical specimens (e.g., an autologous sample). Healthy liver tissue is used to isolate hepatocytes by collagenase digestion. The obtained cell suspension is filtered through a 100-mm nylon mesh and sedimented by centrifugation at 50 g for 5 minutes, resuspended, and washed two to three times in cold wash medium. Human liver stem cells are obtained by culturing under stringent conditions of hepatocytes obtained from fresh liver preparations. Hepatocytes seeded on collagen-coated plates are cultured for 2 weeks. After 2 weeks, surviving cells are removed, and characterized for expression of stem cells markers (Herrera et al, STEM CELLS 2006; 24: 2840-2850).

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll™ density gradient. Cells, such as blood cells, liver cells, interstitial cells, macrophages, mast cells, and thymocytes, can be separated using density gradient centrifugation media, Percoll™. The cells can then be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Genome Editing

Genome editing generally refers to the process of modifying the nucleotide sequence of a genome, preferably in a precise or pre-determined manner. Examples of methods of genome editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as HDR and NHEJ. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ", in which the genetic outcome is similar to NHEJ in that small deletions and insertions can occur at the cleavage site. MMEJ can make use of homologous sequences of a few basepairs flanking the DNA break site to drive a more favored DNA end joining repair outcome, and recent reports have further elucidated the molecular mechanism of this process. In some instances it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair or non-homologous end joining or alternative non-homologous end joining (A-NHEJ) or microhomology-mediated end joining). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that can be homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science*, 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceeded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 1B:
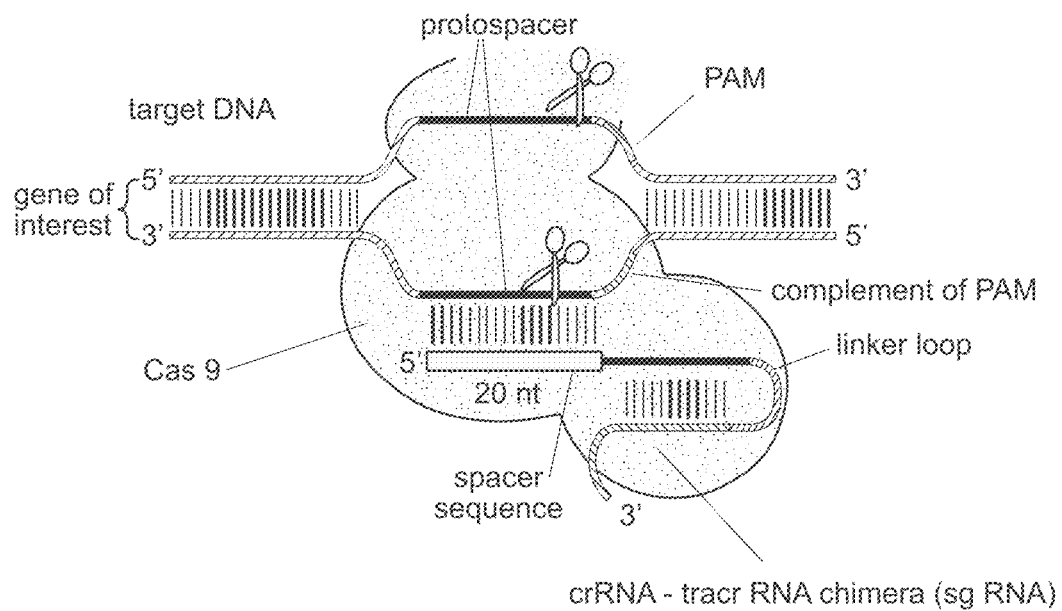
FIG. 1B is a depiction of the type II CRISPR/Cas system.

Exemplary CRISPR/Cas polypeptides include the Cas9 polypeptides in FIG. 1 of Fonfara et al., *Nucleic Acids Research*, 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA. The site-directed can be administered to a cell or a patient as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In the CRISPR/Cas or CRISPR/Cpf1 systems disclosed herein, the site-directed polypeptide can be an endonuclease, such as a DNA endonuclease.

A site-directed polypeptide can comprises a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally-occurring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways (e.g., HDR or NHEJ or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few basepairs flanking the cleavage site to drive a favored end-joining DNA repair outcome. In some instances it may be possible to predict likely repair outcomes based on analysis of potential micro-homologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas et al., *Nucleic Acids Res*, 39(21): 9275-9282 (2011)], and various other site-directed polypeptides. The site-directed polypeptide can comprise at least 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprises at most: 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a single-strand break (SSB) on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. One skilled in the art will recognize that mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases".

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., S. pyogenes), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., S. pyogenes), and two nucleic acid cleaving domains, wherein one or both of the nucleic acid cleaving domains comprise at least 50% amino acid identity to a nuclease domain from Cas9 from a bacterium (e.g., S. pyogenes).

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., S. pyogenes), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., S. pyogenes), and two nucleic acid cleaving domains (i.e., a HNH domain and a RuvC domain), wherein one of the nuclease domains comprises mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in SEQ ID NOs: 1-64,980 of the Sequence Listing, shown with the genome location of their target sequence and the associated Cas9 cut site, wherein the genome location is based on the GRCh38/hg38 human genome assembly.

Each guide RNA can be designed to include a spacer sequence complementary to its genomic target sequence. For example, each of the spacer sequences in SEQ ID NOs: 1-64,980 of the Sequence Listing can be put into a single RNA chimera or a crRNA (along with a corresponding tracrRNA). See Jinek et al., Science, 337, 816-821 (2012) and Deltcheva et al., Nature, 471, 602-607 (2011).

The genome-targeting nucleic acid can be a double-molecule guide RNA. The genome-targeting nucleic acid can be a single-molecule guide RNA.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

A single-molecule guide RNA (sgRNA) in a Type V system can comprise, in the 5' to 3' direction, a minimum CRISPR repeat sequence and a spacer sequence.

The sgRNA can comprise a 20 nucleotide spacer sequence at the 5' end of the sgRNA sequence. The sgRNA can comprise a less than a 20 nucleotide spacer sequence at the 5' end of the sgRNA sequence. The sgRNA can comprise a more than 20 nucleotide spacer sequence at the 5' end of the sgRNA sequence. The sgRNA can comprise a variable length spacer sequence with 17-30 nucleotides at the 5' end of the sgRNA sequence (see Table 1).

The sgRNA can comprise no uracil at the 3'end of the sgRNA sequence, such as in SEQ ID NO. 64,985 of Table 1. The sgRNA can comprise one or more uracil at the 3'end of the sgRNA sequence, such as in SEQ ID NOs. 64,986-64,987 in Table 1. For example, the sgRNA can comprise 1 uracil (U) at the 3'end of the sgRNA sequence. The sgRNA can comprise 2 uracil (UU) at the 3'end of the sgRNA sequence. The sgRNA can comprise 3 uracil (UUU) at the 3'end of the sgRNA sequence. The sgRNA can comprise 4 uracil (UUUU) at the 3'end of the sgRNA sequence. The sgRNA can comprise 5 uracil (UUUUU) at the 3'end of the sgRNA sequence. The sgRNA can comprise 6 uracil (UUUUUU) at the 3'end of the sgRNA sequence. The sgRNA can comprise 7 uracil (UUUUUUU) at the 3'end of the sgRNA sequence. The sgRNA can comprise 8 uracil (UUUUUUUU) at the 3'end of the sgRNA sequence.

The sgRNA can be unmodified or modified. For example, modified sgRNAs can comprise one or more 2'-O-methyl phosphorothioate nucleotides. For example, modified sgRNAs can comprise 2'-O-methyl phosphorothioate nucleotides as the first 3 nucleotides and 2'-O-methyl phosphorothioate nucleotides as the last 3 nucleotides, such as in SEQ ID NO. 64,984 in Table 1 where "*" indicates 2'-O-methyl phosphorothioate nucleotides. The first 3 nucleotides in the $n_{(17-30)}$ region of SEQ ID NO. 64,987 can be 2'-O-methyl phosphorothioate nucleotides (i.e.: n*). The last 3 nucleotides within the $u_{(1-8)}$ region of SEQ ID NO. 64,987 can be 2'-O-methyl phosphorothioate urasils (i.e.: u*). In certain examples where the $u_{(1-8)}$ region of SEQ ID NO. 64,987 contains less than 3 urasil, one or two nucleotides prior to the $u_{(1-8)}$ region can be 2'-O-methyl phosphorothioate nucleotides such that the last three nucleotides of the sequence are 2'-O-methyl phosphorothioate nucleotides.

a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include, a 5' cap (e.g., a 7-methylguanylate cap (m7 G)), a riboswitch sequence (e.g.,

TABLE 1

| SEQ ID NO. | sgRNA sequence |
|---|---|
| 64,983 | nnnnnnnnnnnnnnnnnnnnguuuuagagcuagaaauagcaaguuaaaauaaggcuaguccguua ucaacuugaaaaaguggcaccgagucggugcuuuu |
| 64,984 | n*n*n*nnnnnnnnnnnnnnnnnnnguuuuagagcuagaaauagcaaguuaaaauaaggcuaguccg uuaucaacuugaaaaaguggcaccaauucggugcun*n*n* |
| 64,985 | nnnnnnnnnnnnnnnnnnnnguuuuagagcuagaaauagcaaguuaaaauaaggcuaguccguua ucaacuugaaaaaguggcaccgagucggugc |
| 64,986 | $n_{(17-30)}$guuuuagagcuagaaauagcaaguuaaaauaaggcuaguccguuaucaacuugaaaaagu ggcaccgagucggugcu$_{(1-8)}$ |
| 64,987 | $n_{(17-30)}$guuuuagagcuagaaauagcaaguuaaaauaaggcuaguccguuaucaacuugaaaaagu ggcaccgagucggugcu$_{(1-8)}$ |

By way of illustration, guide RNAs used in the CRISPR/Cas/Cpf1 system, or other smaller RNAs, can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some examples of genome-targeting nucleic acids, a spacer extension sequence can modify activity, provide stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can have to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-NNNNNNNNNNNNNNNNNNNNNRG-3' (SEQ ID NO. 64,981), the target nucleic acid can comprise the sequence that corresponds to the Ns, wherein N is any nucleotide, and the underlined NRG sequence is the S. pyogenes PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which may be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. pyogenes).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from S. pyogenes) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge can comprise at most one wobble pairing. A bulge can comprise at least one purine nucleotide. A bulge can comprise at least 3 purine nucleotides. A bulge sequence can comprises at least 5 purine nucleotides. A bulge sequence can comprise at least one guanine nucleotide. In some examples, a bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from S. pyogenes) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. pyogenes) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence may be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases. DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

Genome Engineering Strategies to Correct Cells by Deletion, Insertion, or Correction of One or More Mutations within or Near the HFE Gene, or by Knocking-In HFE cDNA into the Locus of the Corresponding HFE Gene or Safe Harbor Site The methods of the present disclosure can involve correction of one or both of the mutant alleles. Gene editing to correct the mutation has the advantage of restoration of correct expression levels and temporal control. Sequencing the patient's HFE alleles allows for design of the gene editing strategy to best correct the identified mutation(s).

A step of the ex vivo methods of the present disclosure can comprise editing/correcting the patient specific iPSC cells using genome engineering. Alternatively, a step of the ex vivo methods of the present disclosure can comprise editing/correcting the liver specific progenitor cell, primary hepatocyte, or mesenchymal stem cell. Likewise, a step of the in vivo methods of the present disclosure can comprise editing/correcting the cells in a HHC patient using genome engineering. Similarly, a step in the cellular methods of the present disclosure can comprise editing/correcting the HFE gene in a human cell by genome engineering.

HHC patients exhibit one or more mutations in the HFE gene. Therefore, different patients will generally require different correction strategies. Any CRISPR endonuclease may be used in the methods of the present disclosure, each CRISPR endonuclease having its own associated PAM, which may or may not be disease specific. For example, gRNA spacer sequences for targeting the HFE gene with a CRISPR/Cas9 endonuclease from *S. pyogenes* have been identified in SEQ ID NOs. 1-4,455 of the Sequence Listing. gRNA spacer sequences for targeting the HFE gene with a CRISPR/Cas9 endonuclease from *S. aureus* have been identified in SEQ ID NOs. 4,456-4,979 of the Sequence Listing. gRNA spacer sequences for targeting the HFE gene with a CRISPR/Cas9 endonuclease from *S. thermophilus* have been identified in SEQ ID NOs. 4,980-5,139 of the Sequence Listing. gRNA spacer sequences for targeting the HFE gene with a CRISPR/Cas9 endonuclease from *T. denticola* have been identified in SEQ ID NOs. 5,140-5,192 of the Sequence Listing. gRNA spacer sequences for targeting the HFE gene with a CRISPR/Cas9 endonuclease from *N. meningitides* have been identified in SEQ ID NOs. 5,193-5,617 of the Sequence Listing. gRNA spacer sequences for targeting the HFE gene with a CRISPR/Cpf1 endonuclease from Acidominococcus, Lachnospiraceae, and *Franciscella Novicida* have been identified in SEQ ID NOs. 5,618-10,121 of the Sequence Listing.

For example, the mutation can be corrected by the insertions or deletions that arise due to the imprecise NHEJ repair pathway. If the patient's HFE gene has an inserted or deleted base, a targeted cleavage can result in a NHEJ-mediated insertion or deletion that restores the frame. Missense mutations can also be corrected through NHEJ-mediated correction using one or more guide RNA. The ability or likelihood of the cut(s) to correct the mutation can be designed or evaluated based on the local sequence and micro-homologies. NHEJ can also be used to delete segments of the gene, either directly or by altering splice donor or acceptor sites through cleavage by one gRNA targeting several locations, or several gRNAs. This may be useful if an amino acid, domain or exon contains the mutations and can be removed or inverted, or if the deletion otherwise restored function to the protein. Pairs of guide strands have been used for deletions and corrections of inversions.

Alternatively, the donor for correction by HDR contains the corrected sequence with small or large flanking homology arms to allow for annealing. HDR is essentially an error-free mechanism that uses a supplied homologous DNA sequence as a template during DSB repair. The rate of HDR is a function of the distance between the mutation and the cut site so choosing overlapping or nearest target sites is important. Templates can include extra sequences flanked by the homologous regions or can contain a sequence that differs from the genomic sequence, thus allowing sequence editing.

In addition to correcting mutations by NHEJ or HDR, a range of other options are possible. If there are small or large deletions or multiple mutations, a cDNA can be knocked in that contains the exons affected. A full length cDNA can be knocked into any "safe harbor", but must use a supplied or other promoter. If this construct is knocked into the correct location, it will have physiological control, similar to the normal gene. Pairs of nucleases can be used to delete mutated gene regions, though a donor would usually have to be provided to restore function. In this case two gRNA would be supplied and one donor sequence.

Some genome engineering strategies involve correction of one or more mutations in or near the HFE gene, or deleting the mutant HFE DNA and/or knocking-in HFE cDNA into the locus of the corresponding gene or a safe harbor locus by HDR, which is also known as homologous recombination (HR). Homology directed repair can be one strategy for treating patients that have one or more mutations in or near the HFE gene. These strategies can restore the HFE gene and reverse, treat, and/or mitigate the diseased state. These strategies can require a more custom approach based on the location of the patient's mutation(s) Donor nucleotides for correcting mutations often are small (<300 bp). This is advantageous, as HDR efficiencies may be inversely related to the size of the donor molecule. Also, it is expected that the donor templates can fit into size constrained adeno-associated virus (AAV) molecules, which have been shown to be an effective means of donor template delivery.

Homology direct repair is a cellular mechanism for repairing double-stranded breaks (DSBs). The most common form is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in $10^6$ cells receiving a homologous donor alone. The rate of HDR at a particular nucleotide is a function of the distance to the cut site, so choosing overlapping or nearest target sites is important. Gene editing offers the advantage over gene addition, as correcting in situ leaves the rest of the genome unperturbed.

Supplied donors for editing by HDR vary markedly but can contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides range in size from less than 100 nt to over many kb, though longer ssDNA can also be generated and used. Double-stranded donors can be used, including PCR amplicons, plasmids, and mini-circles. In general, it has been found that an AAV vector can be a very effective means of delivery of a donor template, though the packaging limits for individual donors is <5 kb. Active transcription of the donor increased HDR three-fold, indicating the inclusion of promoter may increase conversion. Conversely, CpG methylation of the donor decreased gene expression and HDR.

In addition to wildtype endonucleases, such as Cas9, nickase variants exist that have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nano-particle, micro-injection, or viral transduction. A range of tethering options has been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV.

Without a donor present, the ends from a DNA break or ends from different breaks can be joined using the several nonhomologous repair pathways in which the DNA ends are joined with little or no base-pairing at the junction. In addition to canonical NHEJ, there are similar repair mechanisms, such as alt-NHEJ. If there are two breaks, the intervening segment can be deleted or inverted. NHEJ repair pathways can lead to insertions, deletions or mutations at the joints.

NHEJ was used to insert a 15-kb inducible gene expression cassette into a defined locus in human cell lines after nuclease cleavage. Maresca, M., Lin, V. G., Guo, N. & Yang, Y., *Genome Res* 23, 539-546 (2013).

In addition to genome editing by NHEJ or HDR, site-specific gene insertions have been conducted that use both the NHEJ pathway and HR. A combination approach may be applicable in certain settings, possibly including intron/exon borders. NHEJ may prove effective for ligation in the intron, while the error-free HDR may be better suited in the coding region.

The HFE gene contains 7 exons. Any one or more of the 7 exons or nearby introns can be repaired in order to correct a mutation and restore HFE protein activity. Alternatively, there are various mutations associated with HHC, which are a combination of insertions, deletions, missense, nonsense, frameshift and other mutations, with the common effect of inactivating the HFE gene. Any one or more of the mutations can be repaired in order to restore the inactive HFE gene expression. For example, one or more of the following pathological variants may be corrected: C282Y, H63D, S65C, or combinations thereof (See Table 2). As a further alternative, HFE cDNA can be knocked-in to the locus of the corresponding gene or knocked-in to a safe harbor site, such as AAVS1. In some examples, the methods can provide one gRNA or a pair of gRNAs that can be used to facilitate incorporation of a new sequence from a polynucleotide donor template to correct one or more mutations or to knock-in a part of or the entire HFE gene or cDNA.

TABLE 2

| Variant | Location | Variant type |
| --- | --- | --- |
| C282Y | 6: 26092913, rs1800562 | missense |
| H63D | 6: 26090951, rs1799945 | missense |
| S65C | 6: 26090957, rs1800730 | missense |

The methods can provide gRNA pairs that make a deletion by cutting the gene twice, one gRNA cutting at the 5' end of one or more mutations and the other gRNA cutting at the 3' end of one or more mutations that facilitates insertion of a new sequence from a polynucleotide donor template to replace the one or more mutations. The cutting can be accomplished by a pair of DNA endonucleases that each makes a DSB in the genome, or by multiple nickases that together make a DSB in the genome.

Alternatively, the methods can provide one gRNA to make one double-strand cut around one or more mutations that facilitates insertion of a new sequence from a polynucleotide donor template to replace the one or more mutations. The double-strand cut can be made by a single DNA endonuclease or multiple nickases that together make a DSB in the genome.

Illustrative modifications within the HFE gene include replacements within or near (proximal) to the mutations referred to above, such as within the region of less than 3 kb, less than 2 kb, less than 1 kb, less than 0.5 kb upstream or downstream of the specific mutation. Given the relatively wide variations of mutations in the HFE gene, it will be appreciated that numerous variations of the replacements referenced above (including without limitation larger as well as smaller deletions), would be expected to result in restoration of the HFE protein activity.

Such variants can include replacements that are larger in the 5' and/or 3' direction than the specific mutation in question, or smaller in either direction. Accordingly, by "near" or "proximal" with respect to specific replacements, it is intended that the SSB or DSB locus associated with a desired replacement boundary (also referred to herein as an endpoint) can be within a region that is less than about 3 kb from the reference locus noted. The SSB or DSB locus can be more proximal and within 2 kb, within 1 kb, within 0.5 kb, or within 0.1 kb. In the case of small replacement, the desired endpoint can be at or "adjacent to" the reference locus, by which it is intended that the endpoint can be within 100 bp, within 50 bp, within 25 bp, or less than about 10 bp to 5 bp from the reference locus.

Examples comprising larger or smaller replacements can be expected to provide the same benefit, as long as the HFE protein activity is restored. It is thus expected that many variations of the replacements described and illustrated herein can be effective for ameliorating HHC.

Another genome engineering strategy involves exon deletion. Targeted deletion of specific exons can be an attractive strategy for treating a large subset of patients with a single therapeutic cocktail. Deletions can either be single exon deletions or multi-exon deletions. While multi-exon deletions can reach a larger number of patients, for larger deletions the efficiency of deletion greatly decreases with increased size. Therefore, deletions range can be from 40 to 10,000 base pairs (bp) in size. For example, deletions can range from 40-100; 100-300; 300-500; 500-1,000; 1,000-2,000; 2,000-3,000; 3,000-5,000; or 5,000-10,000 base pairs in size.

As stated previously, the HFE gene contains 7 exons. Any one or more of the 7 exons, or aberrant intronic splice acceptor or donor sites, may be deleted in order to restore the HFE reading frame. In some embodiments, the methods provide gRNA pairs that can be used to delete exons 1, 2, 3, 4, 5, 6, 7 or any combinations thereof.

In order to ensure that the pre-mRNA is properly processed following deletion, the surrounding splicing signals can be deleted. Splicing donor and acceptors are generally within 100 base pairs of the neighboring intron. Therefore, in some examples, methods can provide all gRNAs that cut approximately +/−100-3100 bp with respect to each exon/intron junction of interest.

For any of the genome editing strategies, gene editing can be confirmed by sequencing or PCR analysis.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first nonlimiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another nonlimiting example of target sequence selection or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten basepairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce replacements that result in restoration of HFE protein activity, as well as the selection of specific target sequences within such regions that are designed to minimize off-target events relative to on-target events.

Nucleic Acid Modifications

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of nonlimiting illustrations of such uses, modifications of guide RNAs can be used to enhance the formation or stability of the CRISPR/Cas9/Cpf1 genome editing complex comprising guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach that can be used for generating chemically-modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2' O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone), $CH_2$—O—N ($CH_3$)—$CH_2$, $CH_2$—N($CH_3$)—N($CH_3$)—$CH_2$ and O—N($CH_3$)— $CH_2$—$CH_2$ backbones, wherein the native phosphodiester backbone is represented as O—P—O—CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243;

5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones: methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3$ $OCH_3$, $OCH_3O(CH_2)n$ $CH_3$, $O(CH_2)n$ $NH_2$, or $O(CH_2)n$ $CH_3$, where n is from 1 to about 10; C1 to C10 lower alkyl, alkoxyalkoxy, substituted lower alkyl, alkaryl or aralkyl; Cl; Br, CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino, polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-0-$CH_2CH_2OCH_3$, also known as 2'-O-(2-methoxyethyl)) (Martin et al, Helv. Chim. Acta, 1995, 78, 486). Other modifications include 2'-methoxy (2'-0-$CH_3$), 2'-propoxy (2'-$OCH_2$ $CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A, DNA Replication, W. H. Freeman & Co., San Francisco, pp 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096, and US Patent Application Publication 2003/0158403.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979, 4,948,882; 5,218,105; 5,525,465; 5,541,313, 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941, 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al, and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-1), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16: Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013), and references cited therein.

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

RNPs

The site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-1.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., Molecular Therapy—Nucleic Acids 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.
Delivery Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA encoding an endonuclease, can be delivered to a cell or a patient by a lipid nanoparticle (LNP).

A LNP refers to any particle having a diameter of less than 1000 nm, 500 nm, 250 nm, 200 nm. 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein 10 as a packaging cell): a rAAV genome, AAV rep and cap genes separate from (i.e., not in) the rAAV genome, and helper virus functions. The AAV rep and cap genes may be from any AAV serotype for which recombinant virus can be derived, and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, international patent application publication number WO 01/83692. See Table 3.

TABLE 3

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et a. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. See Table 4.

TABLE 4

| Tissue/Cell Type | Serotype |
| --- | --- |
| Liver | AAV8, AA3, AA5, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2, AAV8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

In some cases, Cas9 mRNA, sgRNA targeting one or two loci in the HFE gene, and donor DNA can each be separately formulated into lipid nanoparticles, or are all co-formulated into one lipid nanoparticle.

In some cases, Cas9 mRNA can be formulated in a lipid nanoparticle, while sgRNA and donor DNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA Genetically Modified Cells The term "genetically modified cell" refers to a cell that comprises at least one genetic modification introduced by genome editing (e.g., using the CRISPR/Cas9/Cpf1 system). In some ex vivo examples herein, the genetically modified cell can be genetically modified progenitor cell. In some in vivo examples herein, the genetically modified cell can be a genetically modified liver cell. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure restoration of the HFE gene or protein expression or activity, for example Western Blot analysis of the HFE protein or quantifying HFE mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating hereditary haemochromatosis.

The term "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Differentiation of Genome-Edited iPSCs into Hepatocytes

Another step of the ex vivo methods of the present disclosure can comprise differentiating the genome-edited iPSCs into hepatocytes. The differentiating step can be performed according to any method known in the art. For example, hiPSC are differentiated into definitive endoderm using various treatments, including activin and B27 supplement (Life Technology). The definitive endoderm is further differentiated into hepatocyte, the treatment includes: FGF4, HGF, BMP2, BMP4, Oncostatin M, Dexametason, etc (Duan et al, STEM CELLS; 2010; 28:674-686. Ma et al, STEM CELLS TRANSLATIONAL MEDICINE 2013; 2:409-419).

Differentiation of Genome-Edited Mesenchymal Stem Cells into Hepatocytes

Another step of the ex vivo methods of the present disclosure can comprise differentiating the genome-edited mesenchymal stem cells into hepatocytes. The differentiating step can be performed according to any method known in the art. For example, hMSC are treated with various factors and hormones, including insulin, transferrin, FGF4, HGF, bile acids (Sawitza I et al, Sci Rep. 2015; 5: 13320).

Implanting Cells into Patients

Another step of the ex vivo methods of the present disclosure can comprise implanting liver specific progenitor cells or primary hepatocytes into patients. This implanting step can be accomplished using any method of implantation known in the art. For example, the genetically modified cells can be injected directly in the patient's liver or otherwise administered to the patient. The genetically modified cells may be purified ex vivo using a selected marker.

Pharmaceutically Acceptable Carriers

The ex vivo methods of administering progenitor cells to a subject contemplated herein can involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Administration & Efficacy

The terms "administering," "introducing" and "transplanting" are used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny, can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of myogenic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of HHC, e.g., prior to the development of abdominal pain, weakness, lethargy, and weight loss, cirrhosis, progressive increase in skin pigmentation, diabetes mellitus, congestive heart failure, and/or arrhythmias, arthritis, and hypogonadism. Accordingly, the prophylactic administration of a liver progenitor cell population serves to prevent hereditary haemochromatosis.

When provided therapeutically, liver progenitor cells are provided at (or after) the onset of a symptom or indication of hereditary haemochromatosis, e.g., upon the onset of disease.

The liver progenitor cell population being administered according to the methods described herein can comprise allogeneic liver progenitor cells obtained from one or more donors. "Allogeneic" refers to a liver progenitor cell or biological samples comprising liver progenitor cells obtained from one or more different donors of the same species, where the genes at one or more loci are not identical. For example, a liver progenitor cell population being administered to a subject can be derived from one more unrelated donor subjects, or from one or more nonidentical siblings. In some cases, syngeneic liver progenitor cell populations can be used, such as those obtained from genetically identical animals, or from identical twins. The liver progenitor cells can be autologous cells; that is, the liver progenitor cells are obtained or isolated from a subject and administered to the same subject, i.e., the donor and recipient are the same.

The term "effective amount" refers to the amount of a population of progenitor cells or their progeny needed to prevent or alleviate at least one or more signs or symptoms of HHC, and relates to a sufficient amount of a composition to provide the desired effect, e.g., to treat a subject having HHC. The term "therapeutically effective amount" therefore refers to an amount of progenitor cells or a composition comprising progenitor cells that is sufficient to promote a particular effect when administered to a typical subject, such as one who has or is at risk for HHC. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells comprises at least $10^2$ progenitor cells, at least $5 \times 10^2$ progenitor cells, at least $10^3$ progenitor cells, at least $5 \times 10^3$ progenitor cells, at least $10^4$ progenitor cells, at least $5 \times 10^4$ progenitor cells, at least $10^5$ progenitor cells, at least $2 \times 10^5$ progenitor cells, at least $3 \times 10^5$ progenitor cells, at least $4 \times 10^5$ progenitor cells, at least $5 \times 10^5$ progenitor cells, at least $6 \times 10^5$ progenitor cells, at least $7 \times 10^5$ progenitor cells, at least $8 \times 10^5$ progenitor cells, at least $9 \times 10^5$ progenitor cells, at least $1 \times 10^6$ progenitor cells, at least $2 \times 10^6$ progenitor cells, at least $3 \times 10^6$ progenitor cells, at least $4 \times 10^6$ progenitor cells, at least $5 \times 10^6$ progenitor cells, at least $6 \times 10^6$ progenitor cells, at least $7 \times 10^6$ progenitor cells, at least $8 \times 10^6$ progenitor cells, at least $9 \times 10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

Modest and incremental increases in the levels of functional HFE expressed in cells of patients having HHC can be beneficial for ameliorating one or more symptoms of the disease, for increasing long-term survival, and/or for reducing side effects associated with other treatments. Upon administration of such cells to human patients, the presence of liver progenitors that are producing increased levels of functional HFE is beneficial. In some cases, effective treatment of a subject gives rise to at least about 3%, 5% or 7% functional HFE relative to total HFE in the treated subject. In some examples, functional HFE will be at least about 10% of total HFE. In some examples, functional HFE will be at least about 20% to 30% of total HFE. Similarly, the introduction of even relatively limited subpopulations of cells having significantly elevated levels of functional HFE can be beneficial in various patients because in some situations normalized cells will have a selective advantage relative to diseased cells. However, even modest levels of liver progenitors with elevated levels of functional HFE can be beneficial for ameliorating one or more aspects of HHC in patients. In some examples, about 10%, about 20%, about 30%, about 40%, about 50%, about 60%, about 70%, about 80%, about 90% or more of the liver progenitors in patients to whom such cells are administered are producing increased levels of functional HFE.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1 \times 10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of HHC can be determined by the skilled clinician. However, a treatment is considered "effective treatment," if any one or all of the signs or symptoms of, as but one example, levels of functional HFE are altered in a beneficial manner (e.g., increased by at least 10%); or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with HHC by increasing the amount of functional HFE in the individual. Early signs typically associated with HHC include for example, abdominal pain, weakness, lethargy, and weight loss, cirrhosis, progressive increase in skin pigmentation, diabetes mellitus, congestive heart failure, and/or arrhythmias, arthritis, and hypogonadism.

Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide; and (2) a reagent for reconstitution and/or dilution of the vector.

In any of the above kits, the kit can comprise a single-molecule guide genome-targeting nucleic acid. In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Other Possible Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9. Cas9 cleavage also requires an adjacent motif, the PAM, which differs between different CRISPR systems. Cas9 from *Streptococcus pyogenes* cleaves using a NGG PAM, CRISPR from *Neissera meningitidis* can cleave at sites with PAMs including NNNNGATT, NNNNNGTTT and NNNNGCTT. A number of other Cas9 orthologs target protospacer adjacent to alternative PAMs.

CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nulceases. However, in order to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Nat Acad Sci USA* 96(6):2758-63 (1999); Dreier B et al., *J Mol Biol.* 303(4):489-502 (2000); Liu Q et al., *J Biol Chem.* 277(6):3850-6 (2002): Dreier et al., *J Biol Chem* 280(42): 35588-97 (2005); and Dreier et al., *J Biol Chem.* 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single basepair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefitted from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, *Science* 326(5959):1509-12 (2009); Mak et al., *Science* 335(6069):716-9 (2012); and Moscou et al., *Science* 326(5959):1501 (2009). The use of TALENs based on the "Golden Gate" platform, or cloning scheme, has been described by multiple groups; see, e.g., Cermak et al., *Nucleic Acids Res.* 39(12):e82 (2011); Li et al., *Nucleic Acids Res.* 39(14):6315-25(2011); Weber et al., *PLoS One.* 6(2):e16765 (2011); Wang et al., *J Genet Genomics* 41(6): 339-47, Epub 2014 May 17 (2014); and Cermak T et al., *Methods Mol Biol.* 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including LAGLI-DADG (SEQ ID NO. 64,982), GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., *Glycobiology* 24(8):663-80 (2014); Belfort and Bonocora, *Methods Mol Biol.* 1123: 1-26 (2014); Hafez and Hausner, *Genome* 55(8):553-69 (2012); and references cited therein.

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., *NAR* 42: 2591-2601 (2014); Kleinstiver et al., *G3* 4:1155-65 (2014); and Boissel and Scharenberg, *Methods Mol. Biol.* 1239:171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., NAR 42, 8816-29 (2014). It is anticipated that other combinations of existing nuclease-based approaches will evolve and be useful in achieving the targeted genome modifications described herein.

dCas9-FokI or dCpf1-Fok1 and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., *Nature Biotech* 32: 569-76 (2014); and Guilinger et al., *Nature Biotech*. 32: 577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Methods and Compositions of the Invention

Accordingly, the present disclosure relates in particular to the following non-limiting inventions: In a first method, Method 1, the present disclosure provides a method for editing an HFE gene in a human cell by genome editing, the method comprising: introducing into the human cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene and results in restoration of HFE protein activity.

In another method, Method 2, the present disclosure provides an ex vivo method for inserting a haemochromatosis (HFE) gene in a human cell by genome editing, the method comprising: introducing into the human cell one or more deoxyribonucleic acid (DNA) endonucleases to effect one or more single-strand breaks (SSBs) or double-strand breaks (DSBs) within or near a safe harbor locus that results in a permanent insertion of the HFE gene, and results in restoration of HFE protein activity.

In another method, Method 3, the present disclosure provides an ex vivo method for treating a patient with HHC, the method comprising: creating a patient specific induced pluripotent stem cell (iPSC); editing within or near an HFE gene or other DNA sequences that encode regulatory elements of the HFE gene of the iPSC, or editing within or near a safe harbor locus of the iPSC; differentiating the genome-edited iPSC into a hepatocyte; and implanting the hepatocyte into the patient.

In another method, Method 4, the present disclosure provides an ex vivo method for treating a patient with HHC as provided in Method 3 wherein the creating step comprises: isolating a somatic cell from the patient; and introducing a set of pluripotency-associated genes into the somatic cell to induce the somatic cell to become a pluripotent stem cell.

In another method, Method 5, the present disclosure provides an ex vivo method for treating a patient with HHC as provided in Method 4, wherein the somatic cell is a fibroblast.

In another method, Method 6, the present disclosure provides an ex vivo method for treating a patient with HHC as provided in Methods 4 or 5, wherein the set of pluripotency-associated genes is one or more of the genes selected from the group consisting of OCT4, SOX2, KLF4, Lin28, NANOG and cMYC.

In another method, Method 7, the present disclosure provides an ex vivo method for treating a patient with HHC as provided in any one of Methods 3-6, wherein the editing step comprises introducing into the iPSC one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene, or within or near a safe harbor locus, that results in restoration of HFE protein activity.

In another method, Method 8, the present disclosure provides an ex vivo method for treating a patient with HHC as provided in Method 7, wherein the safe harbor locus is selected from the group consisting of AAVS1 (PPP1R12C), ALB, Angptl3, ApoC3, ASGR2, CCR5, FIX (F9), G6PC, Gys2, HGD, Lp(a), Pcsk9, Serpina1, TF, and TTR.

In another method, Method 9, the present disclosure provides an ex vivo method for treating a patient with HHC as provided in any one of Methods 3-8, wherein the differentiating step comprises contacting the genome-edited iPSC with one or more of activin, B27 supplement, FGF4, HGF, BMP2, BMP4, Oncostatin M, or Dexametason.

In another method, Method 10, the present disclosure provides an ex vivo method for treating a patient with HHC as provided in any one of Methods 3-9, wherein the implanting step comprises implanting the hepatocyte into the patient by transplantation, local injection, systemic infusion, or combinations thereof.

In another method, Method 11, the present disclosure provides an ex vivo method for treating a patient with HHC, the method comprising: performing a biopsy of the patient's liver; isolating a liver specific progenitor cell or primary hepatocyte from the patient's liver; editing within or near an HFE gene or other DNA sequences that encode regulatory elements of the HFE gene of the liver specific progenitor cell or primary hepatocyte or editing within or near a safe harbor locus of the liver specific progenitor cell or primary hepatocyte; and implanting the genome-edited liver specific progenitor cell or primary hepatocyte into the patient.

In another method, Method 12, the present disclosure provides an ex vivo method for treating a patient with HHC as provided in Method 11, wherein the isolating step comprises: perfusion of fresh liver tissues with digestion enzymes, cell differencial centrifugation, cell culturing, or combinations thereof.

In another method, Method 13, the present disclosure provides an ex vivo method for treating a patient with HHC as provided in Methods 11 or 12, wherein the editing step comprises introducing into the liver specific progenitor cell or primary hepatocyte one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene or within or near a safe harbor locus that results in a permanent deletion, insertion, correction, or modulation of expression or function of one or more mutations within or near or affecting the expression or function of the HFE gene, or within or near a safe harbor locus, and restoration of HFE protein activity.

In another method, Method 14, the present disclosure provides an ex vivo method for treating a patient with HHC as provided in Method 13, wherein the safe harbor locus is selected from the group consisting of AAVS1 (PPP1R12C), ALB, Angptl3, ApoC3, ASGR2, CCR5, FIX (F9), G6PC, Gys2, HGD, Lp(a), Pcsk9, Serpina1, TF, and TTR.

In another method, Method 15, the present disclosure provides an ex vivo method for treating a patient with HHC as provided in any one of Methods 11-14, wherein the implanting step comprises implanting the genome-edited liver specific progenitor cell or primary hepatocyte into the patient by transplantation, local injection, systemic infusion, or combinations thereof.

In another method, Method 16, the present disclosure provides an ex vivo method for treating a patient with HHC, the method comprising: isolating a mesenchymal stem cell from the patient; editing within or near an HFE gene or other DNA sequences that encode regulatory elements of the HFE gene of the mesenchymal stem cell, or editing within or near a safe harbor locus of the mesenchymal stem cell, differentiating the genome-edited mesenchymal stem cell into a hepatocyte; and implanting the hepatocyte into the patient.

In another method, Method 17, the present disclosure provides an ex vivo method for treating a patient with HHC as provided in Method 16, wherein the mesenchymal stem cell is isolated from the patient's bone marrow by performing a biopsy of the patient's bone marrow or the mesenchymal stem cell is isolated from peripheral blood.

In another method, Method 18, the present disclosure provides an ex vivo method for treating a patient with HHC as provided in Methods 16 or 17, wherein the isolating step comprises: aspiration of bone marrow and isolation of mesenchymal cells using density gradient centrifugation media.

In another method, Method 19, the present disclosure provides an ex vivo method for treating a patient with HHC as provided in any one of Methods 16-18, wherein the editing step comprises introducing into the mesenchymal stem cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene or within or near a safe harbor locus, that results in restoration of HFE protein activity.

In another method, Method 20, the present disclosure provides an ex vivo method for treating a patient with HHC as provided in Method 19, wherein the safe harbor locus is selected from the group consisting of AAVS1 (PPP1R12C), ALB, Angptl3, ApoC3, ASGR2, CCR5, FIX (F9), G6PC, Gys2, HGD, Lp(a), Pcsk9, Serpina1, TF, and TTR.

In another method, Method 21, the present disclosure provides an ex vivo method for treating a patient with HHC as provided in any one of Methods 16-20, wherein the differentiating step comprises contacting the genome-edited mesenchymal stem cell with one or more of insulin, transferrin, FGF4, HGF, or bile acids.

In another method, Method 22, the present disclosure provides an ex vivo method for treating a patient with HHC as provided in any one of Methods 16-21, wherein the implanting step comprises implanting the hepatocyte into the patient by transplantation, local injection, systemic infusion, or combinations thereof.

In another method, Method 23, the present disclosure provides an in vivo method for treating a patient with HHC, the method comprising the step of editing an HFE gene in a cell of the patient or other DNA sequences that encode regulatory elements of the HFE gene, or editing within or near a safe harbor locus in a cell of the patient.

In another method, Method 24, the present disclosure provides an in vivo method for treating a patient with HHC as provided in Method 23, wherein the editing step comprises introducing into the cell one or more deoxyribonucleic acid (DNA) endonucleases to effect one or more single-strand breaks (SSBs) or double-strand breaks (DSBs) within or near the HFE gene or other DNA sequences that encode regulatory elements of the HFE gene that results in a permanent deletion, insertion, correction, or modulation of expression or function of one or more mutations within or near or affecting the expression or function of the HFE gene or within or near a safe harbor locus that results in restoration of HFE protein activity.

In another method, Method 25, the present disclosure provides a method according to any one of Methods 1, 2, 7, 13, 19, and 24, wherein the one or more DNA endonucleases is a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

In another method, Method 26, the present disclosure provides a method as provided in Method 25, wherein the method comprises introducing into the cell one or more polynucleotides encoding the one or more DNA endonucleases.

In another method, Method 27, the present disclosure provides a method as provided in Method 25, wherein the method comprises introducing into the cell one or more ribonucleic acids (RNAs) encoding the one or more DNA endonucleases.

In another method, Method 28, the present disclosure provides a method as provided in Methods 26 or 27, wherein the one or more polynucleotides or one or more RNAs is one or more modified polynucleotides or one or more modified RNAs.

In another method, Method 29, the present disclosure provides a method as provided in Method 25, wherein the DNA endonuclease is one or more proteins or polypeptides.

In another method, Method 30, the present disclosure provides a method as provided in any one of Methods 1-29, wherein the method further comprises introducing into the cell one or more guide ribonucleic acids (gRNAs).

In another method, Method 31, the present disclosure provides a method as provided in Method 30, wherein the one or more gRNAs are single-molecule guide RNA (sgRNAs).

In another method, Method 32, the present disclosure provides a method as provided in Methods 30 or 31, wherein the one or more gRNAs or one or more sgRNAs is one or more modified gRNAs or one or more modified sgRNAs.

In another method, Method 33, the present disclosure provides a method as provided in any one of Methods 29-31, wherein the one or more DNA endonucleases is pre-complexed with one or more gRNAs or one or more sgRNAs.

In another method, Method 34, the present disclosure provides a method as provided in any one of Methods 1-33, wherein the method further comprises introducing into the cell a polynucleotide donor template comprising at least a portion of the wild-type HFE gene, DNA sequences that encode wild-type regulatory elements of the HFE gene, or cDNA.

In another method, Method 35, the present disclosure provides a method as provided in Method 34, wherein the at least a portion of the wild-type HFE gene or cDNA is exon 1, exon 2, exon 3, exon 4, exon 5, exon 6, exon 7, intronic regions, fragments or combinations thereof, or the entire HFE gene or cDNA.

In another method, Method 36, the present disclosure provides a method as provided in any one of Methods 34 or 35, wherein the donor template is either single or double stranded.

In another method, Method 37, the present disclosure provides a method as provided in any one of Methods 34-36, wherein the donor template has homologous arms to the 6p21.3 region.

In another method, Method 38, the present disclosure provides a method as provided in any one of Methods 1, 2, 7, 13, 19, and 24, wherein the method further comprises introducing into the cell one guide ribonucleic acid (gRNA) and a polynucleotide donor template comprising at least a portion of the wild-type HFE gene, and wherein the one or more DNA endonucleases is one or more Cas9 or Cpf1 endonucleases that effect one single-strand break (SSB) or double-strand break (DSB) at a locus within or near the HFE gene or other DNA sequences that encode regulatory elements of the HFE gene, or within or near a safe harbor locus, that facilitates insertion of a new sequence from the polynucleotide donor template into the chromosomal DNA at the locus or safe harbor locus that results in a permanent insertion or correction of a part of the chromosomal DNA of the HFE gene or other DNA sequences that encode regulatory elements of the HFE gene proximal to the locus, or safe harbor locus, and wherein the gRNA comprises a spacer sequence that is complementary to a segment of the locus, or safe harbor locus.

In another method, Method 39, the present disclosure provides a method as provided in Method 38, wherein proximal means nucleotides both upstream and downstream of the locus or safe harbor locus.

In another method, Method 40, the present disclosure provides a method as provided in any one of Methods 1, 2, 7, 13, 19, and 24, wherein the method further comprises introducing into the cell one or more guide ribonucleic acid (gRNAs) and a polynucleotide donor template comprising at least a portion of the wild-type HFE gene, and wherein the one or more DNA endonucleases is one or more Cas9 or Cpf1 endonucleases that effect a pair of single-strand breaks (SSBs) or double-strand breaks (DSBs), the first at a 5' locus and the second at a 3' locus, within or near the HFE gene or other DNA sequences that encode regulatory elements of the HFE gene or within or near a safe harbor locus that facilitates insertion of a new sequence from the polynucleotide donor template into the chromosomal DNA between the 5' locus and the 3' locus that results in a permanent insertion or correction of the chromosomal DNA between the 5' locus and the 3' locus within or near the HFE gene or other DNA sequences that encode regulatory elements of the HFE gene or within or near a safe harbor locus, and wherein the first guide RNA comprises a spacer sequence that is complementary to a segment of the 5' locus and the second guide RNA comprises a spacer sequence that is complementary to a segment of the 3' locus.

In another method, Method 41, the present disclosure provides a method as provided in any one of Methods 38-40, wherein the one or more gRNAs are one or more single-molecule guide RNA (sgRNAs).

In another method, Method 42, the present disclosure provides a method as provided in any one of Methods 38-41, wherein the one or more gRNAs or one or more sgRNAs is one or more modified gRNAs or one or more modified sgRNAs.

In another method, Method 43, the present disclosure provides a method as provided in any one of Methods 38-42, wherein the one or more DNA endonucleases is pre-complexed with one or more gRNAs or one or more sgRNAs.

In another method, Method 44, the present disclosure provides a method as provided in any one of Methods 38-43, wherein the at least a portion of the wild-type HFE gene or cDNA is exon 1, exon 2, exon 3, exon 4, exon 5, exon 6, exon 7, intronic regions, fragments or combinations thereof, or the entire HFE gene or cDNA.

In another method, Method 45, the present disclosure provides a method as provided in any one of Methods 38-44, wherein the donor template is either a single or double stranded polynucleotide.

In another method, Method 46, the present disclosure provides a method as provided in any one of Methods 38-45, wherein the donor template has homologous arms to the 6p21.3 region.

In another method, Method 47, the present disclosure provides a method as provided in any one of Method 44, wherein the SSB or DSB are in the first, second, third, fourth, fifth, sixth, seventh exon, or combinations thereof, of the HFE gene.

In another method, Method 48, the present disclosure provides a method as provided in any one of Methods 1, 2, 7, 13, 19, 24, 30-33, or 41-43, wherein the gRNA or sgRNA is directed to one or more of the following pathological variants: C282Y, H63D, S65C, or combinations thereof.

In another method, Method 49, the present disclosure provides a method as provided in any one of Methods 1, 2, 7, 13, 19, and 24-48, wherein the insertion or correction is by HDR.

In another method, Method 50, the present disclosure provides a method as provided in any one of Methods 1, 2, 7, 13, 19, and 24, wherein the method further comprises introducing into the cell two guide ribonucleic acid (gRNAs), and wherein the one or more DNA endonucleases is one or more Cas9 or Cpf1 endonucleases that effect a pair of double-strand breaks (DSBs), the first at a 5' DSB locus and the second at a 3' DSB locus, within or near the HFE gene or other DNA sequences that encode regulatory elements of the HFE gene, or within or near a safe harbor locus that causes a deletion of the chromosomal DNA between the 5'

DSB locus and the 3' DSB locus that results in a permanent deletion of the chromosomal DNA between the 5' DSB locus and the 3' DSB locus within or near the HFE gene or other DNA sequences that encode regulatory elements of the HFE gene or safe harbor locus, and wherein the first guide RNA comprises a spacer sequence that is complementary to a segment of the 5' DSB locus and the second guide RNA comprises a spacer sequence that is complementary to a segment of the 3' DSB locus.

In another method, Method 51, the present disclosure provides a method as provided in Method 50, wherein the two gRNAs are two single-molecule guide RNA (sgRNAs).

In another method, Method 52, the present disclosure provides a method as provided in Methods 50 or 51 wherein the two gRNAs or two sgRNAs are two modified gRNAs or two modified sgRNAs.

In another method, Method 53, the present disclosure provides a method as provided in any one of Methods 50-52, wherein the one or more DNA endonucleases is pre-complexed with one or two gRNAs or one or two sgRNAs.

In another method, Method 54, the present disclosure provides a method as provided in any one of Methods 50-53, wherein both the 5' DSB and 3' DSB are in or near either the first exon, first intron, second exon, second intron, third exon, third intron, fourth exon, fourth intron, fifth exon, fifth intron, sixth exon, sixth intron, seventh exon, seventh intron, or combinations thereof, of the HFE gene.

In another method, Method 55, the present disclosure provides a method as provided in any one of Methods 50-54, wherein the deletion is a deletion of 1 kb or less.

In another method, Method 56, the present disclosure provides a method as provided in any one of Methods 1, 2, 7, 13, 19, and 24-55 wherein the Cas9 or Cpf1 mRNA, gRNA, and donor template are either each formulated into separate lipid nanoparticles or all co-formulated into a lipid nanoparticle.

In another method, Method 57, the present disclosure provides a method as provided in any one of Methods 1, 2, 7, 13, 19, and 24-55, wherein the Cas9 or Cpf1 mRNA is formulated into a lipid nanoparticle, and both the gRNA and donor template are delivered to the cell by an adeno-associated virus (AAV) vector.

In another method, Method 58, the present disclosure provides a method as provided in any one of Methods 1, 2, 7, 13, 19, and 24-55, wherein the Cas9 or Cpf1 mRNA is formulated into a lipid nanoparticle, and the gRNA is delivered to the cell by electroporation and donor template is delivered to the cell by an adeno-associated virus (AAV) vector.

In another method, Method 59, the present disclosure provides a method as provided in any one of Methods 1-58, wherein the HFE gene is located on Chromosome 6: 26087458-26095569 (Genome Reference Consortium—GRCh38/hg38).

In another method, Method 60, the present disclosure provides a method as provided in any one of Methods 1, 2, 7, 13, 19, and 24, wherein the restoration of HFE protein activity is compared to wild-type or normal HFE protein activity.

In a first composition, Composition 1, the present disclosure provides one or more guide ribonucleic acids (gRNAs) for editing an HFE gene in a cell from a patient with HHC, the one or more gRNAs comprising a spacer sequence selected from the group consisting of nucleic acid sequences in SEQ ID NOs: 1-64,980 of the Sequence Listing.

In another composition, Composition 2, the present disclosure provides the one or more gRNAs of Composition 1, wherein the one or more gRNAs are one or more single-molecule guide RNAs (sgRNAs).

In another composition, Composition 3, the present disclosure provides the one or more gRNAs or sgRNAs of Compositions 1 or 2, wherein the one or more gRNAs or one or more sgRNAs is one or more modified gRNAs or one or more modified sgRNAs.

In another composition, Composition 4, the present disclosure provides the one or more gRNAs or sgRNAs of Compositions 1-3, wherein the cell is selected from a group consisting of a liver cell, skin cell, pancreatic cell, heart cell, joint cell, or cell from the testes.

In another method, Method 65, the present disclosure provides a method as provided in any one of Method 1, wherein the human cell is selected from a group consisting of a liver cell, skin cell, pancreatic cell, heart cell, joint cell, or cell from the testes.

In another method, Method 66, the present disclosure provides a method as provided in any one of Method 23, wherein the human cell is selected from a group consisting of a liver cell, skin cell, pancreatic cell, heart cell, joint cell, or cell from the testes.

Definitions

The term "comprising" or "comprises" is used in reference to compositions, methods, and respective component(s) thereof, that are essential to the invention, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

EXAMPLES

The invention will be more fully understood by reference to the following examples, which provide illustrative non-limiting aspects of the invention.

The examples describe the use of the CRISPR system as an illustrative genome editing technique to create defined therapeutic genomic deletions, insertions, or replacements, termed "genomic modifications" herein, in the HFE gene that lead to permanent correction of mutations in the genomic locus, or expression at a heterologous locus, that restore HFE protein activity.

Single gRNAs spanning different regions of the HFE gene were selected and tested for cutting efficiencies (Table 5).

TABLE 5

| SEQ ID NO. | gRNA Name | gRNA Sequence without PAM | PAM Sequence |
|---|---|---|---|
| 409 | Hfe_T5 | CGCTTGCTGCGTGAGTCCGA | GGG |
| 4117 | Hfe_T338 | AGATGCCCAGTAAAACTTCC | TGG |
| 377 | Hfe_T252 | TGAGCCTAGGCAATAGCTGT | AGG |
| 378 | Hfe_T101 | GAGCCTAGGCAATAGCTGTA | GGG |
| 4114 | Hfe_T394 | TACAGCTATTGCCTAGGCTC | AGG |
| 4112 | Hfe_T240 | TCACCCTACAGCTATTGCCT | AGG |
| 379 | Hfe_T158 | AATAGCTGTAGGGTGACTTC | TGG |
| 4106 | Hfe_T377 | TTTTGGGGGCGGGGAAACG | GGG |
| 4102 | Hfe_T278 | CTCCGCTTCTTTTGGGGGGC | GGG |
| 4100 | Hfe_T402 | AAATCTCCGCTTCTTTTGGG | GGG |
| 4099 | Hfe_T285 | TAAATCTCCGCTTCTTTTGG | GGG |
| 4098 | Hfe_T398 | TTAAATCTCCGCTTCTTTTG | GGG |
| 386 | Hfe_T238 | AAAAGAAGCGGAGATTTAAC | GGG |
| 4097 | Hfe_T304 | GTTAAATCTCCGCTTCTTTT | GGG |
| 387 | Hfe_T88 | AAAGAAGCGGAGATTTAACG | GGG |
| 4096 | Hfe_T108 | CGTTAAATCTCCGCTTCTTT | TGG |
| 388 | Hfe_T18 | GGAGATTTAACGGGGACGTG | CGG |
| 391 | Hfe_T60 | GGGAAATGGGCCCGCGAGCC | AGG |
| 399 | Hfe_T117 | AATGGGCCCGCGAGCCAGGC | CGG |
| 4093 | Hfe_T99 | GAAGCGCCGGCCTGGCTCGC | GGG |
| 4092 | Hfe_T100 | AGAAGCGCCGGCCTGGCTCG | CGG |
| 4091 | Hfe_T239 | CAGGAGGAGAAGCGCCGGCC | TGG |
| 401 | Hfe_T118 | CCTGATGCTTTGCAGACCG | CGG |
| 4087 | Hfe_T246 | CGGTCTGCAAAAGCATCAGG | AGG |
| 4085 | Hfe_T24 | CCGCGGTCTGCAAAAGCATC | AGG |
| 403 | Hfe_T27 | TTTGCAGACCGCGGTCCTGC | AGG |

TABLE 5-continued

| SEQ ID NO. | gRNA Name | gRNA Sequence without PAM | PAM Sequence |
|---|---|---|---|
| 404 | Hfe_T34 | TTGCAGACCGCGGTCCTGCA | GGG |
| 405 | Hfe_T146 | TGCAGACCGCGGTCCTGCAG | GGG |
| 4082 | Hfe_T152 | CAAGCGCCCCTGCAGGACCG | CGG |
| 4081 | Hfe_T78 | CACGCAGCAAGCGCCCCTGC | AGG |
| 408 | Hfe_T11 | GCGCTTGCTGCGTGAGTCCG | AGG |
| 410 | Hfe_T269 | CTGCGTGAGTCCGAGGGCTG | CGG |
| 411 | Hfe_T157 | TGCGTGAGTCCGAGGGCTGC | GGG |
| 413 | Hfe_T19 | CCGAGGGCTGCGGGCGAACT | AGG |
| 414 | Hfe_T1 | CGAGGGCTGCGGGCGAACTA | GGG |
| 415 | Hfe_T3 | GAGGGCTGCGGGCGAACTAG | GGG |
| 4077 | Hfe_T61 | CCTAGTTCGCCCGCAGCCCT | CGG |
| 416 | Hfe_T28 | CTGCGGGCGAACTAGGGGCG | CGG |
| 417 | Hfe_T68 | CGGGCGAACTAGGGGCGCGG | CGG |
| 418 | Hfe_T122 | GGGCGAACTAGGGGCGCGGC | CGG |
| 419 | Hfe_T113 | GGCGAACTAGGGGCGCGGCG | GGG |
| 420 | Hfe_T138 | GCGAACTAGGGGCGCGGCGG | GGG |
| 423 | Hfe_T274 | ACTAGCTTTTCTTTGCGCT | TGG |
| 426 | Hfe_T208 | GCTTGGGAGTTTGCTAACTT | TGG |
| 428 | Hfe_T264 | TGGGAGTTTGCTAACTTTGG | AGG |
| 3678 | Hfe_T131 | CTCATACCATCAGCTGTGTC | TGG |
| 964 | Hfe_T132 | CTGATGGTATGAGTTGATGC | AGG |
| 969 | Hfe_T207 | CCTCCTACTACACATGGTTA | AGG |
| 3671 | Hfe_T352 | TTAACCATGTGTAGTAGGAG | GGG |
| 3670 | Hfe_T233 | CTTAACCATGTGTAGTAGGA | GGG |
| 3669 | Hfe_T171 | CCTTAACCATGTGTAGTAGG | AGG |
| 3667 | Hfe_T59 | AGGCCTTAACCATGTGTAGT | AGG |
| 3659 | Hfe_T385 | TAGTGCAGAGAGTGTGAACC | TGG |
| 972 | Hfe_T547 | CTCTCTGCACTACCTCTTCA | TGG |
| 973 | Hfe_T303 | TCTCTGCACTACCTCTTCAT | GGG |
| 3654 | Hfe_T448 | GCTCTGAGGCACCCATGAAG | AGG |
| 977 | Hfe_T458 | CTTCATGGGTGCCTCAGAGC | AGG |
| 978 | Hfe_T642 | GGTGCCTCAGAGCAGGACCT | TGG |
| 3651 | Hfe_T667 | AAGACCAAGGTCCTGCTCTG | AGG |
| 980 | Hfe_T732 | TCTTTCCTTGTTTGAAGCTT | TGG |
| 981 | Hfe_T740 | CTTTCCTTGTTTGAAGCTTT | GGG |
| 3646 | Hfe_T281 | GTAGCCCAAAGCTTCAAACA | AGG |
| 982 | Hfe_T44 | GTTTGAAGCTTTGGGCTACG | TGG |
| 3642 | Hfe_T102 | GATCATAGAACACGAACAGC | TGG |
| 986 | Hfe_T4 | TGATCATGAGAGTCGCCGTG | TGG |

TABLE 5-continued

| SEQ ID NO. | gRNA Name | gRNA Sequence without PAM | PAM Sequence |
|---|---|---|---|
| 988 | Hfe_T106 | GTGTGGAGCCCCGAACTCCA | TGG |
| 989 | Hfe_T33 | TGTGGAGCCCCGAACTCCAT | GGG |
| 3639 | Hfe_T151 | ATGGAGTTCGGGGCTCCACA | CGG |
| 3638 | Hfe_T91 | CTGGAAACCCATGGAGTTCG | GGG |
| 3637 | Hfe_T388 | ACTGGAAACCCATGGAGTTC | GGG |
| 3636 | Hfe_T234 | TACTGGAAACCCATGGAGTT | CGG |
| 3634 | Hfe_T552 | GAAATTCTACTGGAAACCCA | TGG |
| 3633 | Hfe_T372 | CATCTGGCTTGAAATTCTAC | TGG |
| 3632 | Hfe_T494 | GACTCAGCTGCAGCCACATC | TGG |
| 1000 | Hfe_T694 | CAGCTGAGTCAGAGTCTGAA | AGG |
| 1002 | Hfe_T762 | TGAGTCAGAGTCTGAAAGGG | TGG |
| 1003 | Hfe_T579 | GAGTCAGAGTCTGAAAGGGT | GGG |
| 1004 | Hfe_T558 | ACATGTTCACTGTTGACTTC | TGG |
| 1005 | Hfe_T397 | TGTTGACTTCTGGACTATTA | TGG |
| 1010 | Hfe_T608 | ACAACCACAGCAAGGGTATG | TGG |
| 1013 | Hfe_T566 | CACAGCAAGGGTATGTGGAG | AGG |
| 1014 | Hfe_T721 | ACAGCAAGGGTATGTGGAGA | GGG |
| 3624 | Hfe_T374 | CTCTCCACATACCCTTGCTG | TGG |
| 1015 | Hfe_T687 | CAGCAAGGGTATGTGGAGAG | GGG |
| 3621 | Hfe_T411 | AAGCTCTGACAACCTCAGGA | AGG |
| 3619 | Hfe_T530 | TGAAAAGCTCTGACAACCTC | AGG |
| 1028 | Hfe_T429 | GCTGGAAGTCTGAGGTCTTG | TGG |
| 1029 | Hfe_T386 | CTGGAAGTCTGAGGTCTTGT | GGG |
| 1032 | Hfe_T441 | GTCTGAGGTCTTGTGGGAGC | AGG |
| 1033 | Hfe_T636 | TCTGAGGTCTTGTGGGAGCA | GGG |
| 1041 | Hfe_T658 | ATTTGCTTCCTGAGATCATT | TGG |
| 1042 | Hfe_T359 | TCCTGAGATCATTTGGTCCT | TGG |
| 1043 | Hfe_T290 | CCTGAGATCATTTGGTCCTT | GGG |
| 1044 | Hfe_T346 | CTGAGATCATTTGGTCCTTG | GGG |
| 3610 | Hfe_T168 | CCCAAGGACCAAATGATCTC | AGG |
| 1045 | Hfe_T446 | GATCATTTGGTCCTTGGGGA | TGG |
| 1049 | Hfe_T553 | CCTTGGGGATGGTGGAAATA | GGG |
| 1050 | Hfe_T216 | GAAATAGGGACCTATTCCTT | TGG |
| 1053 | Hfe_T376 | TCCTTTGGTTGCAGTTAACA | AGG |
| 1054 | Hfe_T188 | TTGGTTGCAGTTAACAAGGC | TGG |
| 3604 | Hfe_T232 | GCCTTGTTAACTGCAACCAA | AGG |
| 1055 | Hfe_T230 | TGGTTGCAGTTAACAAGGCT | GGG |
| 1056 | Hfe_T329 | GGTTGCAGTTAACAAGGCTG | GGG |
| 3601 | Hfe_T537 | ACCTGCAGGGTGTGGGACTC | TGG |
| 1062 | Hfe_T396 | CACACCCTGCAGGTCATCCT | GGG |
| 3598 | Hfe_T450 | ACAGCCCAGGATGACCTGCA | GGG |
| 1067 | Hfe_T48 | GCAAGAAGACAACAGTACCG | AGG |
| 1068 | Hfe_T175 | CAAGAAGACAACAGTACCGA | GGG |
| 1069 | Hfe_T84 | ACAACAGTACCGAGGGCTAC | TGG |
| 1071 | Hfe_T89 | ACCGAGGGCTACTGGAAGTA | CGG |
| 1072 | Hfe_T50 | CCGAGGGCTACTGGAAGTAC | GGG |
| 3592 | Hfe_T144 | CCCGTACTTCCAGTAGCCCT | CGG |
| 1073 | Hfe_T57 | TACTGGAAGTACGGGTATGA | TGG |
| 1074 | Hfe_T23 | ACTGGAAGTACGGGTATGAT | GGG |
| 1076 | Hfe_T66 | GAAGTACGGGTATGATGGGC | AGG |
| 3588 | Hfe_T504 | GTGTGTCAGGGCAGAATTCA | AGG |
| 1077 | Hfe_T521 | TGAATTCTGCCCTGACACAC | TGG |
| 1078 | Hfe_T206 | TCTGCCCTGACACACTGGAT | TGG |
| 3585 | Hfe_T404 | CTCTCCAATCCAGTGTGTCA | GGG |
| 3584 | Hfe_T211 | GCTCTCCAATCCAGTGTGTC | AGG |
| 1084 | Hfe_T531 | ATTGGAGAGCAGCAGAACCC | AGG |
| 1088 | Hfe_T542 | CAGGGCCTGGCCCACCAAGC | TGG |
| 1090 | Hfe_T472 | CCTGGCCCACCAAGCTGGAG | TGG |
| 1091 | Hfe_T375 | CTGGCCCACCAAGCTGGAGT | GGG |
| 3577 | Hfe_T508 | CTTTCCCACTCCAGCTTGGT | GGG |
| 1096 | Hfe_T528 | GTGGGAAAGGCACAAGATTC | GGG |
| 1098 | Hfe_T179 | AAAGGCACAAGATTCGGGCC | AGG |
| 1101 | Hfe_T277 | AGATTCGGGCCAGGCAGAAC | AGG |
| 1102 | Hfe_T318 | GATTCGGGCCAGGCAGAACA | GGG |
| 1103 | Hfe_T313 | CAGGCAGAACAGGGCCTACC | TGG |
| 3573 | Hfe_T405 | CAGGTAGGCCCTGTTCTGCC | TGG |
| 3572 | Hfe_T493 | AGGGCAGTCCCTCTCCAGGT | AGG |
| 1121 | Hfe_T342 | AGAGGTGTTTTGGACCAACA | AGG |
| 1122 | Hfe_T104 | TGTTTTGGACCAACAAGGTA | TGG |
| 1123 | Hfe_T299 | TTTGGACCAACAAGGTATGG | TGG |
| 3561 | Hfe_T82 | GTGTTTCCACCATACCTTGT | TGG |
| 1125 | Hfe_T98 | CTTCTGCCCCTATACTCTAG | TGG |
| 1128 | Hfe_T355 | CCTATACTCTAGTGGCAGAG | TGG |
| 3558 | Hfe_T120 | ACTCTGCCACTAGAGTATAG | GGG |
| 3557 | Hfe_T111 | CACTCTGCCACTAGAGTATA | GGG |
| 3556 | Hfe_T205 | CCACTCTGCCACTAGAGTAT | AGG |
| 1137 | Hfe_T210 | GTTGCAGGGCACGGAATCCC | TGG |

TABLE 5-continued

| SEQ ID NO. | gRNA Name | gRNA Sequence without PAM | PAM Sequence |
|---|---|---|---|
| 1138 | Hfe_T112 | CAGGGCACGGAATCCCTGGT | TGG |
| 1142 | Hfe_T418 | ATCCCTGGTTGGAGTTTCAG | AGG |
| 3552 | Hfe_T327 | CACCTCTGAAACTCCAACCA | GGG |
| 1158 | Hfe_T294 | ATGAGACAGCCACAAGTCAT | GGG |
| 1161 | Hfe_T204 | TCTCCATGCATATGGCTCAA | AGG |
| 1162 | Hfe_T231 | CTCCATGCATATGGCTCAAA | GGG |
| 3531 | Hfe_T322 | TTCCCTTTGAGCCATATGCA | TGG |
| 1164 | Hfe_T361 | GGCTCAAAGGGAAGTGTCTA | TGG |
| 1223 | Hfe_T129 | TCAGCTATCATATGAATACC | AGG |
| 3479 | Hfe_T250 | CCTCACTTGATATTTTGTCC | TGG |
| 3478 | Hfe_T369 | GATTCTTCTACTCTGATAAG | TGG |
| 1232 | Hfe_T8 | TCAGAGTAGAAGAATCCTTT | AGG |
| 3471 | Hfe_T217 | AAGAAGCGGACTTGTAAGAT | AGG |
| 1241 | Hfe_T62 | AATGCCTCCTAGGTTGACCC | AGG |
| 3465 | Hfe_T147 | TTCACCTGGGTCAACCTAGG | AGG |
| 3463 | Hfe_T289 | AGTTTCACCTGGGTCAACCT | AGG |
| 3461 | Hfe_T421 | ACAGATGGTCAGTTTCACCT | GGG |
| 3460 | Hfe_T209 | TACAGATGGTCAGTTTCACC | TGG |
| 3450 | Hfe_T311 | GACTCTAACACAGTGTCACT | TGG |
| 1258 | Hfe_T92 | CTGTGTTAGAGTCCAATCTT | AGG |
| 3448 | Hfe_T224 | ACCATTTTGTGTCCTAAGAT | TGG |
| 1266 | Hfe_T193 | TCCTTCCTCCAACCTATAGA | AGG |
| 3438 | Hfe_T235 | CACTTCCTTCTATAGGTTGG | AGG |
| 3433 | Hfe_T243 | TTTACCCTTGCCAGGAAGAC | TGG |
| 3431 | Hfe_T83 | GGGATCTGTTTACCCTTGCC | AGG |
| 3417 | Hfe_T93 | CACCAAAGGAGGCACTTGAC | AGG |
| 1278 | Hfe_T371 | TCAAGTGCCTCCTTTGGTGA | AGG |
| 3395 | Hfe_T198 | TCGAACTCCTTGGCATCCAT | TGG |
| 3394 | Hfe_T186 | GTCTTTAGGTTCGAACTCCT | TGG |
| 1295 | Hfe_T41 | CCTAAAGACGTATTGCCCAA | TGG |
| 1296 | Hfe_T36 | CTAAAGACGTATTGCCCAAT | GGG |
| 1297 | Hfe_T133 | TAAAGACGTATTGCCCAATG | GGG |
| 3393 | Hfe_T39 | CCATTGGGCAATACGTCTTT | AGG |
| 1298 | Hfe_T87 | GACGTATTGCCCAATGGGGA | TGG |
| 1299 | Hfe_T45 | ACGTATTGCCCAATGGGGAT | GGG |
| 1301 | Hfe_T801 | CAATGGGATGGGACCTACC | AGG |
| 1302 | Hfe_T125 | AATGGGATGGGACCTACCA | GGG |
| 3391 | Hfe_T366 | TGGTAGGTCCCATCCCCATT | GGG |

TABLE 5-continued

| SEQ ID NO. | gRNA Name | gRNA Sequence without PAM | PAM Sequence |
|---|---|---|---|
| 3390 | Hfe_T167 | CTGGTAGGTCCCATCCCCAT | TGG |
| 1303 | Hfe_T324 | GGGATGGGACCTACCAGGGC | TGG |
| 1304 | Hfe_T134 | CTACCAGGGCTGGATAACCT | TGG |
| 3389 | Hfe_T174 | CAAGGTTATCCAGCCCTGGT | AGG |
| 3387 | Hfe_T140 | CAGCCAAGGTTATCCAGCCC | TGG |
| 1305 | Hfe_T85 | ATAACCTTGGCTGTACCCCC | TGG |
| 1306 | Hfe_T155 | TAACCTTGGCTGTACCCCCT | GGG |
| 1307 | Hfe_T242 | AACCTTGGCTGTACCCCCTG | GGG |
| 3385 | Hfe_T331 | TTCCCCAGGGGTACAGCCA | AGG |
| 3382 | Hfe_T829 | TATCTCTGCTCTTCCCCAGG | GGG |
| 3381 | Hfe_T731 | ATATCTCTGCTCTTCCCCAG | GGG |

All tested gRNAs can be used for an HDR/correction based editing approach. Single gRNAs targeting the splice acceptors can be used to induce exon skipping to restore the reading frame of the HFE gene. Selected pairs of gRNAs can be used to make deletions in the HFE gene that restore the reading frame. Selected pairs of gRNAs can be used to make deletions that simulate patient mutations and can be used to generate model HFE mutant lines.

Various Cas orthologs were evaluated for cutting. SP, NM, ST, SA, and TO gRNAs were delivered as RNA, expressed from the U6 promoter in plasmids, or expressed from the U6 promoter in lentivirus. The corresponding Gas protein was either knocked into the cell line of interest and constitutively expressed, delivered as mRNA, or delivered as protein. The activity of the gRNAs in all the above mentioned formats were evaluated using TIDE analysis or next generation sequencing in HEK293T cells, K562 cells, or induced pluripotent stem cells (iPSCs).

Overall, it was determined that most gRNAs tested induced cutting. However, the amount of cutting was highly dependent on the Gas protein tested. It was found that, generally, SP Cas9 gRNAs induce the highest levels of cutting. Generally, it is beneficial to select gRNAs for therapeutic application that have the highest cutting efficiency possible. However, for an iPSC based therapy, the cutting efficiency is not as important. iPSCs are highly proliferative and make it simple to isolate a clonal population of cells with the desired edit, even when the editing efficiency is less than 10%.

Introduction of the defined therapeutic modifications described above represents a novel therapeutic strategy for the potential amelioration of HHC, as described and illustrated herein.

Example 1—CRISPR/SpCas9 Target Sites for the HFE Gene

Regions of the HFE gene were scanned for target sites. Each area was scanned for a protospacer adjacent motif (PAM) having the sequence NRG. gRNA 20 bp spacer sequences corresponding to the PAM were identified, as shown in SEQ ID NOs: 1-4,455 of the Sequence Listing.

Example 2—CRISPR/SaCas9 Target Sites for the HFE Gene

Regions of the HFE gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 4,456-4,979 of the Sequence Listing.

Example 3—CRISPR/StCas9 Target Sites for the HFE Gene

Regions of the HFE gene were scanned for target sites. Each area was scanned for a protospacer adjacent motif (PAM) having the sequence NNAGAAW. gRNA 24 bp spacer sequences corresponding to the PAM were identified, as shown in SEQ ID NOs: 4,980-5,139 of the Sequence Listing.

Example 4—CRISPR/TdCas9 Target Sites for the HFE Gene

Regions of the HFE gene were scanned for target sites. Each area was scanned for a protospacer adjacent motif (PAM) having the sequence NAAAAC. gRNA 24 bp spacer sequences corresponding to the PAM were identified, as shown in SEQ ID NOs: 5,140-5,192 of the Sequence Listing.

Example 5—CRISPR/NmCas9 Target Sites for the HFE Gene

Regions of the HFE gene were scanned for target sites. Each area was scanned for a protospacer adjacent motif (PAM) having the sequence NNNNGHTT. gRNA 24 bp spacer sequences corresponding to the PAM were identified, as shown in SEQ ID NOs: 5,193-5,617 of the Sequence Listing.

Example 6—CRISPR/Cpf1 Target Sites for the HFE Gene

Regions of the HFE gene were scanned for target sites. Each area was scanned for a protospacer adjacent motif (PAM) having the sequence YTN. gRNA 20-24 bp spacer sequences corresponding to the PAM were identified, as shown in SEQ ID NOs: 5,618-10,121 of the Sequence Listing.

Example 7—CRISPR/SpCas9 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence NRG. gRNA 20 bp spacer sequences corresponding to the PAM were identified, as shown in SEQ ID NOs: 10,122-12,153 of the Sequence Listing.

Example 8—CRISPR/SaCas9 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 12,154-12,324 of the Sequence Listing.

Example 9—CRISPR/StCas9 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 12,325-12,342 of the Sequence Listing.

Example 10—CRISPR/TdCas9 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 12,343-12,351 of the Sequence Listing.

Example 11—CRISPR/NmCas9 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 12,352-12,426 of the Sequence Listing.

Example 12—CRISPR/Cpf1 Target Sites for the AAVS1 (PPP1R12C) Gene

Exons 1-2 of the AAVS1 (PPP1R12C) gene were scanned for target sites. Each area was scanned for a protospacer adjacent motif (PAM) having the sequence YTN. gRNA 22 bp spacer sequences corresponding to the PAM were identified, as shown in SEQ ID NOs: 12,427-13,602 of the Sequence Listing.

Example 13—CRISPR/SpCas9 Target Sites for the ALB Gene

Exons 1-2 of the ALB gene were scanned for target sites. Each area was scanned for a protospacer adjacent motif (PAM) having the sequence NRG. gRNA 20 bp spacer sequences corresponding to the PAM were identified, as shown in SEQ ID NOs: 13,603-13,770 of the Sequence Listing.

Example 14—CRISPR/SaCas9 Target Sites for the ALB Gene

Exons 1-2 of the ALB gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 13,771-13,798 of the Sequence Listing.

Example 15—CRISPR/StCas9 Target Sites for the ALB Gene

Exons 1-2 of the ALB gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 13,799-13,816 of the Sequence Listing.

Example 16—CRISPR/TdCas9 Target Sites for the ALB Gene

Exons 1-2 of the ALB gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 13,817-13,821 of the Sequence Listing.

Example 17—CRISPR/NmCas9 Target Sites for the ALB Gene

Exons 1-2 of the ALB gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 13,822-13,845 of the Sequence Listing.

Example 18—CRISPR/Cpf1 Target Sites for the ALB Gene

Exons 1-2 of the ALB gene were scanned for target sites. Each area was scanned for a protospacer adjacent motif (PAM) having the sequence YTN. gRNA 22 bp spacer sequences corresponding to the PAM were identified, as shown in SEQ ID NOs: 13,846-14,224 of the Sequence Listing.

Example 19—CRISPR/SaCas9 Target Sites for the Angptl3 Gene

Exons 1-2 of the Angpt13 gene were scanned for target sites. Each area was scanned for a protospacer adjacent motif (PAM) having the sequence NRG. gRNA 20 bp spacer sequences corresponding to the PAM were identified, as shown in SEQ ID NOs: 14,225-14,569 of the Sequence Listing.

Example 20—CRISPR/SaCas9 Target Sites for the Angptl3 Gene

Exons 1-2 of the Angpt13 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 14,570-14,605 of the Sequence Listing.

Example 21—CRISPR/StCas9 Target Sites for the Anaptl3 Gene

Exons 1-2 of the Angpt13 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 14,606-14,628 of the Sequence Listing.

Example 22—CRISPR/TdCas9 Target Sites for the Anaptl3 Gene

Exons 1-2 of the Angpt13 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 14,629-14,641 of the Sequence Listing.

Example 23—CRISPR/NmCas9 Target Sites for the Anaptl3 Gene

Exons 1-2 of the Angpt13 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 14,642-14,704 of the Sequence Listing.

Example 24—CRISPR/Cpf1 Target Sites for the Angptl3 Gene

Exons 1-2 of the Angpt13 gene were scanned for target sites. Each area was scanned for a protospacer adjacent motif (PAM) having the sequence YTN. gRNA 22 bp spacer sequences corresponding to the PAM were identified, as shown in SEQ ID NOs: 14,705-15,552 of the Sequence Listing.

Example 25—CRISPR/SpCas9 Target Sites for the ApoC3 Gene

Exons 1-2 of the ApoC3 gene were scanned for target sites. Each area was scanned for a protospacer adjacent motif (PAM) having the sequence NRG. gRNA 20 bp spacer sequences corresponding to the PAM were identified, as shown in SEQ ID NOs: 15,553-15,955 of the Sequence Listing.

Example 26—CRISPR/SaCas9 Target Sites for the ApoC3 Gene

Exons 1-2 of the ApoC3 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 15,956-15,980 of the Sequence Listing.

Example 27—CRISPR/StCas9 Target Sites for the ApoC3 Gene

Exons 1-2 of the ApoC3 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 15,981-15,983 of the Sequence Listing.

Example 28—CRISPR/TdCas9 Target Sites for the ApoC3 Gene

Exons 1-2 of the ApoC3 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 15,984-15,985 of the Sequence Listing.

Example 29—CRISPR/NmCas9 Target Sites for the ApoC3 Gene

Exons 1-2 of the ApoC3 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 15,986-15,997 of the Sequence Listing.

Example 30—CRISPR/Cpf1 Target Sites for the ApoC3 Gene

Exons 1-2 of the ApoC3 gene were scanned for target sites. Each area was scanned for a protospacer adjacent motif (PAM) having the sequence YTN. gRNA 22 bp spacer sequences corresponding to the PAM were identified, as shown in SEQ ID NOs: 15,998-16,229 of the Sequence Listing.

Example 31—CRISPR/SaCas9 Target Sites for the ASGR2 Gene

Exons 1-2 of the ASGR2 gene were scanned for target sites. Each area was scanned for a protospacer adjacent motif (PAM) having the sequence NRG. gRNA 20 bp spacer sequences corresponding to the PAM were identified, as shown in SEQ ID NOs: 16,230-17,997 of the Sequence Listing.

Example 32—CRISPR/SaCas9 Target Sites for the ASGR2 Gene

Exons 1-2 of the ASGR2 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 17,998-18,203 of the Sequence Listing.

Example 33—CRISPR/StCas9 Target Sites for the ASGR2 Gene

Exons 1-2 of the ASGR2 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 18,204-18,227 of the Sequence Listing.

Example 34—CRISPR/TdCas9 Target Sites for the ASGR2 Gene

Exons 1-2 of the ASGR2 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 18,228-18,239 of the Sequence Listing.

Example 35—CRISPR/NmCas9 Target Sites for the ASGR2 Gene

Exons 1-2 of the ASGR2 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 18,240-18,322 of the Sequence Listing.

Example 36—CRISPR/Cpf1 Target Sites for the ASGR2 Gene

Exons 1-2 of the ASGR2 gene were scanned for target sites. Each area was scanned for a protospacer adjacent motif (PAM) having the sequence YTN. gRNA 22 bp spacer sequences corresponding to the PAM were identified, as shown in SEQ ID NOs: 18,323-19,762 of the Sequence Listing.

Example 37—CRISPR/SpCas9 Target Sites for the CCR5 Gene

Exons 1-2 of the CCR5 gene were scanned for target sites. Each area was scanned for a protospacer adjacent motif (PAM) having the sequence NRG. gRNA 20 bp spacer sequences corresponding to the PAM were identified, as shown in SEQ ID NOs: 19,763-19,965 of the Sequence Listing.

Example 38—CRISPR/SaCas9 Target Sites for the CCR5 Gene

Exons 1-2 of the CCR5 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 19,966-19,997 of the Sequence Listing.

Example 39—CRISPR/StCas9 Target Sites for the CCR5 Gene

Exons 1-2 of the CCR5 gene were scanned for target sites Each area was scanned for a protospacer adjacent motif (PAM) having the sequence NNAGAAW. gRNA 20 bp spacer sequences corresponding to the PAM were identified, as shown in SEQ ID NOs: 19,998-20,011 of the Sequence Listing.

Example 40—CRISPR/TdCas9 Target Sites for the CCR5 Gene

Exons 1-2 of the CCR5 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 20,012-20,013 of the Sequence Listing.

Example 41—CRISPR/NmCas9 Target Sites for the CCR5 Gene

Exons 1-2 of the CCR5 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 20,014-20,041 of the Sequence Listing.

Example 42—CRISPR/Cpf1 Target Sites for the CCR5 Gene

Exons 1-2 of the CCR5 gene were scanned for target sites. Each area was scanned for a protospacer adjacent motif (PAM) having the sequence YTN. gRNA 22 bp spacer sequences corresponding to the PAM were identified, as shown in SEQ ID NOs: 20,042-20,341 of the Sequence Listing.

Example 43—CRISPR/SaCas9 Target Sites for the FIX (F91 Gene

Exons 1-2 of the FIX (F9) gene were scanned for target sites. Each area was scanned for a protospacer adjacent motif (PAM) having the sequence NRG. gRNA 20 bp spacer sequences corresponding to the PAM were identified, as shown in SEQ ID NOs: 20,342-21,807 of the Sequence Listing.

Example 44—CRISPR/SaCas9 Target Sites for the FIX (F9) Gene

Exons 1-2 of the FIX (F9) gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 21,808-21,970 of the Sequence Listing.

Example 45—CRISPR/StCas9 Target Sites for the FIX (F9) Gene

Exons 1-2 of the FIX (F9) gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 21,971-22,031 of the Sequence Listing.

Example 46—CRISPR/TdCas9 Target Sites for the FIX (F9) Gene

Exons 1-2 of the FIX (F9) gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 22,032-22,056 of the Sequence Listing.

Example 47—CRISPR/NmCas9 Target Sites for the FIX (F91 Gene

Exons 1-2 of the FIX (F9) gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 22,057-22,209 of the Sequence Listing.

Example 48—CRISPR/Cpf1 Target Sites for the FIX (F9) Gene

Exons 1-2 of the FIX (F9) gene were scanned for target sites. Each area was scanned for a protospacer adjacent motif (PAM) having the sequence YTN. gRNA 22 bp spacer sequences corresponding to the PAM were identified, as shown in SEQ ID NOs: 22,210-24,350 of the Sequence Listing.

Example 49—CRISPR/SpCas9 Target Sites for the G6PC Gene

Regions of the G6PC gene were scanned for target sites. Each area was scanned for a protospacer adjacent motif (PAM) having the sequence NRG. gRNA 20 bp spacer sequences corresponding to the PAM were identified, as shown in SEQ ID NOs: 24,351-25,366 of the Sequence Listing.

Example 50—CRISPR/SaCas9 Target Sites for the G6PC Gene

Regions of the G6PC gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 25,367-25,483 of the Sequence Listing.

Example 51—CRISPR/StCas9 Target Sites for the G6PC Gene

Regions of the G6PC gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 25,484-25,507 of the Sequence Listing.

Example 52—CRISPR/TdCas9 Target Sites for the G6PC Gene

Regions of the G6PC gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 25,508-25,516 of the Sequence Listing.

Example 53—CRISPR/NmCas9 Target Sites for the G6PC Gene

Regions of the G6PC gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 25,517-25,606 of the Sequence Listing.

Example 54—CRISPR/Cpf1 Target Sites for the G6PC Gene

Regions of the G6PC gene were scanned for target sites. Each area was scanned for a protospacer adjacent motif (PAM) having the sequence YTN. gRNA 22 bp spacer sequences corresponding to the PAM were identified, as shown in SEQ ID NOs: 25,607-26,701 of the Sequence Listing.

Example 55—CRISPR/SpCas9 Target Sites for the Gys2 Gene

Exons 1-2 of the Gys2 gene were scanned for target sites. Each area was scanned for a protospacer adjacent motif (PAM) having the sequence NRG. gRNA 20 bp spacer sequences corresponding to the PAM were identified, as shown in SEQ ID NOs: 26,702-32,194 of the Sequence Listing.

Example 56—CRISPR/SaCas9 Target Sites for the Gys2 Gene

Exons 1-2 of the Gys2 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 32,195-32,870 of the Sequence Listing.

Example 57—CRISPR/StCas9 Target Sites for the Gys2 Gene

Exons 1-2 of the Gys2 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 32,871-33,148 of the Sequence Listing.

Example 58—CRISPR/TdCas9 Target Sites for the Gys2 Gene

Exons 1-2 of the Gys2 gene were scanned for target sites. Each area was scanned for a protospacer adjacent motif (PAM) having the sequence NAAAAC gRNA 20 bp spacer sequences corresponding to the PAM were identified, as shown in SEQ ID NOs: 33,149-33,262 of the Sequence Listing.

Example 59—CRISPR/NmCas9 Target Sites for the Gys2 Gene

Exons 1-2 of the Gys2 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 33,263-33,942 of the Sequence Listing.

Example 60—CRISPR/Cpf1 Target Sites for the Gys2 Gene

Exons 1-2 of the Gys2 gene were scanned for target sites. Each area was scanned for a protospacer adjacent motif (PAM) having the sequence YTN. gRNA 22 bp spacer sequences corresponding to the PAM were identified, as shown in SEQ ID NOs: 33,943-42,374 of the Sequence Listing.

Example 61—CRISPR/SpCas9 Target Sites for the HGD Gene

Exons 1-2 of the HGD gene were scanned for target sites. Each area was scanned for a protospacer adjacent motif (PAM) having the sequence NRG. gRNA 20 bp spacer sequences corresponding to the PAM were identified, as shown in SEQ ID NOs: 42,375-44,067 of the Sequence Listing.

Example 62—CRISPR/SaCas9 Target Sites for the HGD Gene

Exons 1-2 of the HGD gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 44,068-44,281 of the Sequence Listing.

Example 63—CRISPR/StCas9 Target Sites for the HGD Gene

Exons 1-2 of the HGD gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 44,282-44,364 of the Sequence Listing.

Example 64—CRISPR/TdCas9 Target Sites for the HGD Gene

Exons 1-2 of the HGD gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 44,365-44,383 of the Sequence Listing.

Example 65—CRISPR/NmCas9 Target Sites for the HGD Gene

Exons 1-2 of the HGD gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 44,384-44,584 of the Sequence Listing.

Example 66—CRISPR/Cpf1 Target Sites for the HGD Gene

Exons 1-2 of the HGD gene were scanned for target sites. Each area was scanned for a protospacer adjacent motif (PAM) having the sequence YTN. gRNA 22 bp spacer sequences corresponding to the PAM were identified, as shown in SEQ ID NOs: 44,585-46,909 of the Sequence Listing.

Example 67—CRISPR/SpCas9 Target Sites for the Lp(a) Gene

Exons 1-2 of the Lp(a) gene were scanned for target sites. Each area was scanned for a protospacer adjacent motif (PAM) having the sequence NRG. gRNA 20 bp spacer sequences corresponding to the PAM were identified, as shown in SEQ ID NOs: 46,910-50,704 of the Sequence Listing.

Example 68—CRISPR/SaCas9 Target Sites for the Lp(a) Gene

Exons 1-2 of the Lp(a) gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 50,705-51,114 of the Sequence Listing.

Example 69—CRISPR/StCas9 Target Sites for the Lp(a) Gene

Exons 1-2 of the Lp(a) gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 51,115-51,250 of the Sequence Listing.

Example 70—CRISPR/TdCas9 Target Sites for the Lp(a) Gene

Exons 1-2 of the Lp(a) gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 51,251-51,285 of the Sequence Listing.

Example 71—CRISPR/NmCas9 Target Sites for the Lp(a) Gene

Exons 1-2 of the Lp(a) gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 51,286-51,653 of the Sequence Listing.

Example 72—CRISPR/Cpf1 Target Sites for the Lp(a) Gene

Exons 1-2 of the Lp(a) gene were scanned for target sites. Each area was scanned for a protospacer adjacent motif (PAM) having the sequence YTN. gRNA 22 bp spacer sequences corresponding to the PAM were identified, as shown in SEQ ID NOs: 51,654-56,274 of the Sequence Listing.

Example 73—CRISPR/SpCas9 Target Sites for the PCSK9 Gene

Exons 1-2 of the PCSK9 gene were scanned for target sites. Each area was scanned for a protospacer adjacent motif (PAM) having the sequence NRG. gRNA 20 bp spacer sequences corresponding to the PAM were identified, as shown in SEQ ID NOs: 56,275-58,294 of the Sequence Listing.

Example 74—CRISPR/SaCas9 Target Sites for the PCSK9 Gene

Exons 1-2 of the PCSK9 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 58,295-58,481 of the Sequence Listing.

Example 75—CRISPR/StCas9 Target Sites for the PCSK9 Gene

Exons 1-2 of the PCSK9 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 58,482-58,517 of the Sequence Listing.

Example 76—CRISPR/TdCas9 Target Sites for the PCSK9 Gene

Exons 1-2 of the PCSK9 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 58,518-58,531 of the Sequence Listing.

Example 77—CRISPR/NmCas9 Target Sites for the PCSK9 Gene

Exons 1-2 of the PCSK9 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 58,532-58,671 of the Sequence Listing.

Example 78—CRISPR/Cpf1 Target Sites for the PCSK9 Gene

Exons 1-2 of the PCSK9 gene were scanned for target sites. Each area was scanned for a protospacer adjacent motif (PAM) having the sequence YTN. gRNA 22 bp spacer sequences corresponding to the PAM were identified, as shown in SEQ ID NOs: 58,672-60,465 of the Sequence Listing.

Example 79—CRISPR/SaCas9 Target Sites for the Serpina1 Gene

Exons 1-2 of the Serpina1 gene were scanned for target sites. Each area was scanned for a protospacer adjacent motif (PAM) having the sequence NRG. gRNA 20 bp spacer sequences corresponding to the PAM were identified, as shown in SEQ ID NOs: 60,466-61,603 of the Sequence Listing.

Example 80—CRISPR/SaCas9 Target Sites for the Serpina1 Gene

Exons 1-2 of the Serpina1 gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 61,604-61,696 of the Sequence Listing.

Example 81—CRISPR/StCas9 Target Sites for the Serpina1 Gene

Exons 1-2 of the Serpina1 gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 61,697-61,708 of the Sequence Listing.

Example 82—CRISPR/TdCas9 Target Sites for the Serpina1 Gene

Exons 1-2 of the Serpina1 gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 61,709-61,711 of the Sequence Listing.

Example 83—CRISPR/NmCas9 Target Sites for the Serpina1 Gene

Exons 1-2 of the Serpina1 gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 61,712-61,762 of the Sequence Listing.

Example 84—CRISPR/Cpf1 Target Sites for the Serpina1 Gene

Exons 1-2 of the Serpina1 gene were scanned for target sites. Each area was scanned for a protospacer adjacent motif (PAM) having the sequence YTN. gRNA 22 bp spacer sequences corresponding to the PAM were identified, as shown in SEQ ID NOs: 61,763-62,566 of the Sequence Listing.

Example 85—CRISPR/SpCas9 Target Sites for the TF Gene

Exons 1-2 of the TF gene were scanned for target sites. Each area was scanned for a protospacer adjacent motif (PAM) having the sequence NRG. gRNA 20 bp spacer sequences corresponding to the PAM were identified, as shown in SEQ ID NOs: 62,567-63,398 of the Sequence Listing.

Example 86—CRISPR/SaCas9 Target Sites for the TF Gene

Exons 1-2 of the TF gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 63,399-63,484 of the Sequence Listing.

Example 87—CRISPR/StCas9 Target Sites for the TF Gene

Exons 1-2 of the TF gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 63,485-63,496 of the Sequence Listing.

Example 88—CRISPR/TdCas9 Target Sites for the TF Gene

Exons 1-2 of the TF gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 63,497-63,503 of the Sequence Listing.

Example 89—CRISPR/NmCas9 Target Sites for the TF Gene

Exons 1-2 of the TF gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 63,504-63,547 of the Sequence Listing.

Example 90—CRISPR/Cpf1 Target Sites for the TF Gene

Exons 1-2 of the TF gene were scanned for target sites. Each area was scanned for a protospacer adjacent motif (PAM) having the sequence YTN. gRNA 22 bp spacer sequences corresponding to the PAM were identified, as shown in SEQ ID NOs: 63,548-64,183 of the Sequence Listing.

Example 91—CRISPR/SpCas9 Target Sites for the TTR Gene

Exons 1-2 of the TTR gene were scanned for target sites. Each area was scanned for a protospacer adjacent motif (PAM) having the sequence NRG. gRNA 20 bp spacer sequences corresponding to the PAM were identified, as shown in SEQ ID NOs: 64,184-64,483 of the Sequence Listing.

Example 92—CRISPR/SaCas9 Target Sites for the TTR Gene

Exons 1-2 of the TTR gene were scanned for target sites. Each area was scanned for a protospacer adjacent motif (PAM) having the sequence NNGRRT. gRNA 20 bp spacer sequences corresponding to the PAM were identified, as shown in SEQ ID NOs: 64,484-64,524 of the Sequence Listing.

Example 93—CRISPR/StCas9 Target Sites for the TTR Gene

Exons 1-2 of the TTR gene were scanned for target sites. Each area was scanned for a protospacer adjacent motif (PAM) having the sequence NNAGAAW. gRNA 20 bp spacer sequences corresponding to the PAM were identified, as shown in SEQ ID NOs: 64,525-64,541 of the Sequence Listing.

Example 94—CRISPR/TdCas9 Target Sites for the TTR Gene

Exons 1-2 of the TTR gene were scanned for target sites. Each area was scanned for a protospacer adjacent motif (PAM) having the sequence NAAAAC. gRNA 20 bp spacer sequences corresponding to the PAM were identified, as shown in SEQ ID NOs: 64,542-64,543 of the Sequence Listing.

Example 95—CRISPR/NmCas9 Target Sites for the TTR Gene

Exons 1-2 of the TTR gene were scanned for target sites. Each area was scanned for a protospacer adjacent motif (PAM) having the sequence NNNNGHTT. gRNA 20 bp spacer sequences corresponding to the PAM were identified, as shown in SEQ ID NOs: 64,544-64,578 of the Sequence Listing.

Example 96—CRISPR/Cpf1 Target Sites for the TTR Gene

Exons 1-2 of the TTR gene were scanned for target sites. Each area was scanned for a protospacer adjacent motif (PAM) having the sequence YTN. gRNA 22 bp spacer sequences corresponding to the PAM were identified, as shown in SEQ ID NOs: 64,579-64,980 of the Sequence Listing.

Example 97—Bioinformatics Analysis of the Guide Strands

Candidate guides will be screened and selected in a multi-step process that involves both theoretical binding and experimentally assessed activity. By way of illustration, candidate guides having sequences that match a particular on-target site, such as a site within the HFE gene, with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locus, and relatively lower off-target activity to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the CRISPR/Cas9/Cpf1 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.bme.gatech.edu) compiles such similarities. Other bioinformatics tools include, but are not limited to, GUIDO, autoCOSMID, and CCtop.

Bioinformatics were used to minimize off-target cleavage in order to reduce the detrimental effects of mutations and chromosomal rearrangements. Studies on CRISPR/Cas9 systems suggested the possibility of high off-target activity due to nonspecific hybridization of the guide strand to DNA sequences with base pair mismatches and/or bulges, particularly at positions distal from the PAM region. Therefore, it is important to have a bioinformatics tool that can identify potential off-target sites that have insertions and/or deletions between the RNA guide strand and genomic sequences, in addition to base-pair mismatches. The bioinformatics-based tool, COSMID (CRISPR Off-target Sites with Mismatches, Insertions and Deletions) was therefore used to search genomes for potential CRISPR off-target sites (available on the web at crispr.bme.gatech.edu). COSMID output ranked lists of the potential off-target sites based on the number and location of mismatches, allowing more informed choice of target sites, and avoiding the use of sites with more likely off-target cleavage.

Additional bioinformatics pipelines were employed that weigh the estimated on- and/or off-target activity of gRNA targeting sites in a region. Other features that may be used to predict activity include information about the cell type in question, DNA accessibility, chromatin state, transcription factor binding sites, transcription factor binding data, and other CHIP-seq data. Additional factors are weighed that predict editing efficiency, such as relative positions and directions of pairs of gRNAs, local sequence features and micro-homologies.

Example 98—Testing of Preferred Guides in Cells for On-Target Activity

The gRNAs predicted to have the lowest off-target activity will then be tested for on-target activity in a model cell line, such as Huh-7 cells, and evaluated for indel frequency using TIDE or next generation sequencing. TIDE is a web tool to rapidly assess genome editing by CRISPR-Cas9 of a target locus determined by a guide RNA (gRNA or sgRNA). Based on quantitative sequence trace data from two standard capillary sequencing reactions, the TIDE software quantifies the editing efficacy and identifies the predominant types of insertions and deletions (indels) in the DNA of a targeted cell pool. See Brinkman et al, Nucl. Acids Res. (2014) for a detailed explanation and examples. Next-generation sequencing (NGS), also known as high-throughput sequencing, is the catch-all term used to describe a number of different modern sequencing technologies including: Illumina (Solexa) sequencing, Roche 454 sequencing, Ion torrent: Proton/PGM sequencing, and SOLiD sequencing. These recent technologies allow one to sequence DNA and RNA much more quickly and cheaply than the previously used Sanger sequencing, and as such have revolutionised the study of genomics and molecular biology.

Transfection of tissue culture cells, allows screening of different constructs and a robust means of testing activity and specificity. Tissue culture cell lines, such as Huh-7 cells, are easily transfected and result in high activity. These or other cell lines will be evaluated to determine the cell lines that match with hepatocytes and provide the best surrogate. These cells will then be used for many early stage tests. For example, individual gRNAs for *S. pyogenes* Cas9 will be transfected into the cells using plasmids, such as, for example, CTx-1, CTx-2, or CTx-3, which are suitable for expression in human cells. Several days later, the genomic DNA is harvested and the target site amplified by PCR. The cutting activity can be measured by the rate of insertions, deletions and mutations introduced by NHEJ repair of the free DNA ends. Although this method cannot differentiate correctly repaired sequences from uncleaved DNA, the level of cutting can be gauged by the amount of mis-repair. Off-target activity can be observed by amplifying identified putative off-target sites and using similar methods to detect cleavage. Translocation can also be assayed using primers flanking cut sites, to determine if specific cutting and translocations happen. Un-guided assays have been developed allowing complementary testing of off-target cleavage including guide-seq. The gRNA or pairs of gRNA with significant activity can then be followed up in cultured cells to measure correction of the HFE mutation. Off-target events can be followed again. Similarly hepatocytes can be transfected and the level of gene correction and possible off-target events measured. These experiments allow optimization of nuclease and donor design and delivery.

Example 99—Testing of Preferred Guides in Cells for Off-Target Activity

The gRNAs having the best on-target activity from the TIDE and next generation sequencing studies in the above example will then be tested for off-target activity using whole genome sequencing. Candidate gRNAs will be more completely evaluated in hepatocytes or iPSCs.

Example 100—Testing Different Approaches for HDR Gene Editing

After testing the gRNAs for both on-target activity and off-target activity, mutation correction and knock-in strategies will be tested for HDR gene editing.

For the mutation correction approach, donor DNA template will be provided as a short single-stranded oligonucleotide, a short double-stranded oligonucleotide (PAM sequence intact/PAM sequence mutated), a long single-stranded DNA molecule (PAM sequence intact/PAM sequence mutated) or a long double-stranded DNA molecule (PAM sequence intact/PAM sequence mutated). In addition, the donor DNA template will be delivered by AAV.

For the cDNA knock-in approach, a single-stranded or double-stranded DNA having homologous arms to the 6p21.3 region may include more than 40 nt of the first exon (the first coding exon) of the HFE gene, the complete CDS of the HFE gene and 3'UTR of the HFE gene, and at least 40 nt of the following intron. The single-stranded or double-stranded DNA having homologous arms to the 6p21.3 region may include more than 80 nt of the first exon of the HFE gene, the complete CDS of the HFE gene and 3'UTR of the HFE gene, and at least 80 nt of the following intron. The single-stranded or double-stranded DNA having homologous arms to the 6p21.3 region may include more than 100 nt of the first exon of the HFE gene, the complete CDS of the HFE gene and 3'UTR of the HFE gene, and at least 100 nt of the following intron. The single-stranded or double-stranded DNA having homologous arms to the 6p21.3 region may include more than 150 nt of the first exon of the HFE gene, the complete CDS of the HFE gene and 3'UTR of the HFE gene, and at least 150 nt of the following intron. The single-stranded or double-stranded DNA having homologous arms to the 6p21.3 region may include more than 300 nt of the first exon of the HFE gene, the complete CDS of the HFE gene and 3'UTR of the HFE gene, and at least 300 nt of the following intron. The single-stranded or double-stranded DNA having homologous arms to the 6p21.3 region may include more than 400 nt of the first exon of the HFE gene, the complete CDS of the HFE gene and 3'UTR of the HFE gene, and at least 400 nt of the following intron. Alternatively, the DNA template will be delivered by AAV.

Example 101—Re-Assessment of Lead CRISPR-Cas9/DNA Donor Combinations

After testing the different strategies for HDR gene editing, the lead CRISPR-Cas9/DNA donor combinations will be re-assessed in primary human hepatocytes for efficiency of deletion, recombination, and off-target specificity. Cas9 mRNA or RNP will be formulated into lipid nanoparticles for delivery, sgRNAs will be formulated into nanoparticles or delivered as AAV, and donor DNA will be formulated into nanoparticles or delivered as AAV.

Example 102—In Vivo Testing in Relevant Animal Model

After the CRISPR-Cas9/DNA donor combinations have been re-assessed, the lead formulations will be tested in vivo in a FRG mouse model with the livers repopulated with human hepatocytes (normal or HFE deficient human hepatocytes).

Culture in human cells allows direct testing on the human target and the background human genome, as described above.

Preclinical efficacy and safety evaluations can be observed through engraftment of modified mouse or human hepatocytes in FRG mice. The modified cells can be observed in the months after engraftment.

Example 103—In Vitro Transcribed (IVT) gRNA Screen

Figure 3B:
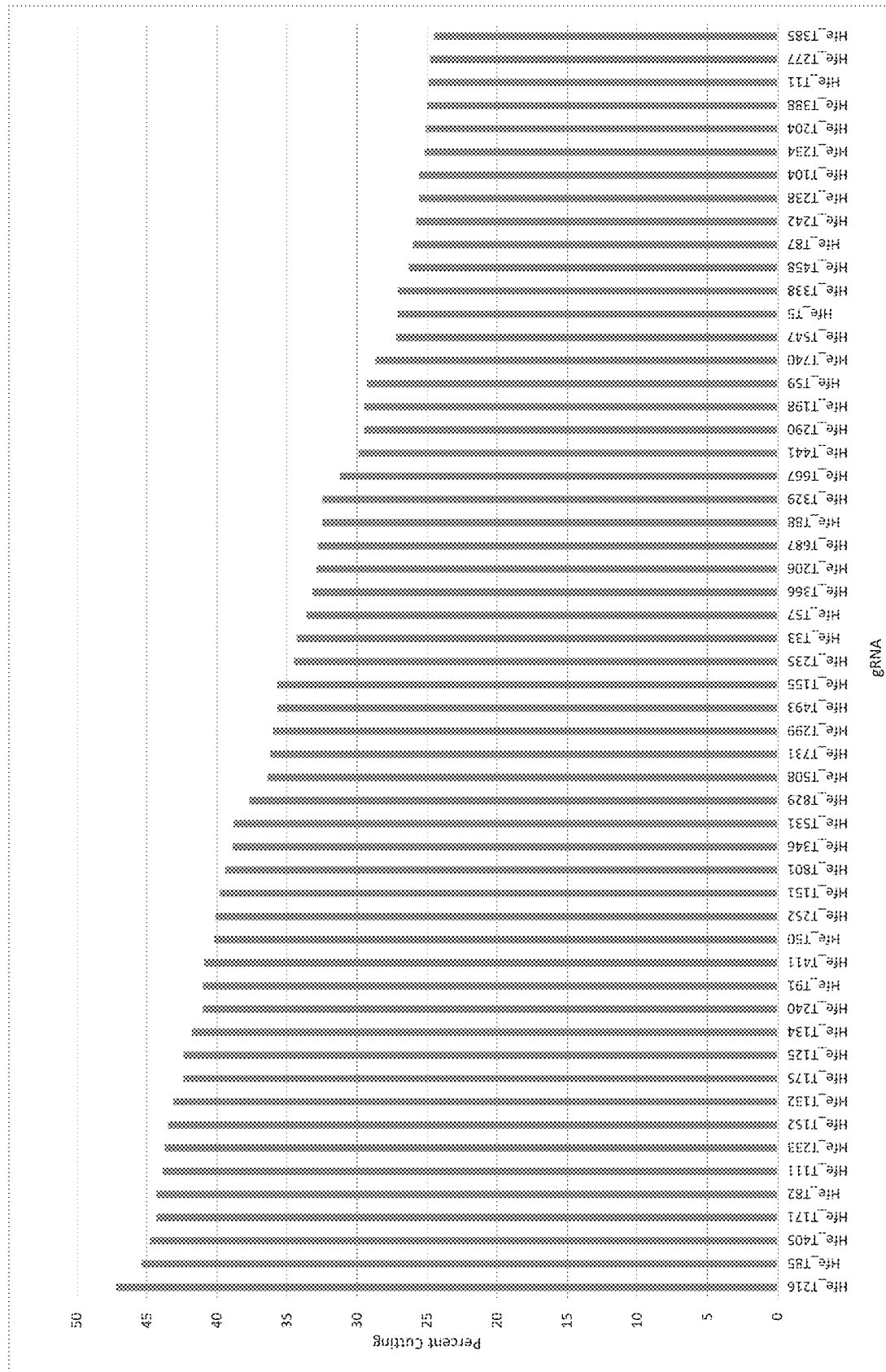
FIG. 3B describes the cutting efficiency of S. pyogenes gRNAs in HEK293T cells targeting the HFE gene.
Figure 3C:
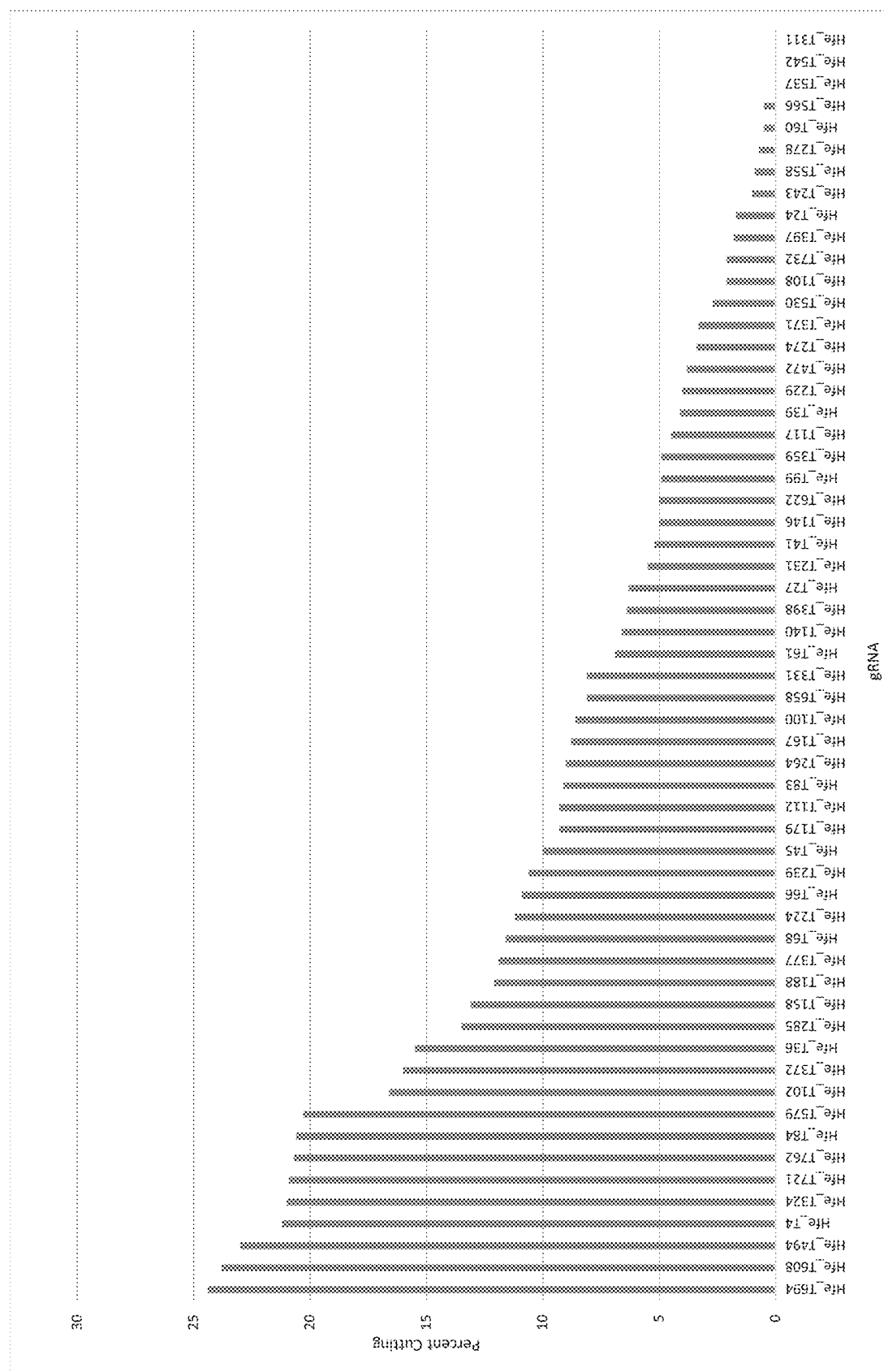
FIG. 3C describes the cutting efficiency of S. pyogenes gRNAs in HEK293T cells targeting the HFE gene.

To identify a large spectrum of pairs of gRNAs able to edit the cognate DNA target region, an in vitro transcribed (IVT) gRNA screen was conducted. The HFE genomic sequence, located on Chromosome 6 (6p21.3 region), was submitted for analysis using a gRNA design software. The resulting list of gRNAs were narrowed to a list of about 200 gRNAs based on uniqueness of sequence (only gRNAs without a perfect match somewhere else in the genome were screened) and minimal predicted off targets. This set of gRNAs were in vitro transcribed, and transfected using messenger Max into HEK293T cells that stably express Cas9. Cells were harvested 48 hours post transfection, the genomic DNA was isolated, and cutting efficiency was evaluated using TIDE analysis. (FIGS. 2A-2D; FIGS. 3A-C).

Note Regarding Illustrative Examples

While the present disclosure provides descriptions of various specific aspects for the purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

SEQUENCE LISTING

The patent contains a lengthy sequence listing. A copy of the sequence listing is available in electronic form from the USPTO web site (https://seqdata.uspto.gov/?pageRequest=docDetail&DocID=US12186406B2). An electronic copy of the sequence listing will also be available from the USPTO upon request and payment of the fee set forth in 37 CFR 1.19(b)(3).

What is claimed is:

1. An in vivo method for treating a patient with hereditary hemochromatosis (HHC), the method comprising the step of editing within or near a haemochromatosis (HFE) gene or within or near regulatory elements of the HFE gene, or editing within or near a safe harbor locus in a cell of the patient, wherein the editing step comprises:

introducing into the cell of the patient one or more deoxyribonucleic acid (DNA) endonucleases or one or more mRNAs encoding the one or more DNA endonucleases to effect one or more single-strand breaks (SSBs) or double-strand breaks (DSBs) (i) within or near the HFE gene or within or near the regulatory elements of the HFE gene that result in a permanent deletion, insertion, or correction of one or more mutations within or near the HFE gene and restoration of the HFE protein activity, or (ii) within or near a safe harbor locus; and introducing into the cell of the patient one or more guide ribonucleic acids (gRNAs) comprising a spacer sequence that is an RNA sequence and selected from the group consisting of SEQ ID NOs: 3610, 973, 378, 1029, 3598, 3634, 1142, 388, 1121, 3678, 1137, 3531, 3654, 1045, 1096, 3558, and 3585 in which T is replaced by U.

2. The method of claim 1, wherein the one or more DNA endonucleases is a Cas1, Cas1B, Cas2, Cas3, Cas4, Cas5, Cas6, Cas7, Cas8, Cas9, Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1, a codon-optimized version thereof, a modified version thereof, or combinations thereof.

3. The method of claim 2, wherein the one or more DNA endonucleases are introduced into the cell.

4. The method of claim 2, wherein the one or more mRNAs encoding the one or more DNA endonucleases are introduced into the cell.

5. The method of claim 1, wherein the one or more gRNAs are single-molecule guide RNA (sgRNAs).

6. The method of claim 5, wherein the one or more sgRNAs are modified.

7. The method of claim 1, wherein the method further comprises: introducing into the cell a polynucleotide donor template comprising at least a portion of the wild-type HFE gene, at least a portion of DNA sequences that encode wild-type regulatory elements of the HFE gene, or at least a portion of cDNA encoding the wild-type HFE gene.

8. The method of claim 7, wherein the donor template is either a single or double stranded polynucleotide.

9. The method of claim 7, wherein the donor template has homology arms homologous to the 6p21.3 region.

10. The method of claim 1, wherein the method further comprises:

introducing into the cell a polynucleotide donor template comprising at least a portion of the wild-type HFE gene, and wherein the one or more DNA endonucleases is Cas9 and/or Cpf1 that effect one SSB or DSB within or near the HFE gene or within or near the safe harbor locus that results in the permanent insertion of the at least a portion of the wild-type HFE gene within or near the HFE gene or within or near the safe harbor locus.

11. The method of claim 1, wherein the one or more gRNAs are directed to one or more of the following pathological variants: C282Y, H63D, and S65C.

12. The method of claim 1, wherein the insertion or correction is by homology directed repair (HDR).

13. The method of claim 10, wherein the Cas9 and/or Cpf1 mRNA, the one or more gRNAs, and the polynucleotide donor template are either formulated into separate lipid nanoparticles or into the same lipid nanoparticle.

14. The method of claim 1, wherein the HFE gene is located on Chromosome 6.

15. The method of claim 1, wherein the one or more DNA endonucleases are pre-complexed with the one or more gRNAs.

16. The method of claim 1, wherein the one or more mRNAs encoding the one or more DNA endonucleases and the one or more gRNAs are either formulated into separate lipid nanoparticles or into the same lipid nanoparticle, or wherein the one or more mRNAs encoding the one or more DNA endonucleases are formulated into a lipid nanoparticle and the one or more gRNAs are introduced into the cell by an adeno-associated virus (AAV).

17. The method of claim 1, wherein the one or more DNA endonucleases comprise a Cas9 endonuclease.

18. The method of claim 10, wherein the Cas9 and/or Cpf1 mRNA is formulated into a lipid nanoparticle and both the one or more gRNAs and the polynucleotide donor template are introduced into the cell by an adeno-associated virus (AAV).

19. The method of claim 7, wherein the at least a portion of the wild-type HFE gene or the at least a portion of cDNA encoding the wild-type HFE gene is exon 1, exon 2, exon 3, exon 4, exon 5, exon 6, exon 7, intronic regions, or a combination thereof.

20. The method of claim 1, wherein
the one or more gRNAs are two gRNAs, wherein the one or more DNA endonucleases effect a pair of DSBs, the first at a 5' DSB locus and the second at a 3' DSB locus within or near the HFE gene or within or near regulatory elements of the HFE gene that result in a permanent deletion of the chromosomal DNA between the 5' DSB locus and the 3' DSB locus, and wherein the two gRNAs are modified.

* * * * *